United States Patent
Bouillot et al.

(10) Patent No.: US 11,352,334 B2
(45) Date of Patent: *Jun. 7, 2022

(54) 3-(5-CHLORO-2-OXOBENZO[D]OXAZOL-3(2H)-YL) PROPANOIC ACID DERIVATIVES AS KMO INHIBITORS

(71) Applicant: THE UNIVERSITY COURT OF THE UNIVERSITY OF EDINBURGH, Edinburgh (GB)

(72) Inventors: Anne Marie Jeanne Bouillot, Les Ulis (FR); Olivier Mirguet, Les Ulis (FR); John Liddle, Stevenage (GB); Anne Louise Walker, Stevenage (GB)

(73) Assignee: THE UNIVERSITY COURT OF THE UNIVERSITY OF EDINBURGH, Edinburgh (GB)

(*) Notice: Subject to any disclaimer, the term of this patent is extended or adjusted under 35 U.S.C. 154(b) by 0 days.

This patent is subject to a terminal disclaimer.

(21) Appl. No.: 16/521,283

(22) Filed: Jul. 24, 2019

(65) Prior Publication Data

US 2019/0345117 A1   Nov. 14, 2019

Related U.S. Application Data

(63) Continuation of application No. 15/104,821, filed as application No. PCT/EP2014/078221 on Dec. 17, 2014, now abandoned.

(30) Foreign Application Priority Data

Dec. 19, 2013 (GB) ....................... 1322512

(51) Int. Cl.

| | | |
|---|---|---|
| *C07D 263/58* | (2006.01) | |
| *C07D 413/12* | (2006.01) | |
| *C07C 309/30* | (2006.01) | |
| *C07C 279/14* | (2006.01) | |
| *C07C 211/13* | (2006.01) | |
| *C07C 215/10* | (2006.01) | |
| *C07C 223/02* | (2006.01) | |

(Continued)

(52) U.S. Cl.
CPC .......... *C07D 263/58* (2013.01); *C07C 211/13* (2013.01); *C07C 211/27* (2013.01); *C07C 215/10* (2013.01); *C07C 223/02* (2013.01); *C07C 229/26* (2013.01); *C07C 279/14* (2013.01); *C07C 309/30* (2013.01); *C07D 413/12* (2013.01)

(58) Field of Classification Search
CPC ... C07D 263/58; C07D 413/12; C07C 211/13; C07C 211/27; C07C 215/10; C07C 223/02; C07C 229/26; C07C 279/14; C07C 309/30; A61P 9/00; A61P 43/00; A61P 37/02; A61P 31/12; A61P 31/04; A61P 25/28; A61P 25/24; A61P 25/18; A61P 25/16; A61P 25/14; A61P 25/00; A61P 21/00; A61P 17/02; A61P 13/12; A61P 11/00; A61P 1/18; A61P 1/16; A61P 1/04; A61P 1/00; A61K 31/423; A61K 31/4439; A61K 31/501; A61K 31/506

See application file for complete search history.

(56) References Cited

U.S. PATENT DOCUMENTS

4,370,340 A   1/1983 Ueda et al.

FOREIGN PATENT DOCUMENTS

| JP | S 54-98330 | 8/1979 |
|---|---|---|
| SU | 1143745 | 3/1985 |

(Continued)

OTHER PUBLICATIONS

Corresponding English Language Abstract for JP S 54-98330 and Description for SU 1143745 A are Attached.

(Continued)

*Primary Examiner* — Sarah Pihonak
*Assistant Examiner* — Jason Deck
(74) *Attorney, Agent, or Firm* — Casimir Jones S.C.; Lisa Mueller

(57) ABSTRACT

A compound of formula (I) or a salt thereof are provided:

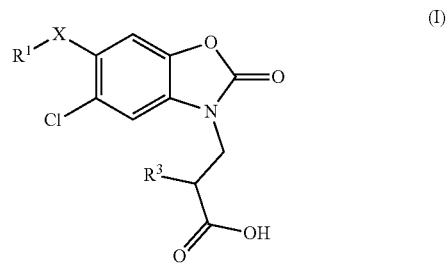

(I)

wherein $R^1$, X and $R^3$ are defined in the specification, useful in the treatment of disorders mediated by KMO such as acute pancreatitis, chronic kidney disease, other conditions associated with systemic inflammatory response syndrome (SIRS), Huntington's disease, Alzheimer's disease, spinocerebellar ataxias, Parkinson's disease, AIDS-dementia complex, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel, severe acute hepatic disease, severe acute hepatic encephalopathy or acute renal failure.

7 Claims, No Drawings

(51) Int. Cl.
  C07C 229/26 (2006.01)
  C07C 211/27 (2006.01)

(56) References Cited

FOREIGN PATENT DOCUMENTS

| SU | 1143745 A | 3/1985 | | |
|---|---|---|---|---|
| WO | WO 01/094311 A1 | 12/2001 | | |
| WO | WO-2006090235 A1 | * | 8/2006 | ........... C07C 233/51 |
| WO | WO 2013/033085 A1 | 3/2013 | | |
| WO | WO 2013/151707 A1 | 10/2013 | | |

OTHER PUBLICATIONS

Onkol et al., "2-0xobenzazolin-3-YL) Alkanoic Acid Derivatives and Antinociceptive Activity", Journal of Faculty of Pharmacy of Gazi University, vol. 19, No. 1, pp. 15-24 (2002).
15104821—STN Search May 1, 2017, 9 pages.
Alberti-Giani et al., "Cloning and Function expression of human kynurenine 3-monooxygenase." FEBS Letters 1997, 410:407-412.
Amaral et al. "The causative role and therapeutic potential of the kynurenine pathway in neurodegenerative disease." Journal of Molecular medicine 2013, 91(6): 705-713.
Dabrowski et al., "Changes in Plasma Kynurenic Acid Concentration in Septic Shock Patients Undergoing Continuous Veno-Venous Haemofiltration." Inflammation, Feb. 2014, 37(1): 223-234.
Kobayashi et al., "A metabolomics-based approach for predicting stages of chronic kidney disease." Biochemical and Biophysical Research Communications, vol. 445, Issue 2, Mar. 7, 2014, pp. 412-416.
Lotgers et al., "Increased Plasma Kynurenine Values and Kynurenine-Tryptophan Ratios After Major Trauma Are Early Indicators for The Development Of Sepsis." Shock 2009, vol. 32(1):29Y34.
Mole et al., "Tryptophan catabolites in mesenteric lymph may contribute to pancreatitis-associated organ failure." British Journal of Surgery, Jul. 1, 2008, 95: 855-867.
Onkol et al., "Synthesis and Antinociceptive Activity of 2-[(2-Oxobenzothiazolin-3-yl)methyl]-5-aminoalkyl/aryl-1,3,4-thiadiazole." Turk J Chem 2004, 28: 461-468.
Pawlak, "Tissue factor/its pathway inhibitor system and kynurenines in chronic kidney disease patients on conservative treatment." Blood Coagulation & Fibrinolysis: Oct. 2009, 20(7):590-594.
Pellegrin et al., "Enhanced Enzymatic Degradation of Tryptophan By Indoleamine 2,3-Dioxygenase Contributes to The Tryptophan-Deficient State Seen After Major Trauma." Shock 2005, 23(3):209-215.
Zhao, "Plasma Kynurenic Acid/Tryptophan Ratio: A Sensitive and Reliable Biomarker for the Assessment of Renal Function." Renal Failure 2013, 35:5: 648-653.
Kalcheva & Simov, "On the cyanethylation of benzoxazolthione, benzoxazolone and some of its derivatives." Yearbook of The Sofia University "Clement of Ohrid" Faculty of Chemistry, vol. 64, 1969-1970, pp. 34-42.

* cited by examiner

3-(5-CHLORO-2-OXOBENZO[D]OXAZOL-3(2H)-YL) PROPANOIC ACID DERIVATIVES AS KMO INHIBITORS

FIELD OF THE INVENTION

The present invention relates to novel 5-chlorobenzo[d]oxazol-2(3H)-one derivatives having pharmacological activity, processes for their preparation, pharmaceutical compositions containing them and their use in the treatment of various disorders.

BACKGROUND OF THE INVENTION

Kynurenine monooxygenase (KMO) is a flavin adenine dinucleotide (FAD) dependent monooxygenase located on the outer mitochondrial membrane. KMO is known to oxidise L-Kynurenine (KYN) to 3-hydroxykynurenine (3HK) as part of the major route of catabolism of tryptophan. 3HK is then converted to 3-hydroxyanthranilic acid and quinolinic acid by kynureninase (KYNU) and 3-hydroxyanthranilate 3,4-dioxygenase (3-HAAO).

KMO is highly expressed in tissues including the liver, placenta, kidney [Alberati-Giani, FEBS Lett. 410:407-412 (1997)] endothelial cells and monocytes and at a lower level in microglia and macrophages in the brain.

Increased levels of 3HK and quinolinic acid and reduced levels of Kynurenic acid (KYNA), which is formed from kynurenine by an alternative pathway, have been implicated in a number of diseases including Huntington's Disease, Parkinson's Disease, Alzheimer's Disease, amyotrophic lateral sclerosis (ALS) [Amaral, Outeiro et Al. Journal of Molecular medicine 2013: 91(6): 705-713] and Acute Pancreatitis [Mole, McFerran et al. British Journal of Surgery 2008: 95: 855-867]. In the CNS 3-HK and quinolinic acid have been shown to be neurotoxic and KYNA to have neuroprotective effects. Inhibition of KMO oxidative activity would therefore be expected to result in reduced levels of 3-HK and quinolinic acid and increased levels of KYNA and to potentially show benefit for these diseases.

There is a large body of evidence showing that tryptophan metabolism is also altered in a range of acute injury settings. For instance, increased kynurenine levels have been associated with the development of sepsis following trauma [Pellegrin, 2005, Logters, 2009], while increased levels of both kynurenine and 3-HK correlate with the development of organ failure in acute pancreatitis [Mole, McFerran et al. British Journal of Surgery 2008: 95: 855-867]. This dysregulation of tryptophan metabolism is in part accounted for by the induction of indolamine 2,3 dioxygenase (IDO, the enzyme that converts tryptophan to N-formyl-kynurenine)) as part of the inflammatory cascade, but the development of organ dysfunction appears dependent on the downstream metabolites [Mole, McFerran et al. British Journal of Surgery 2008: 95: 855-867]

Acute pancreatitis (AP) results from local injury to the organ driven by factors such as excessive alcohol consumption or gallstones. The arising abdominal pain is extremely severe, and patients will invariably present to an emergency department rapidly following onset of an attack, with elevation of serum amylase used as a diagnostic. In the majority of cases, the disease is self limiting, and the pain resolves within 24-36 hours. However for the remaining 20-30% of patients a systemic inflammatory response occurs, resulting in rapid progression to multiple organ dysfunction (MOD). This leads to a prolonged stay in ICU (averaging 17 days), with a mortality rate of over 30%. Despite this high unmet need and the seriousness of the disease, there are no effective treatments available, with current standard of care being purely supportive.

SU1143745 discloses methods for the preparation of derivatives of 3-(3-benzoxazolonyl)propanoic acid. JP54098330 discloses the reaction of benzoxazolepropionic acid derivatives with thionyl chloride in the manufacture of tricyclic oxazoloquinoline derivative or thiazoloquinoline derivative bactericides for agricultural and horticultural use. Onkol et al, (J. Faculty of Pharmacy of Gazi University (202), 19(1), 15-24) discloses 2-oxobenzazolin-3-yl)alkanoic acid derivatives and the testing of these compounds for antinociceptive activity. Kalcheva V et al (Godishnik na Sofiiskiya Universitet Sv. Kliment Okhridski, Khimicheski Fakultet (1972), Volume Date 1969-1970, 64, 33-42) discloses cyanoethylation of benzoxazolethione, benzoxazolone, and some benzoxazolone derivatives.

WO2013016488, WO2011091153, WO2010017132, WO2010017179, WO2010011302, WO2008022286 and WO2008022281 describe inhibitors of KMO for targeting neurodegenerative disorders or diseases; EP1475385, EP1424333 describe inhibitors of KMO for targeting degenerative and inflammatory conditions. There remains a need for effective KMO inhibitors which are suitable for intravenous administration for use in the treatment of acute pancreatitis and other conditions associated with systemic inflammatory response syndrome (SIRS).

A structurally novel class of compounds has now been found which provides inhibitors of KMO which may be useful in the treatment of acute pancreatitis and acute conditions associated with systemic inflammatory response syndrome (SIRS).

SUMMARY OF THE INVENTION

The present invention therefore provides, in a first aspect, a compound of formula (I) or a pharmaceutically acceptable salt thereof for use as a medicament:

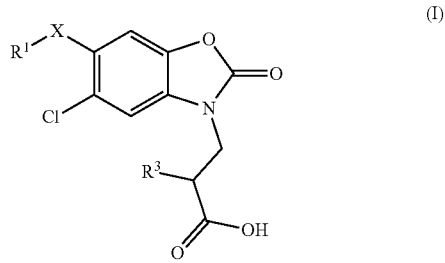

(I)

wherein:
X is a bond and $R^1$ is —H, -halo or —CN; or
X is —CH$_2$— and $R^1$ is —H or —C$_{1-3}$alkyl; or
X is —O— and $R^1$ is —C$_{1-4}$alkyl, —(CH$_2$)$_m$CF$_3$, —CHR$^2$CH$_2$OMe, —(CH$_2$)$_n$C$_{3-4}$cycloalkyl, —(CH$_2$)$_n$oxetane, -benzyl or —CHR$^2$heteroaryl; wherein heteroaryl may be additionally substituted by halo, methyl, ethyl or O;
m=1 or 2;
n=0 or 1;
$R^2$=—H, -methyl or -ethyl; and
$R^3$=H or methyl.

The term "alkyl" as used herein refers to a straight or branched alkyl group in all isomeric forms. The term "C$_{1-4}$ alkyl" refers to an alkyl group, containing at least 1, and at most 4 carbon atoms. Examples of such $C_{1-4}$alkyl groups include methyl, ethyl, propyl, iso-propyl, n-butyl, iso-butyl, sec-butyl, and tert-butyl.

The term "halogen" as used herein refers to e.g. fluorine (F), chlorine (Cl), bromine (Br), or iodine (I) and the term "halo" refers to e.g. fluoro (—F), chloro (—Cl), bromo (—Br) or iodo (—I).

The term "heteroaryl" as used herein refers to a 5- or 6-membered unsaturated ring which comprises one or more heteroatoms. When the term "heteroaryl" represents a 5-membered group it contains a heteroatom selected from O, N or S and may optionally contain a further 1 to 3 nitrogen atoms. When the term "heteroaryl" represents a 6-membered group it contains from 1 to 3 nitrogen atoms. Examples of such 5- or 6-membered heteroaryl rings include, but are not limited to, pyrrolyl, triazolyl, thiadiazolyl, tetrazolyl, imidazolyl, pyrazolyl, isothiazolyl, thiazolyl, isoxazolyl, oxazolyl, oxadiazolyl, furazanyl, furanyl, thienyl, pyridyl, pyrimidinyl, pyrazinyl, pyridazinyl and triazinyl.

The term "cycloalkyl" as used herein refers to a carbocyclic ring comprising carbon atoms. The term "$C_{3-4}$cycloalkyl" refers to a carbocyclic ring containing 3 or 4 carbon atoms, for example cyclopropyl or cyclobutyl.

In further aspects of the invention, the invention provides a compound of formula (I) or a salt thereof, and a pharmaceutical composition comprising the compound of formula (I) or a pharmaceutically acceptable salt thereof and a pharmaceutically acceptable carrier.

DETAILED DESCRIPTION OF THE INVENTION

As discussed above, in a first aspect, the invention provides a compound of formula (I) or a pharmaceutically acceptable salt thereof for use as a medicament.

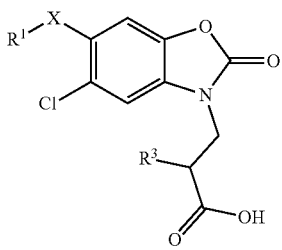
(I)

wherein:
X is a bond and $R^1$ is —H, -halo or —CN; or
X is —$CH_2$— and $R^1$ is —H or —$C_{1-3}$alkyl; or
X is —O— and $R^1$ is —$C_{1-4}$alkyl, —$(CH_2)_mCF_3$, —$CHR^2CH_2OMe$, —$(CH_2)_nC_{3-4}$cycloalkyl, —$(CH_2)_n$oxetane, -benzyl or —$CHR^2$heteroaryl; wherein heteroaryl may be additionally substituted by halo, methyl, ethyl or O;
m=1 or 2;
n=0 or 1;
$R^2$=—H, -methyl or -ethyl; and
$R^3$=H or methyl.

In a further aspect, the invention provides a compound of formula (I') or a pharmaceutically acceptable salt thereof for use as a medicament.

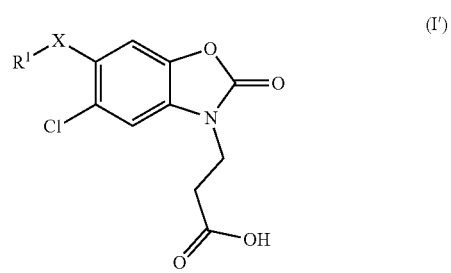
(I')

wherein:
X is a bond and $R^1$ is —H, -halo or —CN; or
X is —$CH_2$— and $R^1$ is —H or —$C_{1-3}$alkyl; or
X is —O— and $R^1$ is —$C_{1-4}$alkyl, —$(CH_2)_mCF_3$, —$CHR^2CH_2OMe$, —$(CH_2)_nC_{3-4}$cycloalkyl, —$(CH_2)_n$oxetane, -benzyl or —$CHR^2$heteroaryl; wherein heteroaryl may be additionally substituted by methyl or O;
m=1 or 2;
n=0 or 1; and
$R^2$=—H or -methyl.

Compounds of formula (I) or pharmaceutically acceptable salts thereof are inhibitors of KMO activity and are thus believed to be of potential use in the treatment of conditions or disorders mediated by KMO.

Such conditions or disorders include acute pancreatitis, other conditions associated with systemic inflammatory response syndrome (SIRS), Huntington's disease, Alzheimer's disease, spinocerebellar ataxias, Parkinson's disease, AIDS-dementia complex, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel, severe acute hepatic disease, severe acute hepatic encephalopathy or acute renal failure.

Additional conditions or disorders include hyperproliferative diseases of benign or malignant behaviour, in which cells of various tissues and organs exhibit aberrant patterns of growth, proliferation, migration, signalling, senescence, and death. Generally hyperproliferative disease refers to diseases and disorders associated with the uncontrolled proliferation of cells, including but not limited to uncontrolled growth of organ and tissue cells resulting in cancers and benign tumours. Hyperproliferative disorders associated with endothelial cells can result in diseases of angiogenesis such as angiomas, endometriosis, obesity, age-related macular degeneration and various retinopathies, as well as the proliferation of ECs and smooth muscle cells that cause restenosis as a consequence of stenting in the treatment of atherosclerosis. Hyperproliferative disorders involving fibroblasts (i.e. fibrogenesis) include but are not limited to disorders of excessive scaring (i.e. fibrosis) such as age-related macular degeneration, cardiac remodelling and failure associated with myocardial infarction, excessive wound healing such as commonly occurs as a consequence of surgery or injury, keloids, and fibroid tumours and stenting.

Further such conditions or disorders include transplant rejection (suppression of T-cells) and graft vs host disease, chronic kidney disease, systemic inflammatory disorders, brain inflammatory disorders including malaria and African trypanosomiasis, stroke, and pneumococcal meningitis.

Further such indications or disorders include cirrhosis, chronic pancreatitis, liver fibrosis, lung fibrosis and ischemia-reperfusion injury Further such conditions or disorders further include, for example, neurodegenerative diseases, psychiatric or neurological diseases or disorders, Creutzfeld-Jacob disease, trauma-induced neurodegeneration, high-pressure neurological syndrome, dystonia, olivopontocerebellar atrophy, multiple sclerosis, epilepsy, consequences of stroke, cerebral ischemia, ischemic disorders including stroke (focal ischemia), hypoxia, multi-infarct dementia, consequences of cerebral trauma or damage, damage to the spinal cord, dementia such as senile dementia, AIDS-induced encephalopathy, other infection related encephalopathy, viral or bacterial meningitis, infectious diseases caused by viral, bacterial and other parasites, (for example, general central nervous system (CNS) infections such as viral, bacterial or parasitic infection, for example, poliomyelitis, Lyme disease (*Borrelia burgdorferi* infection)) septic shock, and malaria, cancers, cancers with cerebral localization, hepatic encephalopathy, systemic lupus, analgesia and opiate withdrawal symptoms, feeding behaviour, psychiatric disorders, such as insomnia, depression, schizophrenia, severe deficit in working memory, severe deficit in long term memory storage, decrease in cognition, severe deficit in attention, severe deficit in executive functioning, slowness in information processing, slowness in neural activity, anxiety, generalized anxiety disorders, panic anxiety, obsessive compulsive disorders, social phobia, performance anxiety, post-traumatic stress disorder, acute stress reaction, adjustment reaction, separation anxiety disorder, alcohol withdrawal anxiety, depressive disorders, disorders of the developing or aged brain, diabetes, and complications thereof, Tourette's syndrome, Fragile X syndrome, autism spectrum disorders, disorders that cause severe and pervasive impairment in thinking feeling, language and the ability to relate to others, mood disorders, psychological disorders characterized by abnormalities of emotional state, such as without limitation, bipolar disorder, unipolar depression, major depression, endogenous depression, involutional depression, reactive depression, psychotic depression, depression caused by underlying medical conditions, depressive disorders, cyclothymic disorders, dysthymic disorders, mood disorders due to general medical condition, mood disorders not otherwise specified and substance-induced mood disorders.

Further such conditions or disorders also include, for example, acute pancreatitis, acute necrotizing pancreatitis, AIDS (disease), analgesia, aseptic meningitis, brain disease, for example, Gilles de la Tourette syndrome, Asperger syndrome, Rett syndrome, pervasive developmental disorders, aging-related brain disease, and developmental brain disease, burnout syndrome, carbon monoxide poisoning, cardiac arrest or insufficiency and hemorrhagic shock (global brain ischemia), cataract formation and aging of the eye, central nervous system disease, cerebrovascular disease, chronic fatigue syndrome, chronic stress, cognitive disorders, convulsive disorders, such as variants of grand mal and petit mal epilepsy and Partial Complex Epilepsy, diabetes mellitus, disease of the nervous system (e.g., dyskinesia, L-DOPA induced movement disorders, drug addiction, pain and cataract), drug dependence, drug withdrawal, feeding disorders, Guillain Barr Syndrome and other neuropathies, Hepatic encephalopathy, immune disease, immunitary disorders and therapeutic treatment aimed at modifying biological responses (for instance administrations of interferons or interleukins), inflammatory disorders of the central and/or peripheral nervous system, Injury (trauma, polytrauma), Mental and behavioral disorders, metabolic disease, pain disease, or disorder selected from a group of inflammatory pain, neuropathic pain or migraine, allodynia, hyperalgesia pain, phantom pain, neuropathic pain related to diabetic neuropathy, multiple organ failure, near drowning, necrosis, neoplasms of the brain, neoplastic disorders including lymphomas and other malignant blood disorders, nervous system disease (high-pressure neurological Syndrome, infection), nicotine addiction and other addictive disorders including alcoholism, cannabis, benzodiazepine, barbiturate, morphine and cocaine dependence, change in appetite, sleep disorders, changes in sleep pattern, lack of energy, fatigue, low self-esteem, self-reproach inappropriate guilt, frequent thoughts of death or suicide, plans or attempts to commit suicide, feelings of hopelessness and worthlessness, psychomotor agitation or retardation, diminished capacity for thinking, concentration, or decisiveness, as a Neuroprotective agent, pain, posttraumatic stress disorder, sepsis, spinal cord disease, spinocerebellar ataxia, systemic lupus erythematosis, traumatic damage to the brain and spinal cord, and tremor syndromes and different movement disorders (dyskinesia), poor balance, bradykinesia, rigidity, tremor, change in speech, loss of facial expression, micrographia, difficulty swallowing, drooling, dementia, confusion, fear, sexual dysfunction, language impairment, impairment in decision making, violent outbursts, aggression, hallucination, apathy, impairment in abstract thinking.

Further such conditions or disorders also include, for example, cardiovascular diseases, which refer to diseases and disorders of the heart and circulatory system. These diseases are often associated with dyslipoproteinemias and/or dyslipidemias. Cardiovascular diseases include, but are not limited to, cardiomegaly, atherosclerosis, myocardial infarction, and congestive heart failure, coronary heart disease, hypertension and hypotension.

In particular, such conditions or disorders include conditions or disorders where elevated levels of tryptophan metabolites have been correlated with severity of disease and poor prognosis, including shock, trauma in patients with multiple organ failure, severe acute pancreatitis and chronic kidney disease (Logters, T. T., et al. (2009) *Shock* 32: 29-34, Dabrowski et al (2014) Inflammation 37: 223-234, Changsirivathanathamrong et al (2011) Critical Care Medicine 39: 2678-2683, Mole, D. J., et al. (2008) *Br J Surg* 95: 855-867, Zhao (2013) Renal Failure 35: 648-653, Pawlak, K. et al (2009) Blood Coagulation and Fibrinolysis 20: 590-594, Kabayashi, T. et al (2014) Biochemical and Biophysical Research Communications 445: 412-416).

Accordingly, in a second aspect, the invention provides a compound of formula (I) or a pharmaceutically acceptable salt thereof wherein X and $R^1$ are as defined above for formula (I) for use in the treatment of any one of the above conditions or disorders, and in particular acute pancreatitis.

The invention further provides a compound of formula (I) or a pharmaceutically acceptable salt thereof wherein X and $R^1$ are as defined above for formula (I) for use in the prophylaxis of any one of the above conditions or disorders, and in particular acute pancreatitis.

The invention further provides a method of treatment of the above conditions or disorders, particularly acute pancreatitis, in mammals including humans, which comprises administering to the sufferer a therapeutically effective amount of a compound of formula (I) or a pharmaceutically acceptable salt thereof wherein X and $R^1$ are as defined above for formula (I).

The invention also provides the use of a compound of formula (I) or a pharmaceutically acceptable salt thereof wherein X and $R^1$ are as defined above for formula (I) in the manufacture of a medicament for use in the treatment of the above conditions or disorders and particularly acute pancreatitis.

In a third aspect, the invention provides a compound of formula (I) or a salt thereof

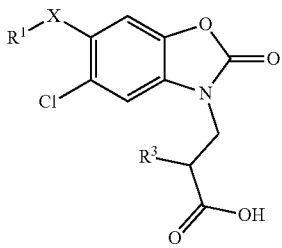

(I)

wherein:

X is a bond and $R^1$ is —H, -halo or —CN; or

X is —CH$_2$— and $R^1$ is —H or —C$_{1-3}$alkyl; or

X is —O— and $R^1$ is —C$_{1-4}$alkyl, —(CH$_2$)$_m$CF$_3$, —CHR$^2$CH$_2$OMe, —(CH$_2$)$_n$C$_{3-4}$cycloalkyl, —(CH$_2$)$_n$oxetane, -benzyl or —CHR$^2$heteroaryl; wherein heteroaryl may be additionally substituted by halo, methyl, ethyl or O;

m=1 or 2;

n=0 or 1;

$R^2$=—H, -methyl or -ethyl; and $R^3$=H or -methyl, provided that the compound of formula (I) or a salt thereof is not 3-(5-chloro-2-oxobenzo[d]oxazol-3(2H)-yl)propanoic acid or 3-(5-chloro-2-oxobenzo[d]oxazol-3(2H)-yl)-2-methylpropanoic acid.

In a further aspect, the invention provides a compound of formula (IA) or a salt thereof

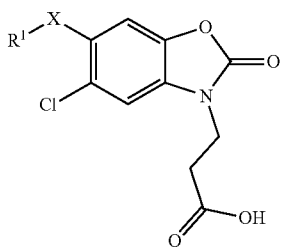

(IA)

wherein:

X is a bond and $R^1$ is -halo or —CN; or

X is —CH$_2$— and $R^1$ is —H or —C$_{1-3}$alkyl; or

X is —O— and $R^1$ is —C$_{1-4}$alkyl, —(CH$_2$)$_m$CF$_3$, —CHR$^2$CH$_2$OMe, —(CH$_2$)$_n$C$_{3-4}$cycloalkyl, —(CH$_2$)$_n$oxetane, -benzyl or —CHR$^2$heteroaryl; wherein heteroaryl may be additionally substituted by methyl or O;

m=1 or 2;

n=0 or 1; and $R^2$=—H or -methyl.

In one embodiment, there is provided a compound of formula (I) or a salt thereof

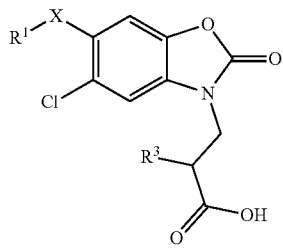

(I)

wherein:

X is a bond and $R^1$ is -halo or —CN; or

X is —CH$_2$— and $R^1$ is —H or —C$_{1-3}$alkyl; or

X is —O— and $R^1$ is —C$_{1-4}$alkyl, —(CH$_2$)$_m$CF$_3$, —CHR$^2$CH$_2$OMe, —(CH$_2$)$_n$C$_{3-4}$cycloalkyl, —(CH$_2$)$_n$oxetane, -benzyl or —CHR$^2$heteroaryl; wherein heteroaryl may be additionally substituted by halo, methyl, ethyl or O;

m=1 or 2;

n=0 or 1;

$R^2$=—H, -methyl or -ethyl; and $R^3$=H or -methyl.

In one embodiment of the compound of formula (I), X is a bond and $R^1$ is —H, -halo or —CN.

In a particular embodiment, X is a bond and $R^1$ is —H, —Cl, —F, —Br or —CN.

In an alternative embodiment, X is —CH$_2$— and $R^1$ is —H or —C$_{1-3}$alkyl.

In a particular embodiment, X is —CH$_2$— and $R^1$ is —H, —CH$_3$ or —CH(CH$_3$)$_2$.

In a more particular embodiment, X is —CH$_2$— and $R^1$ is —H.

In an alternative embodiment, X is —O— and $R^1$ is —C$_{1-4}$alkyl, —(CH$_2$)$_m$CF$_3$, —CHR$^2$CH$_2$OMe, —(CH$_2$)$_n$C$_{3-4}$cycloalkyl, —(CH$_2$)$_n$oxetane, -benzyl or —CHR$^2$heteroaryl; wherein heteroaryl may be additionally substituted by halo, methyl or O.

In an alternative embodiment, X is —O— and $R^1$ is —C$_{1-4}$alkyl, —(CH$_2$)$_m$CF$_3$, —CHR$^2$CH$_2$OMe, —(CH$_2$)$_n$C$_{3-4}$cycloalkyl, —(CH$_2$)$_n$oxetane, -benzyl or —CHR$^2$heteroaryl; wherein heteroaryl may be additionally substituted by methyl or O.

In a more particular embodiment, X is —O— and $R^1$ is —CHR$^2$CH$_2$OMe, —(CH$_2$)$_n$C$_{3-4}$cycloalkyl, or —(CH$_2$)$_n$oxetane.

In a more particular embodiment, X is —O— and $R^1$ is —CHR$^2$heteroaryl.

In a more particular embodiment X is —O— and $R^1$ is —CHR$^2$pyridyl.

In a more particular embodiment X is —O— and $R^1$ is —CHR$^2$-pyrid-2-yl.

In one embodiment, $R^2$ is H.

In an alternative embodiment, $R^2$ is -methyl.

In an alternative embodiment, $R^2$ is ethyl.

In one embodiment $R^3$ is H. In an alternative embodiment $R^3$ is methyl.

In an alternative embodiment, X is —O— and $R^1$ is 1-pyrid-2-ylethyl, methyl, ethyl, isobutyl, cyclopropylmethyl, cyclobutylmethyl, benzyl, 2-methoxyethyl, propyl, 3,3,3-trifluoropropyl, pyrid-2-ylmethyl, isopropyl, cyclobutyl, cyclopropyl, 2,2,2-trifluoroethyl, oxetan-3-yl, oxetan-3-ylmethyl, 1-methoxypropan-2-yl, 6-methylpyridin-3-yl, 2-methylpyridin-4-ylmethyl, pyrid-2-ylmethyl-N-oxide, 1-methyl-1H-imidazol-2-ylmethyl, 2-methylpyridin-3-ylmethyl, pyrimidin-2-ylmethyl, 2-methyloxazol-5- ylmethyl, 5-methyloxazol-2-ylmethyl, 1H-imidazol-2-ylmethyl, pyridazin-3-ylmethyl, 1-(2-methyloxazol-5-yl)ethyl, 1-(5-fluoropyridin-2-yl)ethyl, 1-(5-methylpyridin-2-yl)ethyl, 5-fluoropropyridin-2-ylmethyl, 5-chloropyridin-2-ylmethyl, 1-(5-chloropyridin-2-yl)ethyl, 5-methylpyridin-2-ylmethyl, 1-(6-methylpyridin-2-yl)ethyl, 1-(pyridine-2-yl)propyl, 1-(4-methylpyridin-2-yl)ethyl, 1-(pyridazin-3-yl)ethyl, 6-methylpyridazin-3-ylmethyl, 1-(6-methylpyridazin-3-yl)ethyl, 1-(5-methylpyridin-2-yl)propyl, 1-(5-methylpyridin-2-yl)ethyl, 1-(4-methylpyridin-2-yl)ethyl, 1-(pyridazin-3-yl)ethyl, 6-methylpyridazin-3-ylmethyl, 1-(6-methylpyridazin-3-yl)ethyl, 1-pyrimidin-2-ylethyl, or 1-oxazol-2-ylethyl.

In an alternative embodiment, X is —O— and $R^1$ is 1-pyrid-2-ylethyl, methyl, ethyl, isobutyl, cyclopropylmethyl, cyclobutylmethyl, benzyl, 2-methoxyethyl, propyl, 3,3,3-trifluoropropyl, pyrid-2-ylmethyl, isopropyl, cyclobutyl, cyclopropyl, 2,2,2-trifluoroethyl, oxetan-3-yl, oxetan-3-ylmethyl, 1-methoxypropan-2-yl, 6-methylpyridin-3-yl, 2-methylpyridin-4-ylmethyl, pyrid-2-ylmethyl-N-oxide, 1-methyl-1H-imidazol-2-ylmethyl, 2-methylpyridin-3-ylmethyl, pyrimidin-2-ylmethyl, 2-methyloxazol-5-ylmethyl, 5-methyloxazol-2-ylmethyl, 1H-imidazol-2-ylmethyl or pyridazin-3-ylmethyl.

In an even more particular embodiment, X is —O—, $R^1$ is —CHR$^2$-pyrid-2-yl, and $R^2$ is -methyl.

In an even more particular embodiment, X is —O—, $R^1$ is —CHR$^2$-pyrid-2-yl, $R^2$ is -methyl and $R^3$ is H.

All features and embodiments of compounds of formula (I) apply to compounds of formula (IA) mutatis mutandis. Hereinafter, all references to compounds of formula (I) include compounds of formula (IA).

All features and embodiments of compounds of formula (I) apply to compounds of formula (IA), and (I') mutatis mutandis. Hereinafter, all references to compounds of formula (I) include compounds of formula (IA), and (I').

Prodrugs of the compounds of formula (I) are included within the scope of the present invention. In one embodiment, the compounds of formula (I) or salts thereof are not prodrugs.

As used herein, the term "prodrug" means a compound which is converted within the body, e.g. by hydrolysis in the blood, into its active form that has medical effects.

Pharmaceutically acceptable prodrugs are described in T. Higuchi and V. Stella, Prodrugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987 and in D. Fleishner, S. Ramon and H. Barba "Improved oral drug delivery: solubility limitations overcome by the use of prodrugs", Advanced Drug Delivery Reviews (1996) 19(2) 115-130. Prodrugs are any covalently bonded carriers that release a compound of formula (I) in vivo when such prodrug is administered to a patient. Prodrugs are generally prepared by modifying functional groups in a way such that the modification is cleaved in vivo yielding the parent compound. Prodrugs may include, for example, compounds of this invention wherein the carboxylic acid group is bonded to any group that, when administered to a patient, cleaves to form the carboxylic acid group. Thus, representative examples of prodrugs include (but are not limited to) phosphonate, carbamate, acetate, formate and benzoate derivatives of the carboxylic acid functional group of the compounds of formula (I).

Compounds of formula (I) or salts thereof include the compounds of Examples 1-61 and their salts.

In one embodiment, compounds of formula (I) or salts thereof are selected from the group consisting of:
3-(5-chloro-2-oxobenzo[d]oxazol-3(2H)-yl)propanoic acid;
3-(5-chloro-6-methyl-2-oxobenzo[d]oxazol-3(2H)-yl)propanoic acid;
3-(5-chloro-2-oxo-6-(1-(pyridin-2-yl)ethoxy)benzo[d]oxazol-3(2H)-yl)propanoic acid;
(R)-3-(5-chloro-2-oxo-6-(1-(pyridin-2-yl)ethoxy)benzo[d]oxazol-3(2H)-yl) propanoic acid;
(S)-3-(5-chloro-2-oxo-6-(1-(pyridin-2-yl)ethoxy)benzo[d]oxazol-3(2H)-yl)propanoic acid;
3-(5,6-dichloro-2-oxobenzo[d]oxazol-3(2H)-yl) propanoic acid;
3-(5-chloro-6-fluoro-2-oxobenzo[d]oxazol-3(2H)-yl)propanoic acid;
3-(5-chloro-6-methoxy-2-oxobenzo[d]oxazol-3(2H)-yl)propanoic acid;
3-(5-chloro-6-cyano-2-oxobenzo[d]oxazol-3(2H)-yl)propanoic acid;
3-(6-bromo-5-chloro-2-oxobenzo[d]oxazol-3(2H)-yl)propanoic acid;
3-(5-chloro-6-ethoxy-2-oxobenzo[d]oxazol-3(2H)-yl)propanoic acid;
3-(5-chloro-6-ethyl-2-oxobenzo[d]oxazol-3(2H)-yl)propanoic acid;
3-(5-chloro-6-isobutoxy-2-oxobenzo[d]oxazol-3(2H)-yl) propanoic acid;
3-(5-chloro-6-(cyclopropylmethoxy)-2-oxobenzo[d]oxazol-3(2H)-yl) propanoic acid;
3-(5-chloro-6-(cyclobutylmethoxy)-2-oxobenzo[d]oxazol-3(2H)-yl)propanoic acid;
3-(6-(benzyloxy)-5-chloro-2-oxobenzo[d]oxazol-3(2H)-yl) propanoic acid;
3-(5-chloro-6-(2-methoxyethoxy)-2-oxobenzo[d]oxazol-3(2H)-yl)propanoic acid;
3-(5-chloro-2-oxo-6-propoxybenzo[d]oxazol-3(2H)-yl) propanoic acid;
3-(5-chloro-2-oxo-6-(3,3,3-trifluoropropoxy)benzo[d]oxazol-3(2H)-yl)propanoic acid;
3-(5-chloro-2-oxo-6-(pyridin-2-ylmethoxy)benzo[d]oxazol-3(2H)-yl)propanoic acid;
3-(5-chloro-6-isopropoxy-2-oxobenzo[d]oxazol-3(2H)-yl) propanoic acid;
3-(5-chloro-6-cyclobutoxy-2-oxobenzo[d]oxazol-3(2H)-yl) propanoic acid;
3-(5-chloro-6-cyclopropoxy-2-oxobenzo[d]oxazol-3(2H)-yl)propanoic acid;
3-(5-chloro-2-oxo-6-(2,2,2-trifluoroethoxy)benzo[d]oxazol-3(2H)-yl)propanoic acid;
3-(5-chloro-6-(oxetan-3-yloxy)-2-oxobenzo[d]oxazol-3(2H)-yl)propanoic acid;
3-(5-chloro-6-isobutyl-2-oxobenzo[d]oxazol-3(2H)-yl)propanoic acid;
3-(5-chloro-6-(oxetan-3-ylmethoxy)-2-oxobenzo[d]oxazol-3(2H)-yl)propanoic acid;
3-(5-chloro-6-((1-methoxypropan-2-yl)oxy)-2-oxobenzo[d]oxazol-3(2H)-yl)propanoic acid;
3-(5-chloro-6-((6-methylpyridin-3-yl)methoxy)-2-oxobenzo[d]oxazol-3(2H)-yl)propanoic acid;
3-(5-chloro-6-((2-methylpyridin-4-yl)methoxy)-2-oxobenzo[d]oxazol-3(2H)-yl)propanoic acid;
2-(((3-(2-carboxyethyl)-5-chloro-2-oxo-2,3-dihydrobenzo[d]oxazol-6-yl)oxy)methyl)pyridine 1-oxide;
3-(5-chloro-6-((1-methyl-1H-imidazol-2-yl)methoxy)-2-oxobenzo[d]oxazol-3(2H)-yl)propanoic acid;
3-(5-chloro-6-((2-methylpyridin-3-yl)methoxy)-2-oxobenzo[d]oxazol-3(2H)-yl)propanoic acid;

3-(5-chloro-2-oxo-6-(pyrimidin-2-ylmethoxy)benzo[d]oxazol-3(2H)-yl)propanoic acid;
3-(5-chloro-6-((2-methyloxazol-5-yl) methoxy)-2-oxobenzo[d]oxazol-3(2H)-yl)propanoic acid;
3-(5-chloro-6-((5-methyloxazol-2-yl) methoxy)-2-oxobenzo[d]oxazol-3(2H)-yl)propanoic acid;
3-(6-((1H-imidazol-2-yl)methoxy)-5-chloro-2-oxobenzo[d]oxazol-3(2H)-yl)propanoic acid; and
3-(5-chloro-2-oxo-6-(pyridazin-3-ylmethoxy)benzo[d]oxazol-3(2H)-yl)propanoic acid;
(R)-3-(5-chloro-2-oxo-6-(1-(pyridin-2-yl)ethoxy)benzo[d]oxazol-3(2H)-yl) propanoic acid;
3-(5-chloro-6-(1-(2-methyloxazol-5-yl)ethoxy)-2-oxobenzo[d]oxazol-3(2H)-yl)propanoic acid (racemic);
(R)-3-(5-chloro-6-(1-(5-fluoropyridin-2-yl)ethoxy)-2-oxobenzo[d]oxazol-3(2H)-yl)propanoic acid;
(R)-3-(5-chloro-6-(1-(5-methylpyridin-2-yl)ethoxy)-2-oxobenzo[d]oxazol-3(2H)-yl)propanoic acid;
3-(5-chloro-6-((5-fluoropyridin-2-yl)methoxy)-2-oxobenzo[d]oxazol-3(2H)-yl)propanoic acid;
3-(5-chloro-6-((5-chloropyridin-2-yl) methoxy)-2-oxobenzo[d]oxazol-3(2H)-yl)propanoic acid;
(R)-3-(5-chloro-6-(1-(5-chloropyridin-2-yl)ethoxy)-2-oxobenzo[d]oxazol-3(2H)-yl)propanoic acid;
3-(5-chloro-6-((5-methylpyridin-2-yl)methoxy)-2-oxobenzo[d]oxazol-3(2H)-yl)propanoic acid;
(R)-3-(5-chloro-6-(1-(6-methylpyridin-2-yl)ethoxy)-2-oxobenzo[d]oxazol-3(2H)-yl)propanoic acid;
(R)-3-(5-chloro-2-oxo-6-(1-(pyridin-2-yl) propoxy)benzo[d]oxazol-3(2H)-yl) propanoic acid;
(R)-3-(5-chloro-6-(1-(4-methylpyridin-2-yl)ethoxy)-2-oxobenzo[d]oxazol-3(2H)-yl)propanoic acid;
(R)-3-(5-chloro-2-oxo-6-(1-(pyridazin-3-yl)ethoxy)benzo[d]oxazol-3(2H)-yl) propanoic acid;
(S)-3-(5-chloro-2-oxo-6-(1-(pyridazin-3-yl)ethoxy)benzo[d]oxazol-3(2H)-yl) propanoic acid;
3-(5-chloro-6-((6-methylpyridazin-3-yl) methoxy)-2-oxobenzo[d]oxazol-3(2H)-yl)propanoic acid;
(S)-3-(5-chloro-6-(1-(6-methylpyridazin-3-yl)ethoxy)-2-oxobenzo[d]oxazol-3(2H)-yl)propanoic acid;
(R)-3-(5-chloro-6-(1-(6-methylpyridazin-3-yl)ethoxy)-2-oxobenzo[d]oxazol-3(2H)-yl)propanoic acid;
(R)-3-(5-chloro-6-(1-(5-methylpyridin-2-yl)propoxy)-2-oxobenzo[d]oxazol-3(2H)-yl)propanoic acid;
(S)-3-(5-chloro-6-(1-(5-methylpyridin-2-yl)ethoxy)-2-oxobenzo[d]oxazol-3(2H)-yl)-2-methylpropanoic acid;
(R)-3-(5-chloro-6-(1-(5-methyl pyridin-2-yl)ethoxy)-2-oxobenzo[d]oxazol-3(2H)-yl)-2-methylpropanoic acid;
(S)-3-(5-chloro-6-(1-(5-methylpyridin-2-yl)ethoxy)-2-oxobenzo[d]oxazol-3(2H)-yl)-2-methylpropanoic acid;
(R)-3-(5-chloro-6-(1-(5-methyl pyridin-2-yl)ethoxy)-2-oxobenzo[d]oxazol-3(2H)-yl)-2-methylpropanoic acid;
3-(5-chloro-2-oxo-6-(1-(pyrimidin-2-yl)ethoxy)benzo[d]oxazol-3(2H)-yl)propanoic acid (single unknown enantiomer);
(S)-3-(5-chloro-6-(1-(oxazol-2-yl)ethoxy)-2-oxobenzo[d]oxazol-3(2H)-yl) propanoic acid; and
(R)-(5-chloro-6-(1-(oxazol-2-yl)ethoxy)-2-oxobenzo[d]oxazol-3(2H)-yl)propanoic acid;
and salts thereof In a further embodiment, compounds of formula (I) or salts thereof are selected from the group consisting of:
3-(5-chloro-6-methyl-2-oxobenzo[d]oxazol-3(2H)-yl)propanoic acid;
3-(5-chloro-2-oxo-6-(1-(pyridin-2-yl)ethoxy)benzo[d]oxazol-3(2H)-yl)propanoic acid;
(R)-3-(5-chloro-2-oxo-6-(1-(pyridin-2-yl)ethoxy)benzo[d]oxazol-3(2H)-yl) propanoic acid;
(S)-3-(5-chloro-2-oxo-6-(1-(pyridin-2-yl)ethoxy)benzo[d]oxazol-3(2H)-yl)propanoic acid;
3-(5,6-dichloro-2-oxobenzo[d]oxazol-3(2H)-yl)propanoic acid;
3-(5-chloro-6-fluoro-2-oxobenzo[d]oxazol-3(2H)-yl)propanoic acid;
3-(5-chloro-6-methoxy-2-oxobenzo[d]oxazol-3(2H)-yl)propanoic acid;
3-(5-chloro-6-cyano-2-oxobenzo[d]oxazol-3(2H)-yl)propanoic acid;
3-(6-bromo-5-chloro-2-oxobenzo[d]oxazol-3(2H)-yl)propanoic acid;
3-(5-chloro-6-ethoxy-2-oxobenzo[d]oxazol-3(2H)-yl)propanoic acid;
3-(5-chloro-6-ethyl-2-oxobenzo[d]oxazol-3(2H)-yl)propanoic acid;
3-(5-chloro-6-isobutoxy-2-oxobenzo[d]oxazol-3(2H)-yl) propanoic acid;
3-(5-chloro-6-(cyclopropylmethoxy)-2-oxobenzo[d]oxazol-3(2H)-yl) propanoic acid;
3-(5-chloro-6-(cyclobutylmethoxy)-2-oxobenzo[d]oxazol-3(2H)-yl)propanoic acid;
3-(6-(benzyloxy)-5-chloro-2-oxobenzo[d]oxazol-3(2H)-yl) propanoic acid;
3-(5-chloro-6-(2-methoxyethoxy)-2-oxobenzo[d]oxazol-3(2H)-yl)propanoic acid;
3-(5-chloro-2-oxo-6-propoxybenzo[d]oxazol-3(2H)-yl) propanoic acid;
3-(5-chloro-2-oxo-6-(3,3,3-trifluoropropoxy)benzo[d]oxazol-3(2H)-yl)propanoic acid;
3-(5-chloro-2-oxo-6-(pyridin-2-ylmethoxy)benzo[d]oxazol-3(2H)-yl)propanoic acid;
3-(5-chloro-6-isopropoxy-2-oxobenzo[d]oxazol-3(2H)-yl) propanoic acid;
3-(5-chloro-6-cyclobutoxy-2-oxobenzo[d]oxazol-3(2H)-yl) propanoic acid;
3-(5-chloro-6-cyclopropoxy-2-oxobenzo[d]oxazol-3(2H)-yl)propanoic acid;
3-(5-chloro-2-oxo-6-(2,2,2-trifluoroethoxy)benzo[d]oxazol-3(2H)-yl)propanoic acid;
3-(5-chloro-6-(oxetan-3-yloxy)-2-oxobenzo[d]oxazol-3(2H)-yl)propanoic acid;
3-(5-chloro-6-isobutyl-2-oxobenzo[d]oxazol-3(2H)-yl)propanoic acid;
3-(5-chloro-6-(oxetan-3-ylmethoxy)-2-oxobenzo[d]oxazol-3(2H)-yl)propanoic acid;
3-(5-chloro-6-((1-methoxypropan-2-yl)oxy)-2-oxobenzo[d]oxazol-3(2H)-yl)propanoic acid;
3-(5-chloro-6-((6-methylpyridin-3-yl)methoxy)-2-oxobenzo[d]oxazol-3(2H)-yl)propanoic acid;
3-(5-chloro-6-((2-methylpyridin-4-yl)methoxy)-2-oxobenzo[d]oxazol-3(2H)-yl)propanoic acid;
2-(((3-(2-carboxyethyl)-5-chloro-2-oxo-2,3-dihydrobenzo[d]oxazol-6-yl)oxy)methyl)pyridine 1-oxide;
3-(5-chloro-6-((1-methyl-1H-imidazol-2-yl)methoxy)-2-oxobenzo[d]oxazol-3(2H)-yl)propanoic acid;
3-(5-chloro-6-((2-methylpyridin-3-yl)methoxy)-2-oxobenzo[d]oxazol-3(2H)-yl)propanoic acid;
3-(5-chloro-2-oxo-6-(pyrimidin-2-ylmethoxy)benzo[d]oxazol-3(2H)-yl)propanoic acid;
3-(5-chloro-6-((2-methyloxazol-5-yl) methoxy)-2-oxobenzo[d]oxazol-3(2H)-yl)propanoic acid;
3-(5-chloro-6-((5-methyloxazol-2-yl) methoxy)-2-oxobenzo[d]oxazol-3(2H)-yl)propanoic acid;

3-(6-((1H-imidazol-2-yl)methoxy)-5-chloro-2-oxobenzo[d]
   oxazol-3(2H)-yl)propanoic acid; and
3-(5-chloro-2-oxo-6-(pyridazin-3-ylmethoxy)benzo[d]oxa-
   zol-3(2H)-yl)propanoic acid;
(R)-3-(5-chloro-2-oxo-6-(1-(pyridin-2-yl)ethoxy)benzo[d]
   oxazol-3(2H)-yl) propanoic acid;
3-(5-chloro-6-(1-(2-methyloxazol-5-yl)ethoxy)-2-oxobenzo
   [d]oxazol-3(2H)-yl)propanoic acid (racemic);
(R)-3-(5-chloro-6-(1-(5-fluoropyridin-2-yl)ethoxy)-2-
   oxobenzo[d]oxazol-3(2H)-yl)propanoic acid;
(R)-3-(5-chloro-6-(1-(5-methylpyridin-2-yl)ethoxy)-2-
   oxobenzo[d]oxazol-3(2H)-yl)propanoic acid;
3-(5-chloro-6-((5-fluoropyridin-2-yl)methoxy)-2-oxobenzo
   [d]oxazol-3(2H)-yl)propanoic acid;
3-(5-chloro-6-((5-chloropyridin-2-yl) methoxy)-2-
   oxobenzo[d]oxazol-3(2H)-yl)propanoic acid;
(R)-3-(5-chloro-6-(1-(5-chloropyridin-2-yl)ethoxy)-2-
   oxobenzo[d]oxazol-3(2H)-yl)propanoic acid;
3-(5-chloro-6-((5-methylpyridin-2-yl)methoxy)-2-
   oxobenzo[d]oxazol-3(2H)-yl)propanoic acid;
(R)-3-(5-chloro-6-(1-(6-methylpyridin-2-yl)ethoxy)-2-
   oxobenzo[d]oxazol-3(2H)-yl)propanoic acid;
(R)-3-(5-chloro-2-oxo-6-(1-(pyridin-2-yl) propoxy)benzo
   [d]oxazol-3(2H)-yl) propanoic acid;
(R)-3-(5-chloro-6-(1-(4-methylpyridin-2-yl)ethoxy)-2-
   oxobenzo[d]oxazol-3(2H)-yl)propanoic acid;
(R)-3-(5-chloro-2-oxo-6-(1-(pyridazin-3-yl)ethoxy)benzo
   [d]oxazol-3(2H)-yl) propanoic acid;
(S)-3-(5-chloro-2-oxo-6-(1-(pyridazin-3-yl)ethoxy)benzo
   [d]oxazol-3(2H)-yl) propanoic acid;
3-(5-chloro-6-((6-methylpyridazin-3-yl) methoxy)-2-
   oxobenzo[d]oxazol-3(2H)-yl)propanoic acid;
(R)-3-(5-chloro-6-(1-(6-methylpyridazin-3-yl)ethoxy)-2-
   oxobenzo[d]oxazol-3(2H)-yl)propanoic acid;
(S)-3-(5-chloro-6-(1-(6-methylpyridazin-3-yl)ethoxy)-2-
   oxobenzo[d]oxazol-3(2H)-yl)propanoic acid;
(R)-3-(5-chloro-6-(1-(5-methylpyridin-2-yl)propoxy)-2-
   oxobenzo[d]oxazol-3(2H)-yl)propanoic acid;
(R)-3-(5-chloro-6-(1-(5-methyl pyridin-2-yl)ethoxy)-2-
   oxobenzo[d]oxazol-3(2H)-yl)-2-methylpropanoic acid;
(S)-3-(5-chloro-6-(1-(5-methylpyridin-2-yl)ethoxy)-2-
   oxobenzo[d]oxazol-3(2H)-yl)-2-methylpropanoic acid;
(R)-3-(5-chloro-6-(1-(5-methyl pyridin-2-yl)ethoxy)-2-
   oxobenzo[d]oxazol-3(2H)-yl)-2-methylpropanoic acid;
(S)-3-(5-chloro-6-(1-(5-methylpyridin-2-yl)ethoxy)-2-
   oxobenzo[d]oxazol-3(2H)-yl)-2-methylpropanoic acid;
(R)-3-(5-chloro-2-oxo-6-(1-(pyrimidin-2-yl)ethoxy)benzo
   [d]oxazol-3(2H)-yl) propanoic acid;
(S)-3-(5-chloro-6-(1-(oxazol-2-yl)ethoxy)-2-oxobenzo[d]
   oxazol-3(2H)-yl) propanoic acid; and
(R)-3-(5-chloro-6-(1-(oxazol-2-yl)ethoxy)-2-oxobenzo[d]
   oxazol-3(2H)-yl)propanoic acid;
and salts thereof In one embodiment, compounds of formula (I) or salts thereof are selected from the group consisting of:
3-(5-chloro-6-methyl-2-oxobenzo[d]oxazol-3(2H)-yl)pro-
   panoic acid;
3-(5-chloro-2-oxo-6-(1-(pyridin-2-yl)ethoxy)benzo[d]oxa-
   zol-3(2H)-yl)propanoic acid;
(R)-3-(5-chloro-2-oxo-6-(1-(pyridin-2-yl)ethoxy)benzo[d]
   oxazol-3(2H)-yl) propanoic acid;
(S)-3-(5-chloro-2-oxo-6-(1-(pyridin-2-yl)ethoxy)benzo[d]
   oxazol-3(2H)-yl)propanoic acid;
3-(5,6-dichloro-2-oxobenzo[d]oxazol-3(2H)-yl) propanoic acid;
3-(5-chloro-6-fluoro-2-oxobenzo[d]oxazol-3(2H)-yl)pro-
   panoic acid;
3-(5-chloro-6-methoxy-2-oxobenzo[d]oxazol-3(2H)-yl)pro-
   panoic acid;
3-(5-chloro-6-cyano-2-oxobenzo[d]oxazol-3(2H)-yl)pro-
   panoic acid;
3-(6-bromo-5-chloro-2-oxobenzo[d]oxazol-3(2H)-yl)pro-
   panoic acid;
3-(5-chloro-6-ethoxy-2-oxobenzo[d]oxazol-3(2H)-yl)pro-
   panoic acid;
3-(5-chloro-6-ethyl-2-oxobenzo[d]oxazol-3(2H)-yl)pro-
   panoic acid;
3-(5-chloro-6-isobutoxy-2-oxobenzo[d]oxazol-3(2H)-yl)
   propanoic acid;
3-(5-chloro-6-(cyclopropylmethoxy)-2-oxobenzo[d]oxazol-
   3(2H)-yl) propanoic acid;
3-(5-chloro-6-(cyclobutylmethoxy)-2-oxobenzo[d]oxazol-3
   (2H)-yl)propanoic acid;
3-(6-(benzyloxy)-5-chloro-2-oxobenzo[d]oxazol-3(2H)-yl)
   propanoic acid;
3-(5-chloro-6-(2-methoxyethoxy)-2-oxobenzo[d]oxazol-3
   (2H)-yl)propanoic acid;
3-(5-chloro-2-oxo-6-propoxybenzo[d]oxazol-3(2H)-yl) pro-
   panoic acid;
3-(5-chloro-2-oxo-6-(3,3,3-trifluoropropoxy)benzo[d]oxa-
   zol-3(2H)-yl)propanoic acid;
3-(5-chloro-2-oxo-6-(pyridin-2-ylmethoxy)benzo[d]oxazol-
   3(2H)-yl)propanoic acid;
3-(5-chloro-6-isopropoxy-2-oxobenzo[d]oxazol-3(2H)-yl)
   propanoic acid;
3-(5-chloro-6-cyclobutoxy-2-oxobenzo[d]oxazol-3(2H)-yl)
   propanoic acid;
3-(5-chloro-6-cyclopropoxy-2-oxobenzo[d]oxazol-3(2H)-
   yl)propanoic acid;
3-(5-chloro-2-oxo-6-(2,2,2-trifluoroethoxy)benzo[d]oxazol-
   3(2H)-yl)propanoic acid;
3-(5-chloro-6-(oxetan-3-yloxy)-2-oxobenzo[d]oxazol-3
   (2H)-yl)propanoic acid;
3-(5-chloro-6-isobutyl-2-oxobenzo[d]oxazol-3(2H)-yl)pro-
   panoic acid;
3-(5-chloro-6-(oxetan-3-ylmethoxy)-2-oxobenzo[d]oxazol-
   3(2H)-yl)propanoic acid;
3-(5-chloro-6-((1-methoxypropan-2-yl)oxy)-2-oxobenzo[d]
   oxazol-3(2H)-yl)propanoic acid;
3-(5-chloro-6-((6-methylpyridin-3-yl)methoxy)-2-
   oxobenzo[d]oxazol-3(2H)-yl)propanoic acid;
3-(5-chloro-6-((2-methylpyridin-4-yl)methoxy)-2-
   oxobenzo[d]oxazol-3(2H)-yl)propanoic acid;
2-(((3-(2-carboxyethyl)-5-chloro-2-oxo-2,3-dihydrobenzo
   [d]oxazol-6-yl)oxy)methyl)pyridine 1-oxide;
3-(5-chloro-6-((1-methyl-1H-imidazol-2-yl)methoxy)-2-
   oxobenzo[d]oxazol-3(2H)-yl)propanoic acid;
3-(5-chloro-6-((2-methylpyridin-3-yl)methoxy)-2-
   oxobenzo[d]oxazol-3(2H)-yl)propanoic acid;
3-(5-chloro-2-oxo-6-(pyrimidin-2-ylmethoxy)benzo[d]oxa-
   zol-3(2H)-yl)propanoic acid;
3-(5-chloro-6-((2-methyloxazol-5-yl) methoxy)-2-
   oxobenzo[d]oxazol-3(2H)-yl)propanoic acid;
3-(5-chloro-6-((5-methyloxazol-2-yl) methoxy)-2-
   oxobenzo[d]oxazol-3(2H)-yl)propanoic acid;
3-(6-((1H-imidazol-2-yl)methoxy)-5-chloro-2-oxobenzo[d]
   oxazol-3(2H)-yl)propanoic acid; and
3-(5-chloro-2-oxo-6-(pyridazin-3-ylmethoxy)benzo[d]oxa-
   zol-3(2H)-yl)propanoic acid;
and salts thereof In a further embodiment, compounds of formula (I) or salts thereof are selected from the group consisting of:
(R)-3-(5-chloro-2-oxo-6-(1-(pyridin-2-yl)ethoxy)benzo[d]
   oxazol-3(2H)-yl) propanoic acid;

3-(5-chloro-6-(1-(2-methyloxazol-5-yl)ethoxy)-2-oxobenzo[d]oxazol-3(2H)-yl)propanoic acid (racemic);
(R)-3-(5-chloro-6-(1-(5-fluoropyridin-2-yl)ethoxy)-2-oxobenzo[d]oxazol-3(2H)-yl)propanoic acid;
(R)-3-(5-chloro-6-(1-(5-methylpyridin-2-yl)ethoxy)-2-oxobenzo[d]oxazol-3(2H)-yl)propanoic acid;
3-(5-chloro-6-((5-fluoropyridin-2-yl)methoxy)-2-oxobenzo[d]oxazol-3(2H)-yl)propanoic acid;
3-(5-chloro-6-((5-chloropyridin-2-yl) methoxy)-2-oxobenzo[d]oxazol-3(2H)-yl)propanoic acid;
(R)-3-(5-chloro-6-(1-(5-chloropyridin-2-yl)ethoxy)-2-oxobenzo[d]oxazol-3(2H)-yl)propanoic acid;
3-(5-chloro-6-((5-methylpyridin-2-yl)methoxy)-2-oxobenzo[d]oxazol-3(2H)-yl)propanoic acid;
(R)-3-(5-chloro-6-(1-(6-methylpyridin-2-yl)ethoxy)-2-oxobenzo[d]oxazol-3(2H)-yl)propanoic acid;
(R)-3-(5-chloro-2-oxo-6-(1-(pyridin-2-yl) propoxy)benzo[d]oxazol-3(2H)-yl) propanoic acid;
(R)-3-(5-chloro-6-(1-(4-methylpyridin-2-yl)ethoxy)-2-oxobenzo[d]oxazol-3(2H)-yl)propanoic acid;
(R)-3-(5-chloro-2-oxo-6-(1-(pyridazin-3-yl)ethoxy)benzo[d]oxazol-3(2H)-yl) propanoic acid;
(S)-3-(5-chloro-2-oxo-6-(1-(pyridazin-3-yl)ethoxy)benzo[d]oxazol-3(2H)-yl) propanoic acid;
3-(5-chloro-6-((6-methylpyridazin-3-yl) methoxy)-2-oxobenzo[d]oxazol-3(2H)-yl)propanoic acid;
(R)-3-(5-chloro-6-(1-(6-methylpyridazin-3-yl)ethoxy)-2-oxobenzo[d]oxazol-3(2H)-yl)propanoic acid;
(S)-3-(5-chloro-6-(1-(6-methylpyridazin-3-yl)ethoxy)-2-oxobenzo[d]oxazol-3(2H)-yl)propanoic acid;
(R)-3-(5-chloro-6-(1-(5-methylpyridin-2-yl)propoxy)-2-oxobenzo[d]oxazol-3(2H)-yl)propanoic acid;
(R)-3-(5-chloro-6-(1-(5-methyl pyridin-2-yl)ethoxy)-2-oxobenzo[d]oxazol-3(2H)-yl)-2-methylpropanoic acid;
(S)-3-(5-chloro-6-(1-(5-methylpyridin-2-yl)ethoxy)-2-oxobenzo[d]oxazol-3(2H)-yl)-2-methylpropanoic acid;
(R)-3-(5-chloro-6-(1-(5-methyl pyridin-2-yl)ethoxy)-2-oxobenzo[d]oxazol-3(2H)-yl)-2-methylpropanoic acid;
(S)-3-(5-chloro-6-(1-(5-methylpyridin-2-yl)ethoxy)-2-oxobenzo[d]oxazol-3(2H)-yl)-2-methylpropanoic acid;
3-(5-chloro-2-oxo-6-(1-(pyrimidin-2-yl)ethoxy)benzo[d]oxazol-3(2H)-yl)propanoic acid (single unknown enantiomer);
(R)-3-(5-chloro-6-(1-(oxazol-2-yl)ethoxy)-2-oxobenzo[d]oxazol-3(2H)-yl)propanoic acid; and
(S)-3-(5-chloro-6-(1-(oxazol-2-yl)ethoxy)-2-oxobenzo[d]oxazol-3(2H)-yl) propanoic acid;
and salts thereof The compounds of formula (I) are capable of forming base addition salts. Such salts can be formed by reaction with the appropriate base, optionally in a suitable solvent such as an organic solvent, to give the salt which can be isolated by crystallisation and filtration.

Because of their potential use in medicine, it will be appreciated that for use in medicine the salts of the compounds of formula (I) should be pharmaceutically acceptable. Suitable pharmaceutically acceptable salts will be apparent to those skilled in the art and include those described in Berge, J. Pharm. Sci., 1977, 66, 1-19. Pharmaceutically acceptable base salts include, but are not limited to, ammonium salts, alkali metal salts such as those of sodium and potassium, alkaline earth metal salts such as those of calcium and magnesium and salts with organic bases, including salts of primary, secondary and tertiary amines, such as t-butylamine, cyclohexylamine, dimethylamine, trimethylamine, diethyltriamine, 2-amino-2-(hydroxymethyl)-1,3-propanediol (TRIS) and N-methyl-D-glucamine.

In a further embodiment, compounds of formula (I) or salts thereof are selected from the group consisting of:
3-(5-chloro-6-methyl-2-oxobenzo[d]oxazol-3(2H)-yl)propanoic acid;
2-amino-2-(hydroxymethyl)propane-1,3-diol 3-(5-chloro-6-methyl-2-oxobenzo[d]oxazol-3(2H)-yl)propanoate;
3-(5-chloro-2-oxo-6-(1-(pyridin-2-yl)ethoxy)benzo[d]oxazol-3(2H)-yl)propanoic acid;
(S)-3-(5-chloro-2-oxo-6-(1-(pyridin-2-yl)ethoxy)benzo[d]oxazol-3(2H)-yl)propanoic acid;
2-amino-2-(hydroxymethyl)propane-1,3-diol (S)-3-(5-chloro-2-oxo-6-(1-(pyridin-2-yl)ethoxy)benzo[d]oxazol-3(2H)-yl)propanoate;
(R)-3-(5-chloro-2-oxo-6-(1-(pyridin-2-yl)ethoxy)benzo[d]oxazol-3(2H)-yl) propanoic acid;
2-amino-2-(hydroxymethyl)propane-1,3-diol (R)-3-(5-chloro-2-oxo-6-(1-(pyridin-2-yl)ethoxy)benzo[d]oxazol-3(2H)-yl)propanoate;
3-(5,6-dichloro-2-oxobenzo[d]oxazol-3(2H)-yl)propanoic acid;
3-(5-chloro-6-fluoro-2-oxobenzo[d]oxazol-3(2H)-yl)propanoic acid;
3-(5-chloro-6-methoxy-2-oxobenzo[d]oxazol-3(2H)-yl)propanoic acid;
3-(5-chloro-6-cyano-2-oxobenzo[d]oxazol-3(2H)-yl)propanoic acid;
2-amino-2-(hydroxymethyl)propane-1,3-diol 3-(6-bromo-5-chloro-2-oxobenzo[d]oxazol-3(2H)-yl)propanoate;
2-amino-2-(hydroxymethyl)propane-1,3-diol 3-(5-chloro-6-ethoxy-2-oxobenzo[d]oxazol-3(2H)-yl)propanoate;
2-amino-2-(hydroxymethyl)propane-1,3-diol 3-(5-chloro-6-ethyl-2-oxobenzo[d]oxazol-3(2H)-yl)propanoate;
2-amino-2-(hydroxymethyl)propane-1,3-diol 3-(5-chloro-6-isobutoxy-2-oxobenzo[d]oxazol-3(2H)-yl)propanoate;
2-amino-2-(hydroxymethyl)propane-1,3-diol 3-(5-chloro-6-(cyclopropylmethoxy)-2-oxobenzo[d]oxazol-3(2H)-yl) propanoate;
2-amino-2-(hydroxymethyl)propane-1,3-diol 3-(5-chloro-6-(cyclobutylmethoxy)-2-oxobenzo[d]oxazol-3(2H)-yl) propanoate;
2-amino-2-(hydroxymethyl)propane-1,3-diol 3-(6-(benzyloxy)-5-chloro-2-oxobenzo[d]oxazol-3(2H)-yl)propanoate;
2-amino-2-(hydroxymethyl)propane-1,3-diol 3-(5-chloro-6-(2-methoxyethoxy)-2-oxobenzo[d]oxazol-3(2H)-yl)propanoate;
2-amino-2-(hydroxymethyl)propane-1,3-diol 3-(5-chloro-2-oxo-6-propoxybenzo[d]oxazol-3(2H)-yl)propanoate;
2-amino-2-(hydroxymethyl)propane-1,3-diol 3-(5-chloro-2-oxo-6-(3,3,3-trifluoropropoxy)benzo[d]oxazol-3(2H)-yl) propanoate;
2-amino-2-(hydroxymethyl)propane-1,3-diol 3-(5-chloro-2-oxo-6-(pyridin-2-ylmethoxy)benzo[d]oxazol-3(2H)-yl) propanoate;
2-amino-2-(hydroxymethyl)propane-1,3-diol 3-(5-chloro-6-isopropoxy-2-oxobenzo[d]oxazol-3(2H)-yl)propanoate;
2-amino-2-(hydroxymethyl)propane-1,3-diol 3-(5-chloro-6-cyclobutoxy-2-oxobenzo[d]oxazol-3(2H)-yl)propanoate;
2-amino-2-(hydroxymethyl)propane-1,3-diol 3-(5-chloro-6-cyclopropoxy-2-oxobenzo[d]oxazol-3(2H)-yl)propanoate;
2-amino-2-(hydroxymethyl)propane-1,3-diol 3-(5-chloro-2-oxo-6-(2,2,2-trifluoroethoxy)benzo[d]oxazol-3(2H)-yl) propanoate;

2-amino-2-(hydroxymethyl)propane-1,3-diol 3-(5-chloro-6-(oxetan-3-yloxy)-2-oxobenzo[d]oxazol-3(2H)-yl)propanoate;
2-amino-2-(hydroxymethyl)propane-1,3-diol 3-(5-chloro-6-isobutyl-2-oxobenzo[d]oxazol-3(2H)-yl)propanoate;
2-amino-2-(hydroxymethyl)propane-1,3-diol 3-(5-chloro-6-(oxetan-3-ylmethoxy)-2-oxobenzo[d]oxazol-3(2H)-yl)propanoate;
2-amino-2-(hydroxymethyl)propane-1,3-diol 3-(5-chloro-6-((1-methoxypropan-2-yl)oxy)-2-oxobenzo[d]oxazol-3(2H)-yl)propanoate;
2-amino-2-(hydroxymethyl)propane-1,3-diol 3-(5-chloro-6-((6-methylpyridin-3-yl)methoxy)-2-oxobenzo[d]oxazol-3(2H)-yl) propanoate;
2-amino-2-(hydroxymethyl)propane-1,3-diol 3-(5-chloro-6-((2-methylpyridin-4-yl)methoxy)-2-oxobenzo[d]oxazol-3(2H)-yl) propanoate;
2-(((3-(2-carboxyethyl)-5-chloro-2-oxo-2,3-dihydrobenzo[d]oxazol-6-yl)oxy)methyl)pyridine 1-oxide;
2-amino-2-(hydroxymethyl)propane-1,3-diol 3-(5-chloro-6-((1-methyl-1H-imidazol-2-yl)methoxy)-2-oxobenzo[d]oxazol-3(2H)-yl) propanoate;
2-amino-2-(hydroxymethyl)propane-1,3-diol 3-(5-chloro-6-((2-methylpyridin-3-yl)methoxy)-2-oxobenzo[d]oxazol-3(2H)-yl) propanoate;
2-amino-2-(hydroxymethyl)propane-1,3-diol 3-(5-chloro-2-oxo-6-(pyrimidin-2-ylmethoxy)benzo[d]oxazol-3(2H)-yl) propanoate;
2-amino-2-(hydroxymethyl)propane-1,3-diol 3-(5-chloro-6-((2-methyloxazol-5-yl)methoxy)-2-oxobenzo[d]oxazol-3(2H)-yl)propanoate;
2-amino-2-(hydroxymethyl)propane-1,3-diol 3-(5-chloro-6-((5-methyloxazol-2-yl)methoxy)-2-oxobenzo[d]oxazol-3(2H)-yl)propanoate;
3-(6-((1H-imidazol-2-yl)methoxy)-5-chloro-2-oxobenzo[d]oxazol-3(2H)-yl)propanoic acid; and
2-amino-2-(hydroxymethyl)propane-1,3-diol 3-(5-chloro-2-oxo-6-(pyridazin-3-ylmethoxy)benzo[d]oxazol-3(2H)-yl)propanoate.

In a further embodiment, compounds of formula (I) or salts thereof are selected from the group consisting of:
(R)-3-(5-chloro-2-oxo-6-(1-(pyridin-2-yl)ethoxy)benzo[d]oxazol-3(2H)-yl) propanoic acid hydrochloride;
(R)-3-(5-chloro-2-oxo-6-(1-(pyridin-2-yl)ethoxy)benzo[d]oxazol-3(2H)-yl) propanoic acid compound with sulfuric acid (1:1);
(R)-3-(5-chloro-2-oxo-6-(1-(pyridin-2-yl)ethoxy)benzo[d]oxazol-3(2H)-yl) propanoic acid compound with methanesulfonic acid (1:1);
N-benzyl-2-phenylethanamine (R)-3-(5-chloro-2-oxo-6-(1-(pyridin-2-yl)ethoxy)benzo[d]oxazol-3(2H)-yl)propanoate;
N1,N2-dibenzylethane-1,2-diamine (R)-3-(5-chloro-2-oxo-6-(1-(pyridin-2-yl)ethoxy)benzo[d]oxazol-3(2H)-yl)propanoate;
(2R,3R,4S,5R)-3,4,5,6-tetrahydroxy-2-(methylamino)hexanal (R)-3-(5-chloro-2-oxo-6-(1-(pyridin-2-yl)ethoxy)benzo[d]oxazol-3(2H)-yl) propanoate;
(R)-3-(5-chloro-2-oxo-6-(1-(pyridin-2-yl)ethoxy)benzo[d]oxazol-3(2H)-yl) propanoic acid compound with (S)-2-amino-5-guanidinopentanoic acid (1:1);
(R)-3-(5-chloro-2-oxo-6-(1-(pyridin-2-yl)ethoxy)benzo[d]oxazol-3(2H)-yl) propanoic acid compound with (S)-2,6-diaminohexanoic acid (1:1);
sodium (R)-3-(5-chloro-2-oxo-6-(1-(pyridin-2-yl)ethoxy)benzo[d]oxazol-3(2H)-yl)propanoate;
(R)-3-(5-chloro-2-oxo-6-(1-(pyridin-2-yl)ethoxy)benzo[d]oxazol-3(2H)-yl) propanoic acid compound with 4-methylbenzenesulfonic acid (1:1);
N1-(2-aminoethyl)ethane-1,2-diamine (R)-3-(5-chloro-2-oxo-6-(1-(pyridin-2-yl)ethoxy)benzo[d]oxazol-3(2H)-yl) propanoate;
2-amino-2-(hydroxymethyl)propane-1,3-diol 3-(5-chloro-6-(1-(2-methyloxazol-5-yl)ethoxy)-2-oxobenzo[d]oxazol-3(2H)-yl)propanoate (racemic);
2-amino-2-(hydroxymethyl)propane-1,3-diol (R)-3-(5-chloro-6-(1-(5-fluoropyridin-2-yl)ethoxy)-2-oxobenzo[d]oxazol-3(2H)-yl)propanoate;
2-amino-2-(hydroxymethyl)propane-1,3-diol (R)-3-(5-chloro-6-(1-(5-methylpyridin-2-yl)ethoxy)-2-oxobenzo[d]oxazol-3(2H)-yl)propanoate;
(R)-3-(5-chloro-6-(1-(5-methylpyridin-2-yl)ethoxy)-2-oxobenzo[d]oxazol-3(2H)-yl)propanoic acid;
2-amino-2-(hydroxymethyl)propane-1,3-diol 3-(5-chloro-6-((5-fluoropyridin-2-yl)methoxy)-2-oxobenzo[d]oxazol-3(2H)-yl) propanoate;
2-amino-2-(hydroxymethyl)propane-1,3-diol 3-(5-chloro-6-((5-chloropyridin-2-yl)methoxy)-2-oxobenzo[d]oxazol-3(2H)-yl)propanoate;
2-amino-2-(hydroxymethyl)propane-1,3-diol (R)-3-(5-chloro-6-(1-(5-chloropyridin-2-yl)ethoxy)-2-oxobenzo[d]oxazol-3(2H)-yl)propanoate;
(R)-3-(5-chloro-6-(1-(5-chloropyridin-2-yl)ethoxy)-2-oxobenzo[d]oxazol-3(2H)-yl)propanoic acid;
2-amino-2-(hydroxymethyl)propane-1,3-diol 3-(5-chloro-6-((5-methylpyridin-2-yl)methoxy)-2-oxobenzo[d]oxazol-3(2H)-yl) propanoate;
2-amino-2-(hydroxymethyl)propane-1,3-diol (R)-3-(5-chloro-6-(1-(6-methylpyridin-2-yl)ethoxy)-2-oxobenzo[d]oxazol-3(2H)-yl)propanoate;
2-amino-2-(hydroxymethyl)propane-1,3-diol (R)-3-(5-chloro-2-oxo-6-(1-(pyridin-2-yl)propoxy)benzo[d]oxazol-3(2H)-yl)propanoate;
(R)-3-(5-chloro-2-oxo-6-(1-(pyridin-2-yl) propoxy)benzo[d]oxazol-3(2H)-yl) propanoic acid;
2-amino-2-(hydroxymethyl)propane-1,3-diol (R)-3-(5-chloro-6-(1-(4-methylpyridin-2-yl)ethoxy)-2-oxobenzo[d]oxazol-3(2H)-yl)propanoate;
(R)-3-(5-chloro-2-oxo-6-(1-(pyridazin-3-yl)ethoxy)benzo[d]oxazol-3(2H)-yl) propanoic acid;
(S)-3-(5-chloro-2-oxo-6-(1-(pyridazin-3-yl)ethoxy)benzo[d]oxazol-3(2H)-yl) propanoic acid;
3-(5-chloro-6-((6-methylpyridazin-3-yl) methoxy)-2-oxobenzo[d]oxazol-3(2H)-yl)propanoic acid;
(R)-3-(5-chloro-6-(1-(6-methylpyridazin-3-yl)ethoxy)-2-oxobenzo[d]oxazol-3(2H)-yl)propanoic acid;
(S)-3-(5-chloro-6-(1-(6-methylpyridazin-3-yl)ethoxy)-2-oxobenzo[d]oxazol-3(2H)-yl)propanoic acid;
(R)-3-(5-chloro-6-(1-(5-methylpyridin-2-yl)propoxy)-2-oxobenzo[d]oxazol-3(2H)-yl)propanoic acid;
(R)-3-(5-chloro-6-(1-(5-methyl pyridin-2-yl)ethoxy)-2-oxobenzo[d]oxazol-3(2H)-yl)-2-methylpropanoic acid;
(S)-3-(5-chloro-6-(1-(5-methylpyridin-2-yl)ethoxy)-2-oxobenzo[d]oxazol-3(2H)-yl)-2-methylpropanoic acid;
(R)-3-(5-chloro-6-(1-(5-methyl pyridin-2-yl)ethoxy)-2-oxobenzo[d]oxazol-3(2H)-yl)-2-methylpropanoic acid;
(S)-3-(5-chloro-6-(1-(5-methylpyridin-2-yl)ethoxy)-2-oxobenzo[d]oxazol-3(2H)-yl)-2-methylpropanoic acid;
2-amino-2-(hydroxymethyl)propane-1,3-diol 3-(5-chloro-2-oxo-6-(1-(pyrimidin-2-yl)ethoxy)benzo[d]oxazol-3(2H)-yl)propanoate (single unknown enantiomer);

2-amino-2-(hydroxymethyl)propane-1,3-diol (S)-3-(5-chloro-6-(1-(oxazol-2-yl)ethoxy)-2-oxobenzo[d]oxazol-3(2H)-yl)propanoate; and
2-amino-2-(hydroxymethyl)propane-1,3-diol (R)-3-(5-chloro-6-(1-(oxazol-2-yl)ethoxy)-2-oxobenzo[d]oxazol-3(2H)-yl) propanoate.

In one embodiment, the compound of formula (I) or a salt thereof is:
3-(5-chloro-6-methyl-2-oxobenzo[d]oxazol-3(2H)-yl)propanoic acid or a salt thereof.

In a particular embodiment, the compound of formula (I) or a salt thereof is: 3-(5-chloro-6-methyl-2-oxobenzo[d]oxazol-3(2H)-yl)propanoic acid or a pharmaceutically acceptable salt thereof.

In a more particular embodiment, the compound of formula (I) or a salt thereof is: 3-(5-chloro-6-methyl-2-oxobenzo[d]oxazol-3(2H)-yl)propanoic acid 2-amino-2-(hydroxymethyl)-1,3-propanediol salt.

In an alternative embodiment, the compound of formula (I) or a salt thereof is: 3-(5-chloro-6-methyl-2-oxobenzo[d]oxazol-3(2H)-yl)propanoic acid.

In an alternative embodiment, the compound of formula (I) or a salt thereof is 3-(5-chloro-2-oxo-6-(1-(pyridin-2-yl)ethoxy)benzo[d]oxazol-3(2H)-yl)propanoic acid or a salt thereof.

In one embodiment, the compound of formula (I) or a salt thereof is (S)-3-(5-chloro-2-oxo-6-(1-(pyridin-2-yl)ethoxy)benzo[d]oxazol-3(2H)-yl)propanoic acid or a salt thereof.

In one embodiment, the compound of formula (I) or a salt thereof is (R)-3-(5-chloro-2-oxo-6-(1-(pyridin-2-yl)ethoxy)benzo[d]oxazol-3(2H)-yl)propanoic acid or a salt thereof.

In a particular embodiment, the compound of formula (I) or a salt thereof is 3-(5-chloro-2-oxo-6-(1-(pyridin-2-yl)ethoxy)benzo[d]oxazol-3(2H)-yl)propanoic acid or a pharmaceutically acceptable salt thereof.

In a particular embodiment, the compound of formula (I) or a salt thereof is (S)-3-(5-chloro-2-oxo-6-(1-(pyridin-2-yl)ethoxy)benzo[d]oxazol-3(2H)-yl)propanoic acid or a pharmaceutically acceptable salt thereof.

In a particular embodiment, the compound of formula (I) or a salt thereof is (R)-3-(5-chloro-2-oxo-6-(1-(pyridin-2-yl)ethoxy)benzo[d]oxazol-3(2H)-yl)propanoic acid or a pharmaceutically acceptable salt thereof.

In a more particular embodiment, the compound of formula (I) or a salt thereof is 3-(5-chloro-2-oxo-6-(1-(pyridin-2-yl)ethoxy)benzo[d]oxazol-3(2H)-yl)propanoic acid 2-amino-2-(hydroxymethyl)-1,3-propanediol salt.

In a more particular embodiment the compound of formula (I) or a salt thereof is (R)-3-(5-chloro-2-oxo-6-(1-(pyridin-2-yl)ethoxy)benzo[d]oxazol-3(2H)-yl)propanoic acid 2-amino-2-(hydroxymethyl)-1,3-propanediol salt.

In an alternative embodiment the compound of formula (I) or a salt thereof is (S)-3-(5-chloro-2-oxo-6-(1-(pyridin-2-yl)ethoxy)benzo[d]oxazol-3(2H)-yl)propanoic acid 2-amino-2-(hydroxymethyl)-1,3-propanediol salt.

The invention includes within its scope all possible stoichiometric and non-stoichiometric forms of the salts for the compounds of formula (I).

Certain compounds of formula (I) or salts thereof may exist in the form of solvates. As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include water, methanol, ethanol and acetic acid. If the solvent used is water, the solvate may be referred to as a hydrate.

Certain compounds of formula (I) are capable of existing in stereoisomeric forms. It will be understood that the invention encompasses all geometric and optical isomers of these compounds and the mixtures thereof including racemates. The different stereoisomeric forms may be separated one from the other by methods known in the art (i.e. separation by chiral HPLC) or any given isomer may be obtained by stereospecific or asymmetric synthesis. The invention also extends to any tautomeric forms and mixtures thereof.

The invention also includes isotopically-labelled compounds and salts, which are identical to compounds of formula (I) or salts thereof, but for the fact that one or more atoms are replaced by an atom having an atomic mass or mass number different from the atomic mass or mass number most commonly found in nature. Examples of isotopes that can be incorporated into compounds of formula (I) or salts thereof isotopes of hydrogen, carbon, nitrogen, fluorine, such as $^3$H, $^{11}$C, $^{14}$C and $^{18}$F. Such isotopically-labelled compound of formula (I) or salts thereof are useful in drug and/or substrate tissue distribution assays. For example, $^{11}$C and $^{18}$F isotopes are particularly useful in PET (positron emission tomography). PET is useful in brain imaging. Isotopically labelled compounds of formula (I) and salts thereof can generally be prepared by carrying out the procedures disclosed below, by substituting a readily available isotopically labelled reagent for a non-isotopically labelled reagent. In one embodiment, compounds of formula (I) or salts thereof are not isotopically labelled.

In order to use the compounds of formula (I) in therapy, they will normally be formulated into a pharmaceutical composition in accordance with standard pharmaceutical practice.

In a further aspect, the invention provides a pharmaceutical composition, which comprises a) a compound for formula (I) or a pharmaceutically acceptable salt thereof; and b) one or more pharmaceutically acceptable excipients.

In one embodiment, the compound of formula (I) or a pharmaceutically acceptable salt thereof is 3-(5-chloro-6-methyl-2-oxobenzo[d]oxazol-3(2H)-yl)propanoic acid or a pharmaceutically acceptable salts thereof.

In a further aspect the invention provides a pharmaceutical composition, which comprises a compound of formula (I) or a pharmaceutically acceptable salt thereof, and a pharmaceutically acceptable carrier or excipient.

In a further aspect, the present invention provides a process for preparing a pharmaceutical composition, the process comprising mixing a compound of formula (I) or a pharmaceutically acceptable salt thereof and a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories.

In one embodiment injectable or infusible solutions, or reconstitutable powders, are preferred.

In an alternative embodiment, a composition adapted for oral formulation is preferred.

Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound.

For parenteral administration, fluid unit dosage forms are prepared utilising a compound of the invention or pharmaceutically acceptable salt thereof and a sterile vehicle. Formulations for injection may be presented in unit dosage form e.g. in ampoules or in multi-dose, utilising a compound of the invention or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device. Thus compounds of formula (I) may be formulated for oral, buccal, parenteral, topical (including ophthalmic and nasal), depot or rectal administration or in a form suitable for administration by inhalation or insufflation (either through the mouth or nose).

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 5000 mg, 1.0 to 500 mg or 1.0 to 200 mg and such unit doses may be administered more than once a day, for example two or three times a day. Such therapy may extend for a number of weeks, months or years.

Compounds of formula (I) and their pharmaceutically acceptable salts are therefore of use in the treatment of conditions or disorders which are mediated via KMO. In particular the compounds of formula (I) and their pharmaceutically acceptable salts are of use in the treatment of acute pancreatitis, chronic kidney disease, other conditions associated with systemic inflammatory response syndrome (SIRS), Huntington's disease, Alzheimer's disease, spinocerebellar ataxias, Parkinson's disease, AIDS-dementia complex, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel, severe acute hepatic disease, severe acute hepatic encephalopathy or acute renal failure.

In one embodiment, the compounds of formula (I) and their pharmaceutically acceptable salts are of use in the treatment of acute pancreatitis, other conditions associated with systemic inflammatory response syndrome (SIRS), Huntington's disease, Alzheimer's disease, spinocerebellar ataxias, Parkinson's disease, AIDS-dementia complex, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel, severe acute hepatic disease, severe acute hepatic encephalopathy or acute renal failure.

It is to be understood that "treatment" as used herein includes prophylaxis as well as alleviation of established symptoms, signs and features of disease.

In a further aspect, the invention provides a compound of formula (I) or a pharmaceutically acceptable salt thereof for use in therapy.

The invention further provides a method of treatment of conditions or disorders in mammals including humans which can be mediated via KMO, which method comprises administering to the sufferer a therapeutically safe and effective amount of a compound of formula (I) or a pharmaceutically acceptable salt thereof.

The invention further provides a method of treatment of acute pancreatitis, other conditions associated with systemic inflammatory response syndrome (SIRS), Huntington's disease, Alzheimer's disease, spinocerebellar ataxias, Parkinson's disease, AIDS-dementia complex, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel, severe acute hepatic disease, severe acute hepatic encephalopathy or acute renal failure which method comprises administering to the sufferer a therapeutically safe and effective amount of a compound of formula (I) or a pharmaceutically acceptable salt thereof.

The invention further provides a method of treatment of acute pancreatitis, which method comprises administering to the sufferer a therapeutically safe and effective amount of a compound of formula (I) or a pharmaceutically acceptable salt thereof.

The invention further provides a method of treatment of chronic kidney disease, which method comprises administering to the sufferer a therapeutically safe and effective amount of a compound of formula (I) or a pharmaceutically acceptable salt thereof.

In another aspect, the invention provides for the use of a compound of formula (I) or a pharmaceutically acceptable salt thereof in the manufacture of a medicament for use in the treatment of conditions or disorders mediated via KMO.

In another aspect, the invention provides for the use of a compound of formula (I) or a pharmaceutically acceptable salt thereof in the manufacture of a medicament for use in the treatment of acute pancreatitis, other conditions associated with systemic inflammatory response syndrome (SIRS), Huntington's disease, Alzheimer's disease, spinocerebellar ataxias, Parkinson's disease, AIDS-dementia complex, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel, severe acute hepatic disease, severe acute hepatic encephalopathy or acute renal failure.

In another aspect, the invention provides for the use of a compound of formula (I) or a pharmaceutically acceptable salt thereof in the manufacture of a medicament for use in the treatment of acute pancreatitis.

In another aspect, the invention provides for the use of a compound of formula (I) or a pharmaceutically acceptable salt thereof in the manufacture of a medicament for use in the treatment of chronic kidney disease.

In another aspect, the invention provides for the compound of formula (I) or a pharmaceutically acceptable salt thereof for use in the treatment of conditions or disorders mediated via KMO.

In another aspect, the invention provides for the compound of formula (I) or a pharmaceutically acceptable salt thereof for use in the treatment of acute pancreatitis, other conditions associated with systemic inflammatory response syndrome (SIRS), Huntington's disease, Alzheimer's disease, spinocerebellar ataxias, Parkinson's disease, AIDS-dementia complex, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel, severe acute hepatic disease, severe acute hepatic encephalopathy or acute renal failure.

In another aspect, the invention provides for the compound of formula (I) or a pharmaceutically acceptable salt thereof for use in the treatment of acute pancreatitis.

In another aspect, the invention provides for the compound of formula (I) or a pharmaceutically acceptable salt thereof for use in the treatment of chronic kidney disease.

In another aspect, the invention provides for a pharmaceutical composition for use in the treatment of acute pancreatitis, chronic kidney disease, other conditions associated with systemic inflammatory response syndrome (SIRS), Huntington's disease, Alzheimer's disease, spinocerebellar ataxias, Parkinson's disease, AIDS-dementia complex, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel, severe acute hepatic disease, severe acute hepatic encephalopathy or acute renal failure which comprises a compound of formula (I) or a pharmaceutically acceptable salt thereof and one or more pharmaceutically acceptable excipients.

Compounds of formula (I) wherein X is a bond or —$CH_2$— may be synthesised substantially according to Reaction Scheme 1.

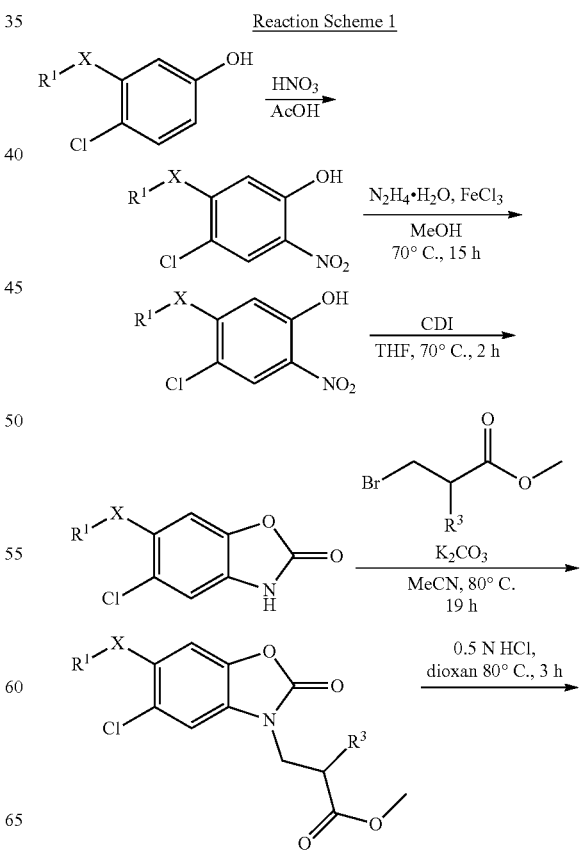

Reaction Scheme 1

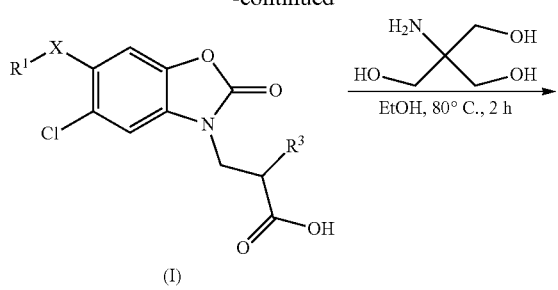

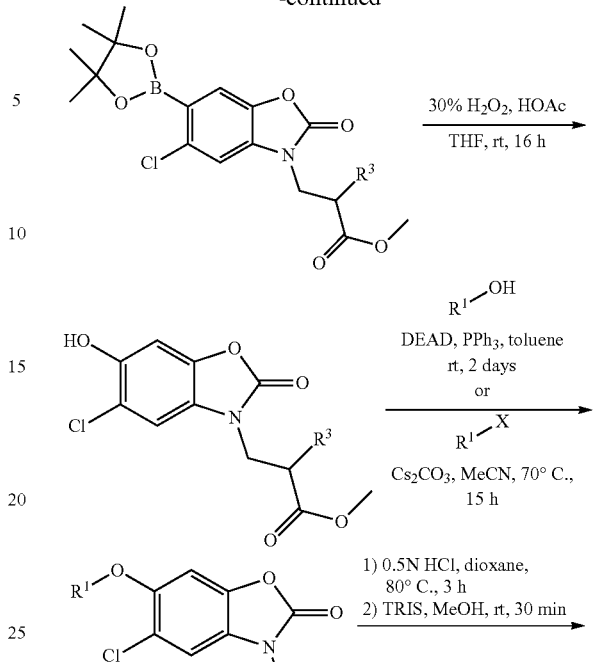

Compounds of formula (I) wherein X is —O— may be synthesised substantially according to Reaction Scheme 2.

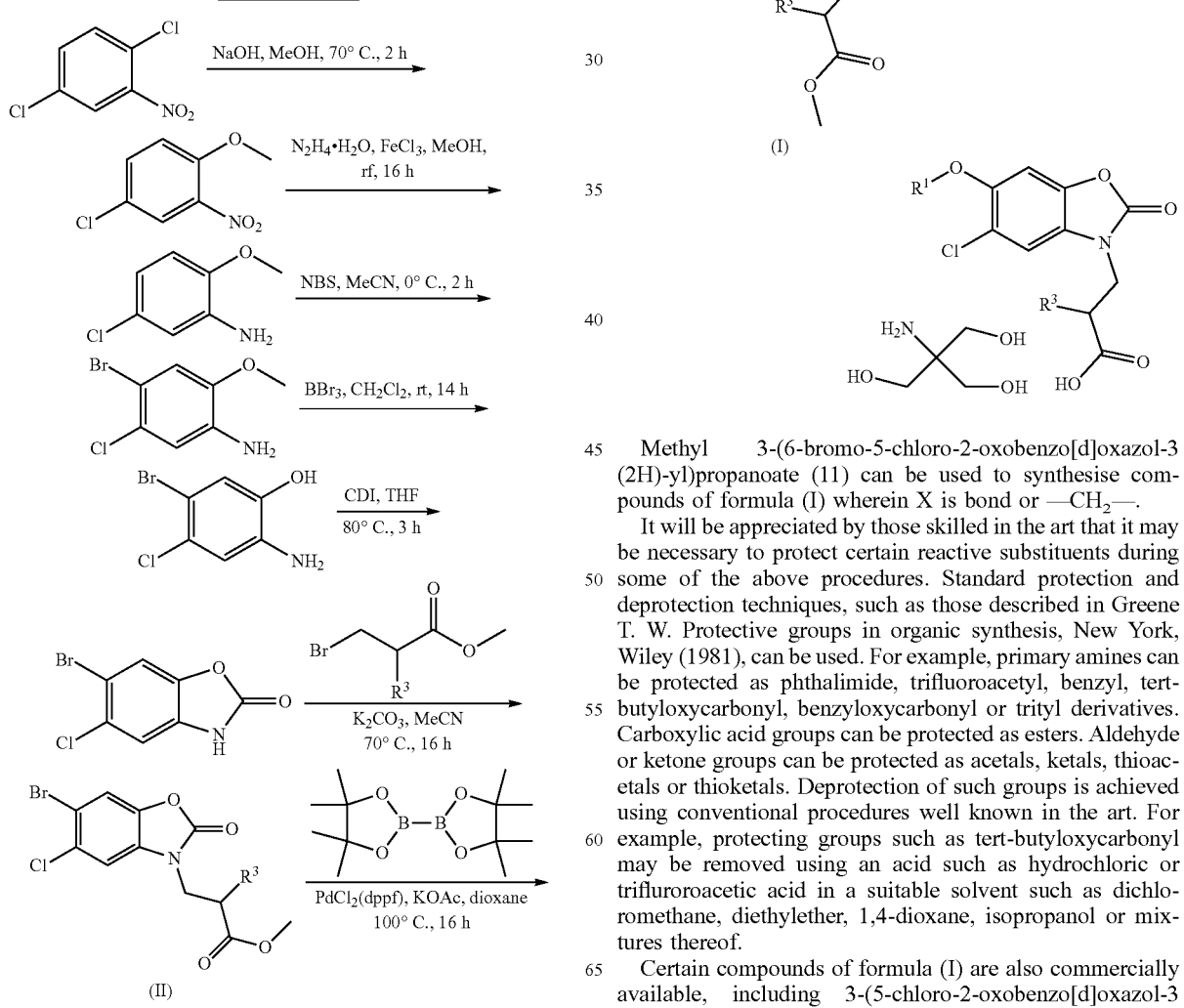

Methyl 3-(6-bromo-5-chloro-2-oxobenzo[d]oxazol-3(2H)-yl)propanoate (11) can be used to synthesise compounds of formula (I) wherein X is bond or —CH$_2$—.

It will be appreciated by those skilled in the art that it may be necessary to protect certain reactive substituents during some of the above procedures. Standard protection and deprotection techniques, such as those described in Greene T. W. Protective groups in organic synthesis, New York, Wiley (1981), can be used. For example, primary amines can be protected as phthalimide, trifluoroacetyl, benzyl, tert-butyloxycarbonyl, benzyloxycarbonyl or trityl derivatives. Carboxylic acid groups can be protected as esters. Aldehyde or ketone groups can be protected as acetals, ketals, thioacetals or thioketals. Deprotection of such groups is achieved using conventional procedures well known in the art. For example, protecting groups such as tert-butyloxycarbonyl may be removed using an acid such as hydrochloric or trifluroroacetic acid in a suitable solvent such as dichloromethane, diethylether, 1,4-dioxane, isopropanol or mixtures thereof.

Certain compounds of formula (I) are also commercially available, including 3-(5-chloro-2-oxobenzo[d]oxazol-3(2H)-yl)propanoic acid.

EXAMPLES

The following Examples illustrate the invention. These Examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

All publications, including but not limited to patents and patent applications, cited in this specification are herein incorporated by reference as if each individual publication were specifically and individually indicated to be incorporated by reference herein as though fully set forth.

The following Intermediates and Examples illustrate the preparation of compounds of the invention.

ABBREVIATIONS

DCM dichloromethane
DEAD diethyl azodicarboxylate
DMSO dimethylsulphoxide
h hour(s)
LCMS liquid chromatography-mass spectrometry
MeCN acetonitrile
min minutes
NMR nuclear magnetic resonance
RT/Rt: retention time
THF tetrahydrofuran
TFA trifluoroacetic acid
TRIS 2-amino-2-(hydroxymethyl)-1,3-propanediol LCMS Conditions LCMS Method A/B/C Agilent 1200-6110,
Signal table: Signal A: 214 nm, Signal B: 254 nm;
Column Temperature: 40° C.
Column: HALO C18 4.6*50 mm, 2.7 µm.

| Method | Solvents | Gradient | Polarity |
|---|---|---|---|
| A | Solvent A: H$_2$O (0.1% formic acid) Solvent B: MeCN (0.1% formic acid) | 0.00 min: A: 95.0% B: 5.0% 1.00 min: A: 5.0% B: 95.0% 2.00 min: A: 5.0% B: 95.0% 2.01 min: A: 95.0% B: 5.0% 2.50 min: A: 95.0% B: 5.0% | Positive |
| B | Solvent A: H$_2$O (0.1% formic acid) Solvent B: MeCN (0.1% formic acid) | 0.00 min: A: 95.0% B: 5.0% 1.00 min: A: 5.0%B: 95.0% 2.00 min: A: 5.0% B: 95.0% 2.01 min: A: 95.0% B: 5.0% 2.50 min: A:95.0% B:5.0% | Negative |
| C | Solvent A: H$_2$O (0.025% trifluoroacetic acid) Solvent B: MeCN (0.025% trifluoroacetic acid) | 0.00 min: A: 95.0% B: 5.0% 1.00 min: A: 5.0% B: 95.0% 2.00 min: A: 5.0% B: 95.0% 2.01 min: A: 95.0% B: 5.0% 2.50 min: A: 95.0% B: 5.0% | Positive |

LCMS Method D/E

Analytical HPLC was conducted on a X-Terra MS C18 column (3.5 µm 30×4.6 mm id) eluting with 0.01M ammonium acetate in water (solvent A) and 100% acetonitrile (solvent B), using the following elution gradient 0-4 minutes: 5% to 100% B, 4-5 minutes 100% B, at a flow rate of 1.4 ml/minute at 40° C.

The mass spectra (MS) were recorded on a Waters ZQ mass spectrometer using electrospray positive ionisation [ES+ to give MH$^+$ molecular ions] or electrospray negative ionisation [ES− to give (M-H)− molecular ions] modes. Cone voltage: 20V (method D) or 40V (method E).

LCMS Method F/G

| Method | Description |
|---|---|
| F | Column: Acquity BEH C18 (50 mm × 2.1 mm, 1.7 µm) Mobile Phase: A: 0.1% Formic acid in water; B: 0.1% Formic acid in MeCN Time (min)/% B: 0/3, 0.4/3, 3.2/98, 3.8/98, 4.2/3, 4.5/3 Column Temp: 35° C. Flow Rate: 0.6 mL/min |
| G | Column: X Bridge C18 (50 mm × 4.6 mm, 2.5 µm) Mobile Phase: A: 5 mM Ammonium bicarbonate in water (pH ~10): B: MeCN Time (min)/% B: 0/5, 0.5/5, 1/15, 3.3/98, 5.2/98, 5.5/5, 6/5. Column Temp: 35° C. Flow Rate: 1.3 mL/min |

Intermediate 1: 4-Chloro-5-methyl-2-nitrophenol

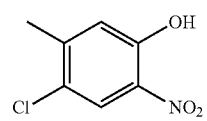

4-Chloro-3-methylphenol (500 g, 3.51 mol) was dissolved in acetic acid (2.5 L) at 10° C., then nitric acid (70%, 410 g, 4.56 mol) was added drop-wise and maintaining a temperature of <30° C. Once the addition was complete the mixture was stirred at between 20 and 30° C. for 1 h. After the completion of the reaction, the reaction mixture was filtered, the solid was carefully washed with acetic acid (200 mL) and water (500 mL), the solid was collected, and air dried to give 4-chloro-5-methyl-2-nitrophenol as a yellow solid (308 g, 47%).

$^1$H NMR (300 MHz, CDCl$_3$) δ 10.43 (s, 1H), 8.09 (s, 1H), 7.05 (s, 1H), 2.43 (s, 3H).

Intermediate 2: 2-Amino-4-chloro-5-methylphenol

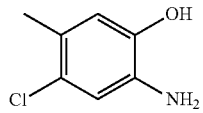

4-Chloro-5-methyl-2-nitrophenol (Intermediate 1, 150 g, 0.802 mol), iron trichloride (15 g, 10% wt), active carbon (15 g, 10% wt) in methanol (600 mL) and the reaction mixture was heated to 80° C. Hydrazine hydrate (80%, 502 g, 8.02 mol) was added drop-wise and the reaction mixture was stirred at 80° C. for 15 h. The reaction mixture was filtered, and the filtrated was collected, the solvent removed and the residue was dissolved in ethyl acetate (300 mL). The ethyl acetate was washed with water (200 mL), then with brine (200 mL×3) and dried over sodium sulphate. The solvent was removed to give 2-amino-4-chloro-5-methylphenol as a purple solid (100 g, 79%).

LCMS (A): Rt 1.32 min, MH$^+$ 158/160.

Intermediate 3: 5-Chloro-6-methylbenzo[d]oxazol-2(3H)-one

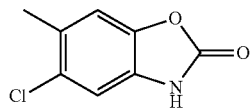

A mixture of 2-amino-4-chloro-5-methylphenol (Intermediate 2, 100 g, 0.637 mol), N,N'-carbonyldiimidazole (155 g, 0.955 mol) in THF (500 mL) was stirred at 66° C. for 1 h, the solvent was removed and the residue was diluted with water (1 L). The solid was isolated by filtration, dissolved in ethyl acetate (500 mL) and dried over sodium sulphate. The mixture was filtered and the filtrate and the solvent evaporated under reduced pressure to give 5-chloro-6-methylbenzo[d]oxazol-2(3H)-one as a yellow solid (100 g, 86%).

$^1$H NMR (300 MHz, d$_6$-DMSO) δ 11.73 (bs, 1H), 7.35 (s, 1H), 7.16 (s, 1H), 2.34 (s, 3H).

Intermediate 4: 4-Chloro-1-methoxy-2-nitrobenzene

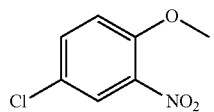

Sodium hydroxide (44.16 g, 1.104 mol) was dissolved in methanol (500 mL) and the methanol solution was added to 1,4-dichloro-2-nitrobenzene (100 g, 0.521 mol) in methanol at 70° C. After the addition the reaction mixture was stirred at 70° C. for 2 h, then was cooled and poured into water (3 L). The solid was isolated by filtration and washed with water (2 L) to give 4-chloro-1-methoxy-2-nitrobenzene as a pale-yellow solid (93 g, 95%).

$^1$H NMR (300 MHz, CDCl$_3$) δ 7.83 (d, J=2.4 Hz, 1H), 7.50 (dd, J=8.7 Hz, J=2.4 Hz, 1H), 7.03 (d, J=8.7 Hz, 1H), 3.95 (s, 3H).

Intermediate 5: 5-Chloro-2-methoxyaniline

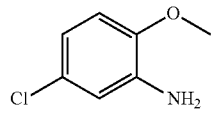

Hydrazine hydrate (80%, 186 g, 2.975 mol) was added drop-wise to a refluxing mixture of 4-chloro-1-methoxy-2-nitrobenzene (Intermediate 4, 93 g, 0.496 mol), iron trichloride (9.3 g, 10% wt) and active carbon (9.3 g, 10% wt) in methanol (1 L). After the addition, the reaction mixture was stirred at reflux for 16 h, the reaction mixture was filtered and the solvent evaporated from the filtrate under vacuum. The residue was washed with petroleum ether (2 L) to give 5-chloro-2-methoxyaniline as a white solid (76.7 g, 98%).

$^1$H NMR (300 MHz, CDCl$_3$) δ 6.67-6.65 (m, 3H), 3.83 (bs, 2H), 3.81 (s, 3H).

Intermediate 6: 4-Bromo-5-chloro-2-methoxyaniline

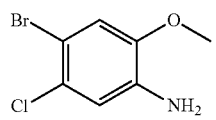

A mixture of 5-chloro-2-methoxyaniline (Intermediate 5, 76.7 g, 0.487 mol) in acetonitrile (500 mL) at 0° C. was treated with N-bromosuccinimide (86.7 g, 0.487 mol) added in portions over 2 h. After the addition, the solvent was removed and the residue purified by column chromatography (silica: 200-300 mesh, 200 g) eluting with petroleum ether/ethyl acetate from 20:1 to 4:1) to give 4-bromo-5-chloro-2-methoxyaniline as a light-yellow solid (40.2 g, 35%).

LCMS(A): Rt 1.63 min, MH$^+$ 236/238.

$^1$H NMR (300 MHz, CDCl$_3$) δ 6.93 (s, 1H), 6.78 (s, 1H), 3.83 (s, 3H).

Intermediate 7: 2-Amino-5-bromo-4-chlorophenol

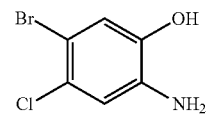

4-Bromo-5-chloro-2-methoxyaniline (Intermediate 6, 10 g, 42.3 mmol) in DCM (200 mL) was cooled to 0° C. Boron tribromide (21.2 g, 84.6 mmol) was added drop-wise over 30 min, the reaction mixture was stirred at 0° C. for 1 h and then at room temperature for 14 h. The reaction mixture was poured into ice water, sodium hydrogen carbonate was added until pH >7 and aqueous layer was extracted with ethyl acetate (300 mL×3). The organic phase was dried over magnesium sulphate and the solvent removed under vacuum to give 2-amino-5-bromo-4-chlorophenol as a red solid (8.4 g, 89%, used without further purification for the next step).

LCMS (A): Rt 1.46 min, MH$^+$ 222/224.

Intermediate 8: 6-Bromo-5-chlorobenzo[d]oxazol-2(3H)-one

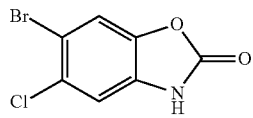

A mixture of 2-amino-5-bromo-4-chlorophenol (Intermediate 7, 8.4 g, 37.8 mmol), N,N-carbonyldiimidazole (12.2 g, 75.6 mmol) in THF (250 mL), was heated at 80° C. for 3 h. The solvent was removed under vacuum and the residue purified by column chromatography (silica: 200-400 mesh, 100 g) eluting with petroleum ether/ethyl acetate from 9:1 to 5:1) to give 6-bromo-5-chlorobenzo[d]oxazol-2(3H)-one as an orange solid (7.7 g, 82%).

LCMS (A): Rt 1.49 min, MH$^+$ 248/250.

Intermediate 9: Methyl 3-(6-bromo-5-chloro-2-oxobenzo[d]oxazol-3(2H)-yl)propanoate

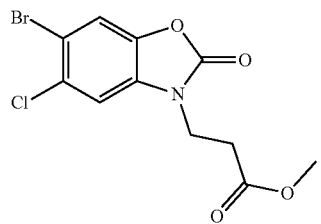 [SMILES: COC(=O)CCn1c(=O)oc2cc(Br)c(Cl)cc21]

A mixture of 6-bromo-5-chlorobenzo[d]oxazol-2(3H)-one (Intermediate 8, 7.7 g, 31 mmol), methyl 3-bromopropanoate (6.2 g, 37 mmol), potassium carbonate (8.5 g, 62 mmol) in acetonitrile (200 mL), was stirred at 70° C. for 16 h, the solvent was evaporated under vacuum, the residue purified by column chromatography (silica: 200-400 mesh, 50 g) eluting with petroleum ether/ethyl acetate 4:1 to give methyl 3-(6-bromo-5-chloro-2-oxobenzo[d]oxazol-3(2H)-yl)propanoate as an orange solid (6.2 g, 62%).

LCMS (A): Rt 1.66 min, MH$^+$=334/336.

Intermediate 10: Methyl 3-(5-chloro-2-oxo-6-(4,4,5,5-tetramethyl-1,3,2-dioxaborolan-2-yl)benzo[d]oxazol-3(2H)-yl)propanoate

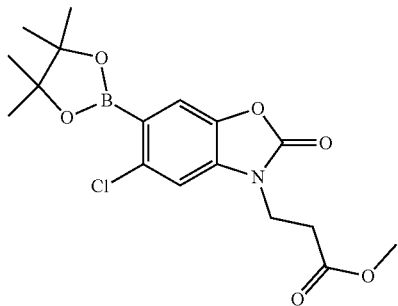

A mixture of methyl 3-(6-bromo-5-chloro-2-oxobenzo[d]oxazol-3(2H)-yl)propanoate (Intermediate 9, 5.2 g, 15.56 mmol), bis(pinacolato)diboron (11.8 g, 46.7 mmol), [1,1'-Bis(diphenylphosphino) ferrocene]dichloropalladium (11) (568 mg, 0.778 mmol), potassium acetate (3 g, 31.12 mmol) in 1,4-dioxane (500 mL) was stirred at 100° C. for 16 h under a nitrogen atmosphere. The solvent was evaporated under vacuum and the residue purified by column chromatography (silica: 200-300 mesh, 80 g) eluting with petroleum ether/ethyl acetate=9:1 then 8:1) to give methyl 3-(5-chloro-2-oxo-6-(4,4,5,5-tetramethyl-1,3,2-dioxaborolan-2-yl)benzo[d]oxazol-3(2H)-yl)propanoate as a yellow oil (5.2 g, 87%).

LCMS (A): Rt 1.73 min, MH$^+$ 382/384.

Intermediate 11: Methyl 3-(5-chloro-6-hydroxy-2-oxobenzo[d]oxazol-3(2H)-yl)propanoate

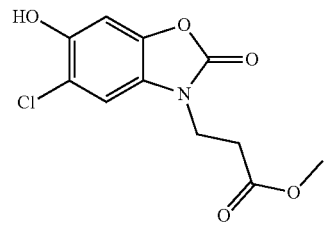 [SMILES: COC(=O)CCn1c(=O)oc2cc(O)c(Cl)cc21]

A mixture of methyl 3-(5-chloro-2-oxo-6-(4,4,5,5-tetramethyl-1,3,2-dioxaborolan-2-yl)benzo[d]oxazol-3(2H)-yl) propanoate (Intermediate 10, 5.2 g, 13.6 mmol) in hydrogen peroxide (30%, 12 mL), acetic acid (10 mL) and THF (100 mL) was stirred at room temperature for 16 h. Water was added, the mixture extracted with ethyl acetate (100 mL×3), the organic phase was dried over magnesium sulphate and the solvent evaporated under vacuum. The residue was purified by column chromatography (silica: 200-300 mesh, 50 g) eluting with petroleum ether/ethyl acetate=9:1, 8:1, 6:1, 4:1) to give methyl 3-(5-chloro-6-hydroxy-2-oxobenzo [d]oxazol-3(2H)-yl)propanoate as a yellow solid (2.5 g, 68%).

LCMS (A): Rt 1.32 min, MH$^+$ 272.

Intermediate 12: Methyl 3-(5-chloro-2-oxo-6-(1-(pyridin-2-yl)ethoxy)benzo[d]oxazol-3(2H)-yl)propanoate

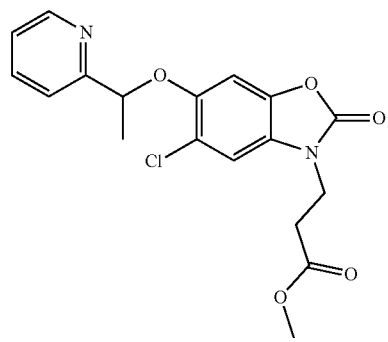 [SMILES: COC(=O)CCn1c(=O)oc2cc(OC(C)c3ccccn3)c(Cl)cc21]

1-(Pyridin-2-yl)ethanol (71 mg, 0.57 mmol), diethyl azodicarboxylate (84 mg, 0.48 mmol) and triphenylphosphine (126 mg, 0.48 mmol) were added to methyl 3-(5-chloro-6-hydroxy-2-oxobenzo[d]oxazol-3(2H)-yl)propanoate (Intermediate 11, 0.13 g, 0.48 mmol) in toluene (10 mL) and the reaction was stirred at room temperature for 2 days. The reaction mixture was poured into water (15 mL), aqueous layer was extracted with ethyl acetate (10 mL×3), combined organic layer and dried over sodium sulphate and partially purified by column chromatography [silica: 200-300 mesh, 10 g] eluting with petroleum ether/ethyl acetate=4:19 to give methyl 3-(5-chloro-2-oxo-6-(1-(pyridin-2-yl)ethoxy)benzo[d]oxazol-3(2H)-yl)propanoate as a white solid (270 mg, crude).

LCMS (A): Rt 1.57 min, MH+ 377.

Intermediate 13: (R)-Methyl 3-(5-chloro-2-oxo-6-(1-(pyridin-2-yl)ethoxy)benzo[d]oxazol-3(2H)-yl)propanoate

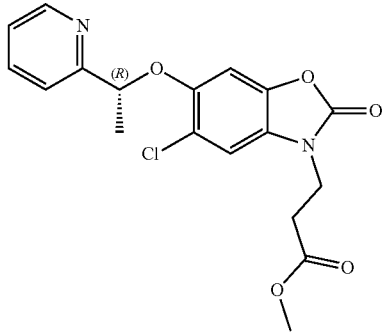

To methyl 3-(5-chloro-6-hydroxy-2-oxobenzo[d]oxazol-3(2H)-yl)propanoate (Intermediate 11, 133 mg, 0.49 mmol) in toluene (10 mL), was added (S)-1-(pyridin-2-yl)ethanol (60 mg, 0.49 mmol), triphenylphosphine (93 mg, 0.74 mmol), diethyl azodicarboxylate (129 mg, 0.74 mmol) and the reaction mixture was stirred at room temperature for 16 h. The solvent was removed and the residue was purified by column chromatography (silica: 200-300 mesh, 5 g) eluting with petroleum ether/ethyl acetate 5:1 to give (R)-methyl 3-(5-chloro-2-oxo-6-(1-(pyridin-2-yl)ethoxy)benzo[d]oxazol-3(2H)-yl)propanoate as a colourless oil (170 mg, 90%).

LCMS (A): Rt 1.40 min, MH+=377/379.

Intermediate 14: (S)-methyl 3-(5-chloro-2-oxo-6-(1-(pyridin-2-yl)ethoxy)benzo[d]oxazol-3(2H)-yl)propanoate

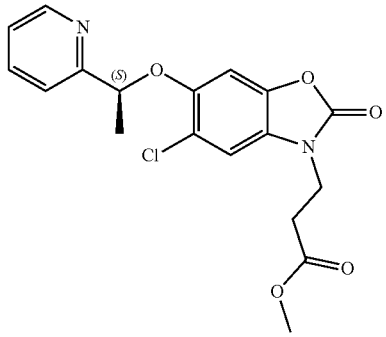

To methyl 3-(5-chloro-6-hydroxy-2-oxobenzo[d]oxazol-3(2H)-yl)propanoate (Intermediate 11, 133 mg, 0.49 mmol) in toluene (10 mL), was added (R)-1-(pyridin-2-yl)ethanol (60 mg, 0.49 mmol), triphenylphosphine (193 mg, 0.74 mmol), diethyl azodicarboxylate (129 mg, 0.74 mmol), the reaction mixture was stirred at room temperature for 16 h. The solvent was removed and the residue was purified by column chromatography (silica: 200-300 mesh, 5 g) eluting with petroleum ether/ethyl acetate 5:1) to give (S)-methyl 3-(5-chloro-2-oxo-6-(1-(pyridin-2-yl)ethoxy)benzo[d]oxazol-3(2H)-yl)propanoate as a colourless oil (160 mg, 86%).

LCMS (A): Rt 1.60 min, MH+=377/379.

Example 1: 3-(5-Chloro-6-methyl-2-oxobenzo[d]oxazol-3(2H)-yl)propanoic Acid

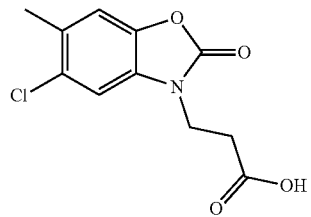 [SMILES: Cc1cc2oc(=O)n(CCC(=O)O)c2cc1Cl]

5-Chloro-6-methylbenzo[d]oxazol-2(3H)-one (Intermediate 3, 150 g, 0.82 mol), 3-bromopropanoic acid (251 g, 1.64 mol), potassium carbonate (226 g, 1.64 mol) were mixed in acetonitrile (2 L) and the reaction mixture stirred at 80° C. for 18 h. The reaction mixture was cooled to ambient temperature and filtered. The solid was collected and acidified to pH 4-5 with hydrochloric acid (3 N) and extracted with ethyl acetate (300 mL×5). The combined organic phases were dried over sodium sulphate, filtered, the filtrate was collected and the solvent evaporated to give 3-(5-chloro-6-methyl-2-oxobenzo[d]oxazol-3(2H)-yl)propanoic acid as a yellow solid (220 g). Used without further purification.

$^1$H NMR (300 MHz, d$_6$-DMSO) δ 12.43 (bs, 1H), 7.51 (s, 1H), 7.36 (s, 1H), 4.00 (t, J=6 Hz, 2H), 2.70 (t, J=6 Hz, 2H), 2.33 (s, 3H).

Example 1 (alternative preparation): 3-(5-Chloro-6-methyl-2-oxobenzo[d]oxazol-3(2H)-yl)propanoic Acid

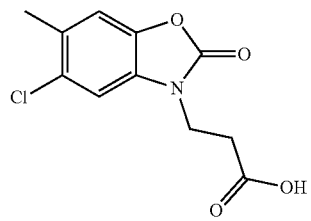 [SMILES: Cc1cc2oc(=O)n(CCC(=O)O)c2cc1Cl]

A mixture of 5-chloro-6-methylbenzo[d]oxazol-2(3H)-one (250 mg, 1.362 mmol, commercial), potassium carbonate (565 mg, 4.09 mmol) and 3-bromopropanoic acid (417 mg, 2.72 mmol) in acetonitrile (10 mL) was heated to 90° C. and stirred for 2 h. The mixture was cooled and filtered; the isolated white powder was washed with acetonitrile, suspended in water and acidified to pH 2 with hydrochloric acid (1N). The resulting solid was then triturated with hot acetonitrile, filtered and dried to give the 3-(5-chloro-6- methyl-2-oxobenzo[d]oxazol-3(2H)-yl)propanoic acid as a white powder (225 mg, 64.6%).

LCMS (E): Rt 2.29 min, [M-H]⁻ 254/256

Example 1a Tris Salt Formation: 3-(5-chloro-6-methyl-2-oxobenzo[d]oxazol-3(2H)-yl)propanoic acid, 2-Amino-2-(hydroxymethyl)-1,3-propanediol Salt

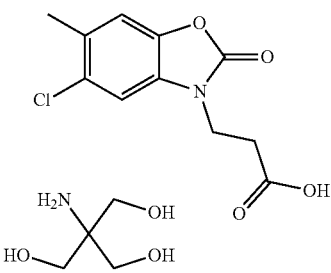 [SMILES: NC(CO)(CO)CO ; Cc1cc2oc(=O)n(CCC(=O)O)c2cc1Cl]

A mixture of 3-(5-chloro-6-methyl-2-oxobenzo[d]oxazol-3(2H)-yl) propanoic acid (Example 1, 220 g, 0.863 mol), 2-amino-2-(hydroxymethyl)propane-1,3-diol (104.5 g, 0.863 mol) in ethanol (4 L), was stirred at 80° C. for 2 h, the reaction mixture was filtered, the filtrate was collected and cooled to ambient temperature. The mixture was filtered, the solid was washed with ethanol (200 mL) and dried over air to give 3-(5-chloro-6-methyl-2-oxobenzo[d]oxazol-3(2H)-yl)propanoic acid, 2-amino-2-(hydroxymethyl)-1,3-propanediol salt as an off-white solid (150 g, 46%).

LCMS (A): Rt 1.41 min, MH⁺ 256/258.

¹H NMR (300 MHz, CD₃OD) δ 7.37 (s, 1H), 7.16 (s, 1H), 4.05 (t, J=6 Hz, 2H), 3.64 (s, 6H), 2.59 (t, J=6 Hz, 2H), 2.37 (s, 3H).

Example 2: 3-(5-chloro-2-oxo-6-(1-(pyridin-2-yl)ethoxy)benzo[d]oxazol-3(2H)-yl)propanoic acid, 2-Amino-2-(hydroxymethyl)-1,3-propanediol Salt

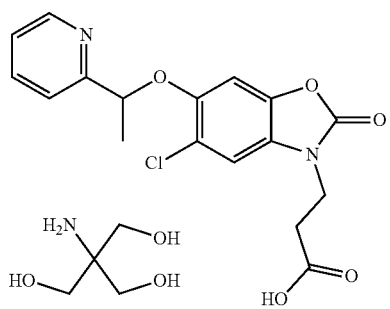 [SMILES: CC(Oc1cc2oc(=O)n(CCC(=O)O)c2cc1Cl)c1ccccn1 ; NC(CO)(CO)CO]

Methyl 3-(5-chloro-2-oxo-6-(1-(pyridin-2-yl)ethoxy)benzo[d]oxazol-3(2H)-yl)propanoate (Intermediate 12, 270 mg) in hydrochloric acid (0.5 N, 5 mL) was added to 1,4-dioxane (5 mL) and the reaction mixture was stirred at 80° C. for 3 h. The solvent was removed, the residue was purified by prep-HPLC [eluent: MeCN-water (0.1% TFA), gradient: 60-90% MeCN] to give 3-(5-chloro-2-oxo-6-(1-(pyridin-2-yl)ethoxy)benzo[d]oxazol-3(2H)-yl)propanoic acid as a yellow oil (30 mg, 0.08 mmol). Methanol (2 mL) and 2-amino-2-(hydroxymethyl)-1,3-propanediol (10 mg, 0.08 mmol) were added and the reaction mixture was stirred at room temperature for 30 minutes. The mixture was concentrated to give 3-(5-chloro-2-oxo-6-(1-(pyridin-2-yl)ethoxy)benzo[d]oxazol-3(2H)-yl)propanoic acid, 2-Amino-2-(hydroxymethyl)-1,3-propanediol salt as a yellow oil (40 mg, 17%).

LCMS (A): Rt 1.36 min, MH⁺ 363.

¹H NMR (300 MHz, CD₃OD) δ 8.52 (d, J=6 Hz, 1H), 7.82 (t, J=6 Hz, 1H), 7.57 (d, J=9 Hz, 1H), 7.41 (s, 1H), 7.35-7.31 (m, 1H), 6.91 (s, 1H), 5.44 (dd, J=12, 6 Hz, 2H), 4.02 (t, J=6 Hz, 2H), 3.66 (s, 6H), 2.62 (t, J=6 Hz, 2H), 1.69 (d, J=6 Hz, 3H).

Example 3: (R)-3-(5-chloro-2-oxo-6-(1-(pyridin-2-yl)ethoxy)benzo[d]oxazol-3(2H)-yl)propanoic Acid

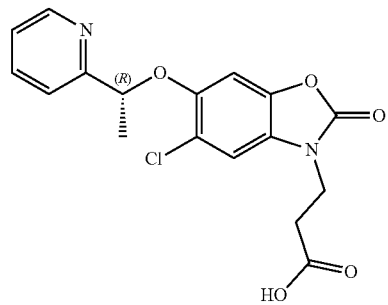

Hydrochloric acid (0.5 N, 4 mL) was added to a solution of (R)-methyl 3-(5-chloro-2-oxo-6-(1-(pyridin-2-yl)ethoxy)benzo[d]oxazol-3(2H)-yl)propanoate (Intermediate 13, 170 mg) in 1,4-dioxane (4 mL) and the reaction mixture was stirred at 80° C. for 16 h. The solvent was removed and the residue was purified by prep-HPLC (acetonitrile/water (0.1% TFA) 20:80 to 70:30). The solvent was removed and the residue was further purified by Super Critical Fluid Chromatography (hexane/ethanol 1:1, 0.2% TFA) to give (R)-3-(5-chloro-2-oxo-6-(1-(pyridin-2-yl)ethoxy)benzo[d]oxazol-3(2H)-yl)propanoic acid as a yellow oil (30 mg, 18%).

LCMS (A): Rt 1.37 min, MH⁺=363/365.

Example 3a (Tris salt formation): (R)-3-(5-chloro-2-oxo-6-(1-(pyridin-2-yl)ethoxy)benzo[d]oxazol-3(2H)-yl)propanoic Acid, 2-Amino-2-(hydroxymethyl)-1,3-propanediol Salt

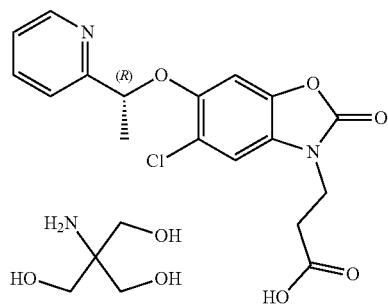

2-Amino-2-(hydroxymethyl)propane-1,3-diol (10 mg, 0.08 mol) was added to (R)-3-(5-chloro-2-oxo-6-(1-(pyridin-2-yl)ethoxy)benzo[d]oxazol-3(2H)-yl)propanoic acid (Example 3 (free acid), 30 mg, 0.08 mmol) in methanol (2 mL), the reaction mixture was stirred at ambient temperature for 30 min and the solvent removed under vacuum to give (R)-3-(5-chloro-2-oxo-6-(1-(pyridin-2-yl)ethoxy)benzo[d]oxazol-3(2H)-yl)propanoic acid, 2-Amino-2-(hydroxymethyl)-1,3-propanediol salt as a yellow oil (40 mg, 100%).

LCMS (A): Rt 1.38 min, MH$^+$=363/365.

$^1$H NMR (300 MHz, CD$_3$OD) δ 8.51 (d, J=3 Hz, 1H), 7.82 (td, J=9, 3 Hz, 1H), 7.57 (d, J=9 Hz, 1H), 7.42 (s, 1H), 7.34-7.33 (m, 1H), 6.91 (s, 1H), 5.43 (q, J=6 Hz, 1H), 4.02 (t, J=6 Hz, 2H), 3.66 (s, 6H), 2.59 (t, J=6 Hz, 2H), 1.69 (d, J=6 Hz, 3H).

Chiral-HPLC: 214 nm (100.0%), 254 nm (100.0%).

Example 4: (S)-3-(5-chloro-2-oxo-6-(1-(pyridin-2-yl)ethoxy)benzo[d]oxazol-3(2H)-yl)propanoic Acid

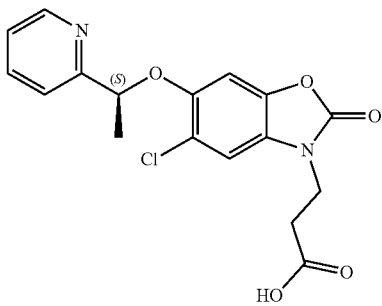

Hydrochloric acid (0.5 N, 4 mL) was added to (S)-methyl 3-(5-chloro-2-oxo-6-(1-(pyridin-2-yl)ethoxy)benzo[d]oxazol-3(2H)-yl)propanoate (Intermediate 14, 160 mg) in 1,4-dioxane (4 mL) and the reaction mixture was stirred at 80° C. for 16 h. The solvent was removed, the residue was purified with prep-HPLC (acetonitrile/water (0.1% TFA) 20:80 to 70:30). The solvent was removed, and the residue was further purified by Super Critical Fluid Chromatography (hexane/Ethanol 1:1, 0.2% TFA) to give (S)-3-(5-chloro-2-oxo-6-(1-(pyridin-2-yl)ethoxy)benzo[d]oxazol-3(2H)-yl) propanoic acid (23 mg, 5%).

LCMS (A): Rt 1.37 min, MH$^+$=363/365.

Chiral-HPLC: 214 nm (100.0%), 254 nm (100.0%).

Sodium hydroxide (44.16 g, 1.104 mol) was dissolved in methanol (500 mL) and the methanol solutions was added to 1,4-dichloro-2-nitrobenzene (100 g, 0.521 mol) in methanol at 70° C. After the addition the reaction mixture was stirred at 70° C. for 2 h, then was cooled and poured into water (3 L). The solid was isolated by filtration and washed with water (2 L) to give 4-chloro-1-methoxy-2-nitrobenzene as a pale-yellow solid (93 g, 95%).

Example 4a (Tris salt formation): (S)-3-(5-chloro-2-oxo-6-(1-(pyridin-2-yl)ethoxy)benzo[d]oxazol-3 (2H)-yl)propanoic Acid, 2-amino-2-(hydroxymethyl)-1,3-propanediol Salt

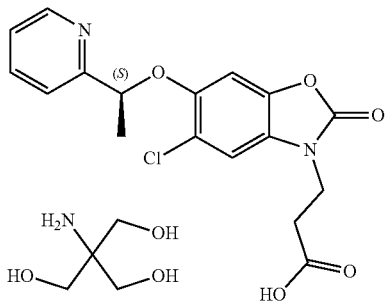

2-Amino-2-(hydroxymethyl)propane-1,3-diol (8 mg, 0.063 mol) was added to (S)-3-(5-chloro-2-oxo-6-(1-(pyridin-2-yl)ethoxy)benzo[d]oxazol-3(2H)-yl)propanoic acid (Example 4 (free acid), 23 mg, 0.063 mmol), in methanol (2 mL) and the reaction mixture was stirred at room temperature for 30 min. The solvent was removed and the residue was purified by prep-HPLC (acetonitrile/water (0.1% TFA) 20:80 to 70:30). After solvent removal, methanol (2 mL) and 2-amino-2-(hydroxymethyl)propane-1,3-diol (3 mg, 0.024 mmol) were added, the reaction mixture was stirred at room temperature for 30 min. Removal of solvent gave (S)-3-(5-chloro-2-oxo-6-(1-(pyridin-2-yl)ethoxy)benzo[d]oxazol-3 (2H)-yl)propanoic acid, 2-amino-2-(hydroxymethyl)-1,3-propanediol salt as a brown solid (10 mg, 13%).

LCMS (A): Rt 1.37 min, MH$^+$=363/365.

$^1$H NMR (300 MHz, CD$_3$OD) δ 8.51 (d, J=3 Hz, 1H), 7.82 (td, J=9, 3 Hz, 1H), 7.57 (d, J=9 Hz, 1H), 7.42 (s, 1H), 7.34-7.33 (m, 1H), 6.91 (s, 1H), 5.43 (q, J=6 Hz, 1H), 4.02 (t, J=6 Hz, 2H), 3.66 (s, 6H), 2.59 (t, J=6 Hz, 2H), 1.69 (d, J=6 Hz, 3H).

Chiral-HPLC: 214 nm (100.0%), 254 nm (100.0%).

$^1$H NMR (300 MHz, CDCl$_3$) δ 7.83 (d, J=2.4 Hz, 1H), 7.50 (dd, J=8.7 Hz, J=2.4 Hz, 1H), 7.03 (d, J=8.7 Hz, 1H), 3.95 (s, 3H).

Examples 5, 6, 8, 9, 11, and 25 were prepared in a manner substantially according to Scheme 1 or using methyl 3-(6-bromo-5-chloro-2-oxobenzo[d]oxazol-3(2H)-yl)propanoate (II). Examples 7, 10, 12-24 and 26-37 were prepared in a manner substantially similar to Example 2 according to Scheme 2.

TABLE 1

| Example no. | Structure | Name | Molecular ion | Rt (min) | LCMS method |
| --- | --- | --- | --- | --- | --- |
| 5 | ![structure] | 3-(5,6-dichloro-2-oxobenzo[d]oxazol-3(2H)-yl)propanoic acid | MH+ 276 | 2.02 | D |

TABLE 1-continued

| Example no. | Structure | Name | Molecular ion | Rt (min) | LCMS method |
|---|---|---|---|---|---|
| 6 | 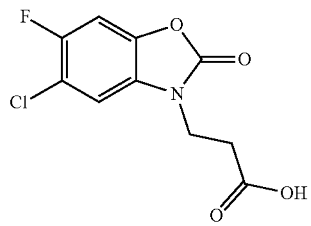 [SMILES: O=C(O)CCn1c(=O)oc2cc(F)c(Cl)cc21] | 3-(5-chloro-6-fluoro-2-oxobenzo[d]oxazol-3(2H)-yl)propanoic acid | MH+ 260 | 1.85 | D |
| 7 | 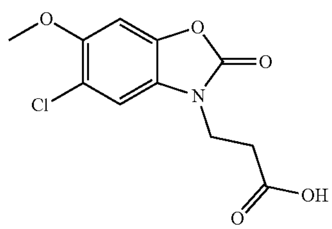 [SMILES: COc1cc2oc(=O)n(CCC(=O)O)c2cc1Cl] | 3-(5-chloro-6-methoxy-2-oxobenzo[d]oxazol-3(2H)-yl)propanoic acid | MH+ 272 | 1.37 | C |
| 8 | 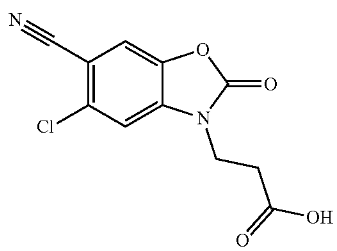 [SMILES: N#Cc1cc2oc(=O)n(CCC(=O)O)c2cc1Cl] | 3-(5-chloro-6-cyano-2-oxobenzo[d]oxazol-3(2H)-yl)propanoic acid | [M − H]− 265 | 1.38 | B |
| 9 | 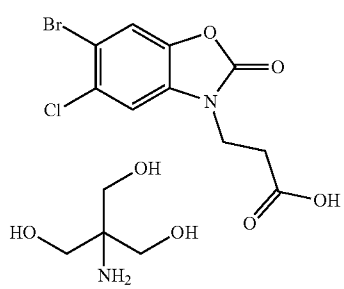 | 2-amino-2-(hydroxymethyl)propane-1,3-diol 3-(6-bromo-5-chloro-2-oxobenzo[d]oxazol-3(2H)-yl)propanoate | [M − H]− 318 | 1.46 | B |
| 10 | 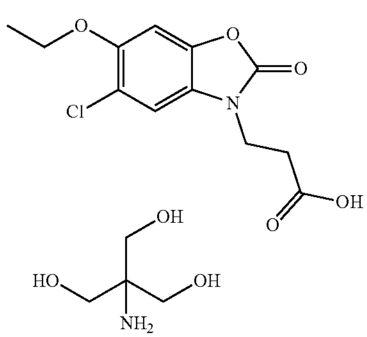 [SMILES: CCOc1cc2oc(=O)n(CCC(=O)O)c2cc1Cl ; NC(CO)(CO)CO] | 2-amino-2-(hydroxymethyl)propane-1,3-diol 3-(5-chloro-6-ethoxy-2-oxobenzo[d]oxazol-3(2H)-yl)propanoate | [M − H]− 284 | 1.43 | B |

TABLE 1-continued

| Example no. | Structure | Name | Molecular ion | Rt (min) | LCMS method |
|---|---|---|---|---|---|
| 11 | 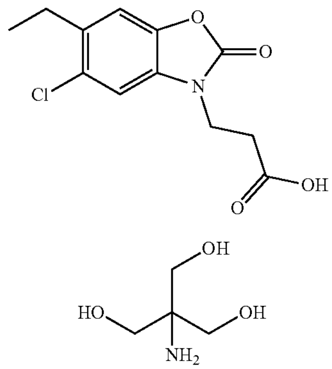 | 2-amino-2-(hydroxymethyl)propane-1,3-diol 3-(5-chloro-6-ethyl-2-oxobenzo[d]oxazol-3(2H)-yl)propanoate | [M − H]− 268 | 1.55 | B |
| 12 | 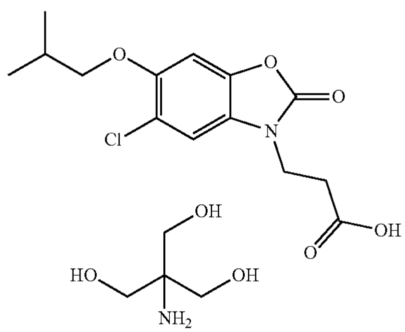 [SMILES: CC(C)COc1cc2oc(=O)n(CCC(=O)O)c2cc1Cl ; NC(CO)(CO)CO] | 2-amino-2-(hydroxymethyl)propane-1,3-diol 3-(5-chloro-6-isobutoxy-2-oxobenzo[d]oxazol-3(2H)-yl)propanoate | MH+ 314 | 2.48 | E |
| 13 | 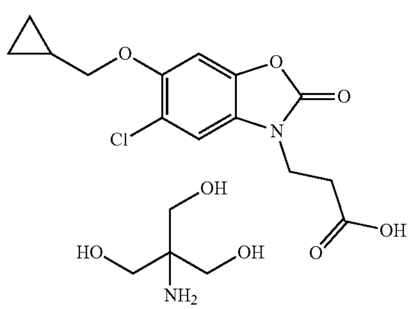 | 2-amino-2-(hydroxymethyl)propane-1,3-diol 3-(5-chloro-6-(cyclopropylmethoxy)-2-oxobenzo[d]oxazol-3(2H)-yl)propanoate | MH+ 312 | 1.51 | A |
| 14 | 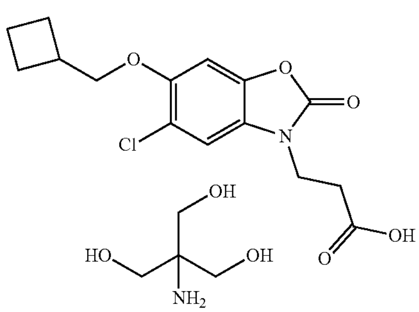 | 2-amino-2-(hydroxymethyl)propane-1,3-diol 3-(5-chloro-6-(cyclobutylmethoxy)-2-oxobenzo[d]oxazol-3(2H)-yl)propanoate | MH+ 326 | 1.57 | A |

TABLE 1-continued

| Example no. | Structure | Name | Molecular ion | Rt (min) | LCMS method |
|---|---|---|---|---|---|
| 15 | 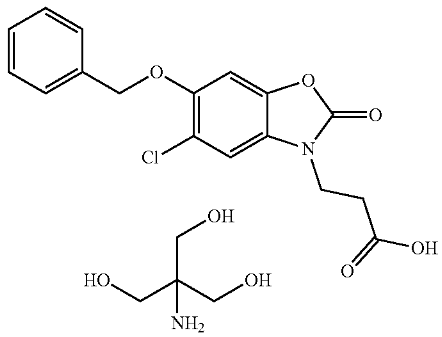 [SMILES: O=C(O)CCn1c(=O)oc2cc(OCc3ccccc3)c(Cl)cc21 ; NC(CO)(CO)CO] | 2-amino-2-(hydroxymethyl)propane-1,3-diol 3-(6-(benzyloxy)-5-chloro-2-oxobenzo[d]oxazol-3(2H)-yl)propanoate | MH+ 348 | 1.55 | A |
| 16 | 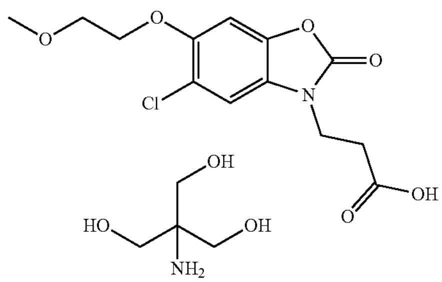 [SMILES: COCCOc1cc2oc(=O)n(CCC(=O)O)c2cc1Cl ; NC(CO)(CO)CO] | 2-amino-2-(hydroxymethyl)propane-1,3-diol 3-(5-chloro-6-(2-methoxyethoxy)-2-oxobenzo[d]oxazol-3(2H)-yl)propanoate | MH+ 316 | 1.40 | A |
| 17 | 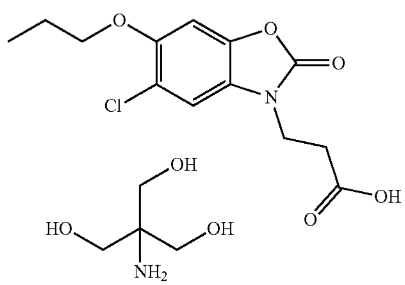 [SMILES: CCCOc1cc2oc(=O)n(CCC(=O)O)c2cc1Cl ; NC(CO)(CO)CO] | 2-amino-2-(hydroxymethyl)propane-1,3-diol 3-(5-chloro-2-oxo-6-propoxybenzo[d]oxazol-3(2H)-yl)propanoate | MH+ 300 | 2.29 | E |
| 18 | 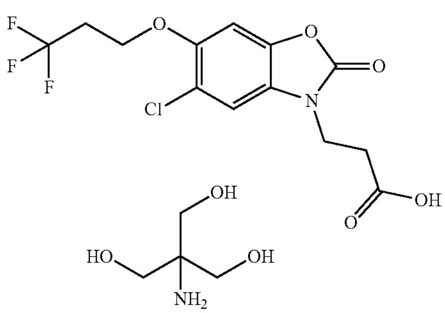 [SMILES: O=C(O)CCn1c(=O)oc2cc(OCCC(F)(F)F)c(Cl)cc21 ; NC(CO)(CO)CO] | 2-amino-2-(hydroxymethyl)propane-1,3-diol 3-(5-chloro-2-oxo-6-(3,3,3-trifluoropropoxy)benzo[d]oxazol-3(2H)-yl)propanoate | MH+ 354 | 1.47 | A |
| 19 | 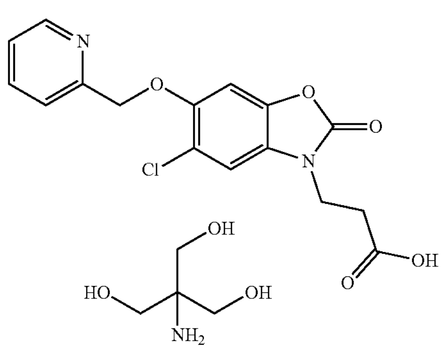 [SMILES: O=C(O)CCn1c(=O)oc2cc(OCc3ccccn3)c(Cl)cc21 ; NC(CO)(CO)CO] | 2-amino-2-(hydroxymethyl)propane-1,3-diol 3-(5-chloro-2-oxo-6-(pyridin-2-ylmethoxy)benzo[d]oxazol-3(2H)-yl)propanoate | MH+ 349 | 1.34 | A |

TABLE 1-continued

| Example no. | Structure | Name | Molecular ion | Rt (min) | LCMS method |
|---|---|---|---|---|---|
| 20 | 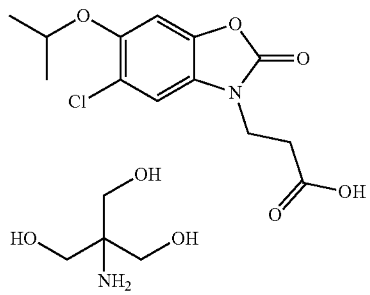 [SMILES: CC(C)Oc1cc2oc(=O)n(CCC(=O)O)c2cc1Cl ; NC(CO)(CO)CO] | 2-amino-2-(hydroxymethyl)propane-1,3-diol 3-(5-chloro-6-isopropoxy-2-oxobenzo[d]oxazol-3(2H)-yl)propanoate | MH+ 300 | 2.23 | E |
| 21 | 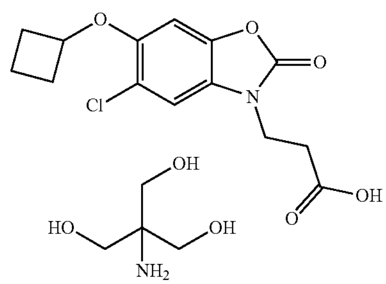 | 2-amino-2-(hydroxymethyl)propane-1,3-diol 3-(5-chloro-6-cyclobutoxy-2-oxobenzo[d]oxazol-3(2H)-yl)propanoate | [M − H]− 310 | 1.56 | B |
| 22 | 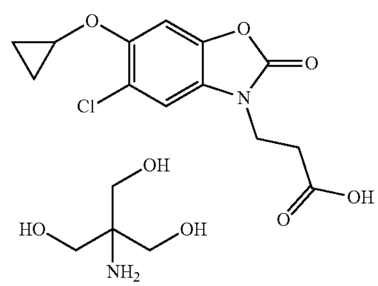 [SMILES: O=C(O)CCn1c(=O)oc2cc(OC3CC3)c(Cl)cc21 ; NC(CO)(CO)CO] | 2-amino-2-(hydroxymethyl)propane-1,3-diol 3-(5-chloro-6-cyclopropoxy-2-oxobenzo[d]oxazol-3(2H)-yl)propanoate | [M − H]− 296 | 1.51 | B |
| 23 | 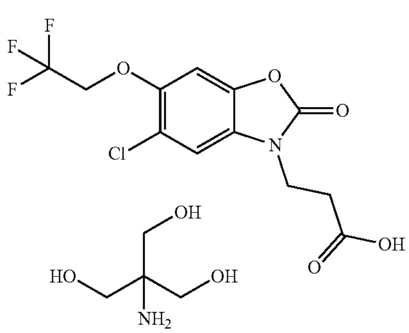 [SMILES: O=C(O)CCn1c(=O)oc2cc(OCC(F)(F)F)c(Cl)cc21 ; NC(CO)(CO)CO] | 2-amino-2-(hydroxymethyl)propane-1,3-diol 3-(5-chloro-2-oxo-6-(2,2,2-trifluoroethoxy)benzo[d]oxazol-3(2H)-yl)propanoate | MH+ 340 | 1.48 | A |
| 24 | 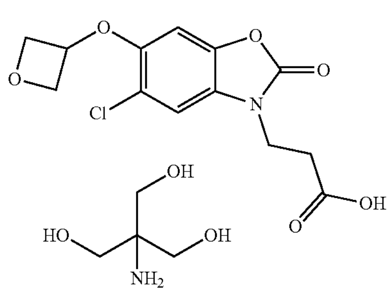 | 2-amino-2-(hydroxymethyl)propane-1,3-diol 3-(5-chloro-6-(oxetan-3-yloxy)-2-oxobenzo[d]oxazol-3(2H)-yl)propanoate | [M − H]− 312 | 1.28 | B |

TABLE 1-continued

| Example no. | Structure | Name | Molecular ion | Rt (min) | LCMS method |
|---|---|---|---|---|---|
| 25 | 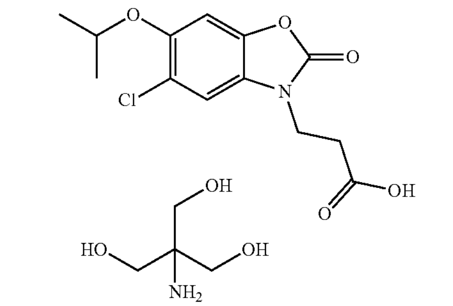 [SMILES: CC(C)Oc1cc2oc(=O)n(CCC(=O)O)c2cc1Cl ; NC(CO)(CO)CO] | 2-amino-2-(hydroxymethyl)propane-1,3-diol 3-(5-chloro-6-isobutyl-2-oxobenzo[d]oxazol-3(2H)-yl)propanoate | [M − H]− 296 | 1.64 | B |
| 26 | 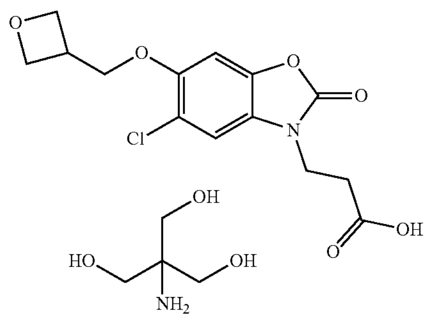 [SMILES: O=C(O)CCn1c(=O)oc2cc(OCC3COC3)c(Cl)cc21 ; NC(CO)(CO)CO] | 2-amino-2-(hydroxymethyl)propane-1,3-diol 3-(5-chloro-6-(oxetan-3-ylmethoxy)-2-oxobenzo[d]oxazol-3(2H)-yl)propanoate | [M − H]− 326 | 1.36 | B |
| 27 | 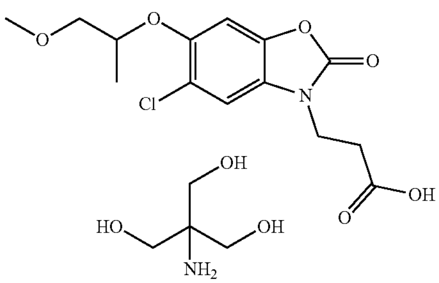 | 2-amino-2-(hydroxymethyl)propane-1,3-diol 3-(5-chloro-6-((1-methoxypropan-2-yl)oxy)-2-oxobenzo[d]oxazol-3(2H)-yl)propanoate | MH+ 330 | 1.42 | A |
| 28 | 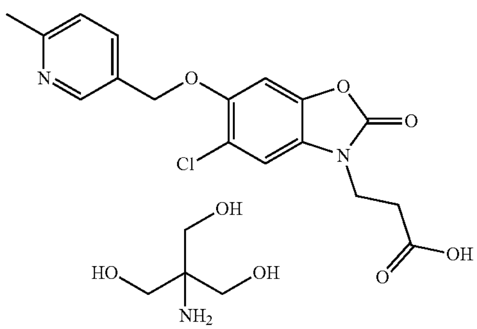 | 2-amino-2-(hydroxymethyl)propane-1,3-diol 3-(5-chloro-6-((6-methylpyridin-3-yl)methoxy)-2-oxobenzo[d]oxazol-3(2H)-yl)propanoate | MH+ 363 | 1.21 | A |
| 29 | 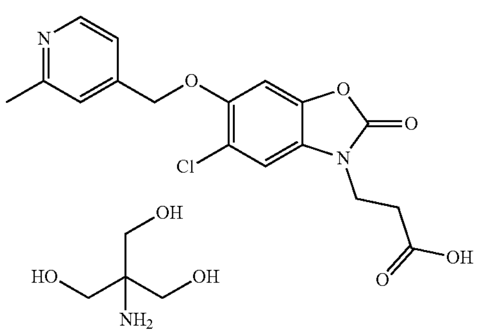 | 2-amino-2-(hydroxymethyl)propane-1,3-diol 3-(5-chloro-6-((2-methylpyridin-4-yl)methoxy)-2-oxobenzo[d]oxazol-3(2H)-yl)propanoate | MH+ 363 | 1.18 | A |

TABLE 1-continued

| Example no. | Structure | Name | Molecular ion | Rt (min) | LCMS method |
|---|---|---|---|---|---|
| 30 | 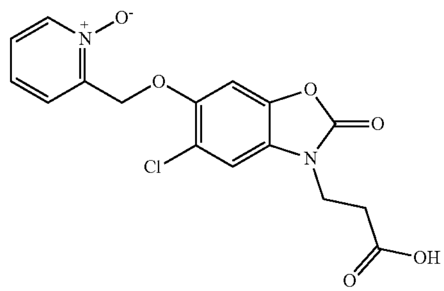 | 2-(((3-(2-carboxyethyl)-5-chloro-2-oxo-2,3-dihydrobenzo[d]oxazol-6-yl)oxy)methyl)pyridine 1-oxide | MH+ 365 | 1.30 | A |
| 31 | 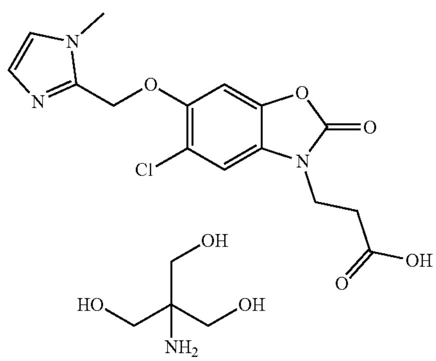 [SMILES: Cn1ccnc1COc1cc2oc(=O)n(CCC(=O)O)c2cc1Cl ; NC(CO)(CO)CO] | 2-amino-2-(hydroxymethyl)propane-1,3-diol 3-(5-chloro-6-((1-methyl-1H-imidazol-2-yl)methoxy)-2-oxobenzo[d]oxazol-3(2H)-yl)propanoate | MH+ 352 | 1.01 | A |
| 32 | 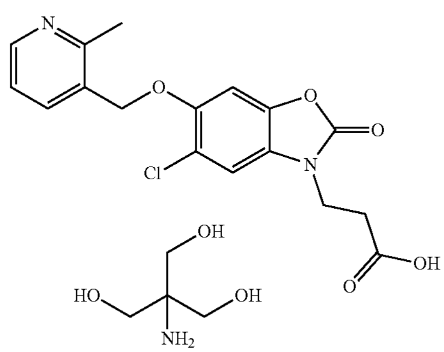 [SMILES: Cc1ncccc1COc1cc2oc(=O)n(CCC(=O)O)c2cc1Cl ; NC(CO)(CO)CO] | 2-amino-2-(hydroxymethyl)propane-1,3-diol 3-(5-chloro-6-((2-methylpyridin-3-yl)methoxy)-2-oxobenzo[d]oxazol-3(2H)-yl)propanoate | MH+ 363 | 1.23 | A |
| 33 | 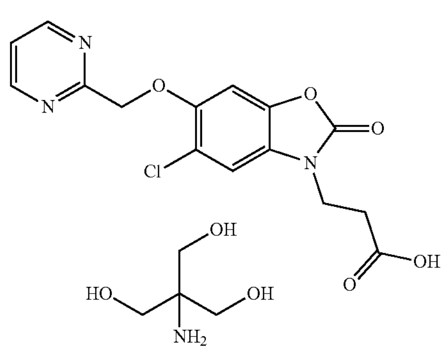 [SMILES: O=C(O)CCn1c(=O)oc2cc(OCc3ncccn3)c(Cl)cc21 ; NC(CO)(CO)CO] | 2-amino-2-(hydroxymethyl)propane-1,3-diol 3-(5-chloro-2-oxo-6-(pyrimidin-2-ylmethoxy)benzo[d]oxazol-3(2H)-yl)propanoate | MH+ 350 | 1.34 | A |

TABLE 1-continued

| Example no. | Structure | Name | Molecular ion | Rt (min) | LCMS method |
|---|---|---|---|---|---|
| 34 | 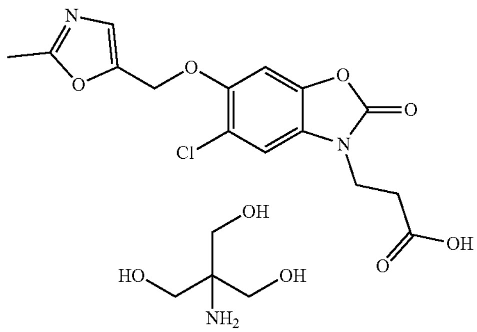 [SMILES: Cc1ncc(COc2cc3oc(=O)n(CCC(=O)O)c3cc2Cl)o1 ; NC(CO)(CO)CO] | 2-amino-2-(hydroxymethyl) propane-1,3-diol 3-(5-chloro-6-((2-methyloxazol-5-yl)methoxy)-2-oxobenzo[d]oxazol-3(2H)-yl)propanoate | MH+ 353 | 1.35 | A |
| 35 | 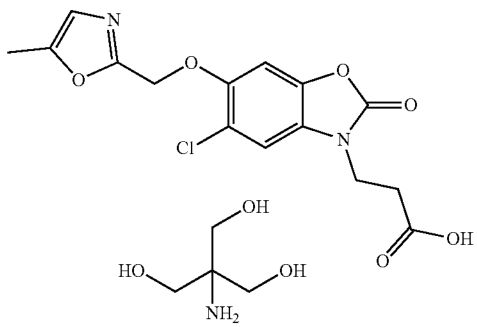 [SMILES: Cc1cnc(COc2cc3oc(=O)n(CCC(=O)O)c3cc2Cl)o1 ; NC(CO)(CO)CO] | 2-amino-2-(hydroxymethyl) propane-1,3-diol 3-(5-chloro-6-((5-methyloxazol-2-yl)methoxy)-2-oxobenzo[d]oxazol-3(2H)-yl)propanoate | MH+ 353 | 1.46 | A |
| 36 | 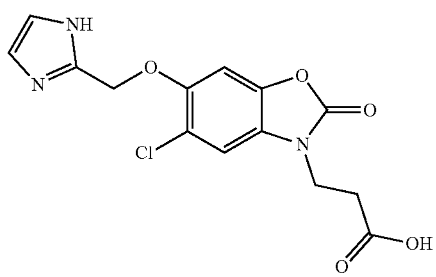 [SMILES: O=C(O)CCn1c(=O)oc2cc(OCc3ncc[nH]3)c(Cl)cc21] | 3-(6-((1H-imidazol-2-yl)methoxy)-5-chloro-2-oxobenzo[d]oxazol-3(2H)-yl)propanoic acid | MH+ 338 | 1.13 | A |
| 37 | 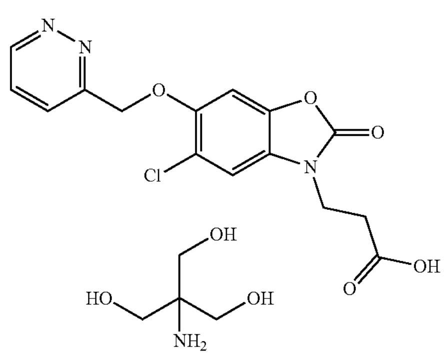 [SMILES: O=C(O)CCn1c(=O)oc2cc(OCc3cccnn3)c(Cl)cc21 ; NC(CO)(CO)CO] | 2-amino-2-(hydroxymethyl) propane-1,3-diol 3-(5-chloro-2-oxo-6-(pyridazin-3-ylmethoxy)benzo[d]oxazol-3(2H)-yl)propanoate | MH+ 350 | 1.50 | A |

Examples 3b-3l and 38-61 were prepared in a manner substantially according to Scheme 1 or using methyl 3-(6-bromo-5-chloro-2-oxobenzo[d]oxazol-3(2H)-yl)propanoate (11).

| Example no. | Structure | Name | Molecular ion | Rt (min) | LCMS method |
|---|---|---|---|---|---|
| 3b | 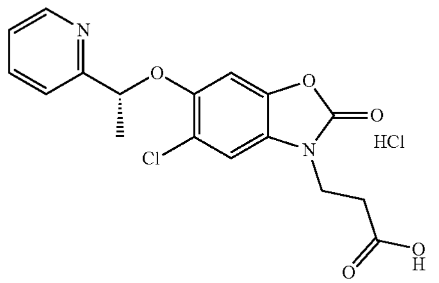 [SMILES: C[C@@H](Oc1cc2oc(=O)n(CCC(=O)O)c2cc1Cl)c1ccccn1 ; Cl] | (R)-3-(5-chloro-2-oxo-6-(1-(pyridin-2-yl)ethoxy)benzo[d]oxazol-3(2H)-yl)propanoic acid hydrochloride | MH+ 363 | 1.37 | A |
| 3c | 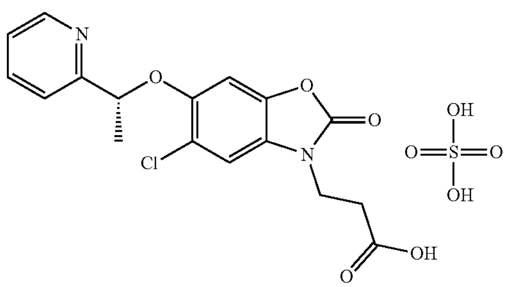 | (R)-3-(5-chloro-2-oxo-6-(1-(pyridin-2-yl)ethoxy)benzo[d]oxazol-3(2H)-yl)propanoic acid compound with sulfuric acid (1:1) | MH+ 363 | 1.38 | A |
| 3d | 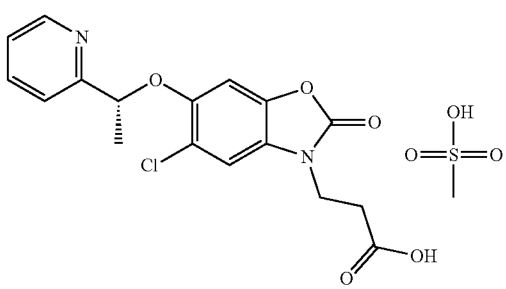 | (R)-3-(5-chloro-2-oxo-6-(1-(pyridin-2-yl)ethoxy)benzo[d]oxazol-3(2H)-yl)propanoic acid compound with methanesulfonic acid (1:1) | MH+ 363 | 1.38 | A |
| 3e | 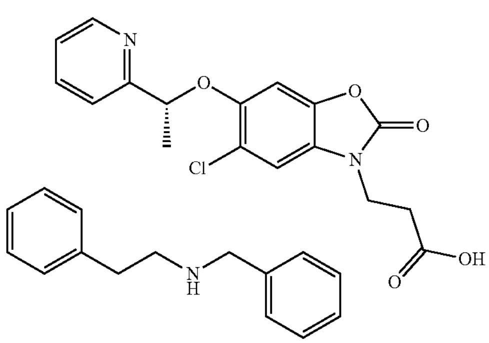 | N-benzyl-2-phenylethanamine (R)-3-(5-chloro-2-oxo-6-(1-(pyridin-2-yl)ethoxy)benzo[d]oxazol-3(2H)-yl)propanoate | MH+ 363 | 1.38 | A |

| Example no. | Structure | Name | Molecular ion | Rt (min) | LCMS method |
|---|---|---|---|---|---|
| 3f | 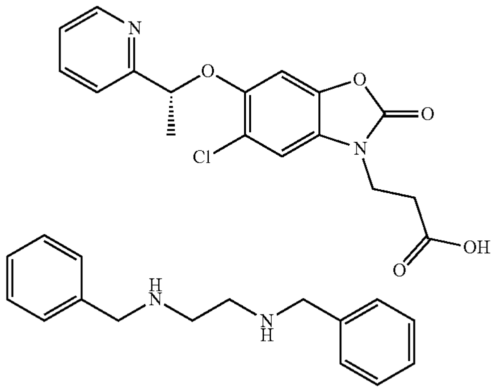 | N1,N2-dibenzylethane-1,2-diamine (R)-3-(5-chloro-2-oxo-6-(1-(pyridin-2-yl)ethoxy)benzo[d]oxazol-3(2H)-yl)propanoate | MH+ 363 | 1.37 | A |
| 3g | 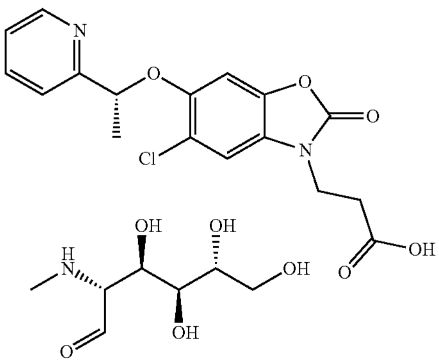 | (2R,3R,4S,5R)-3,4,5,6-tetrahydroxy-2-(methylamino)hexanal (R)-3-(5-chloro-2-oxo-6-(1-(pyridin-2-yl)ethoxy)benzo[d]oxazol-3(2H)-yl)propanoate | MH+ 363 | 1.45 | A |
| 3h | 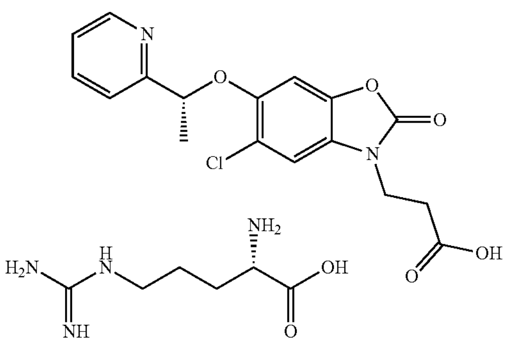 [SMILES: N=C(N)NCCC[C@H](N)C(=O)O ; C[C@@H](Oc1cc2oc(=O)n(CCC(=O)O)c2cc1Cl)c1ccccn1] | (R)-3-(5-chloro-2-oxo-6-(1-(pyridin-2-yl)ethoxy)benzo[d]oxazol-3(2H)-yl) propanoic acid compound with (S)-2-amino-5-guanidinopentanoic acid (1:1) | MH+ 363 | 1.38 | A |
| 3i | 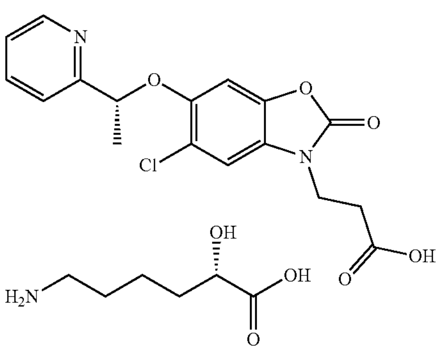 | (R)-3-(5-chloro-2-oxo-6-(1-(pyridin-2-yl)ethoxy)benzo[d]oxazol-3(2H)-yl)propanoic acid compound with (S)-2,6-diaminohexanoic acid (1:1) | MH+ 363 | 1.38 | A |

| Example no. | Structure | Name | Molecular ion | Rt (min) | LCMS method |
|---|---|---|---|---|---|
| 3j | 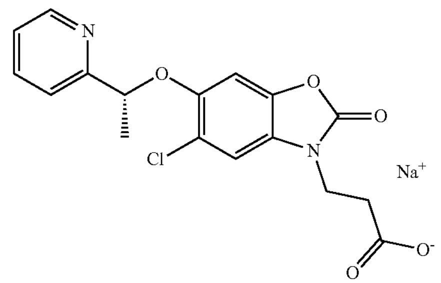 [SMILES: C[C@@H](Oc1cc2oc(=O)n(CCC(=O)[O-])c2cc1Cl)c1ccccn1 ; [Na+]] | sodium (R)-3-(5-chloro-2-oxo-6-(1-(pyridin-2-yl)ethoxy)benzo[d]oxazol-3(2H)-yl)propanoate | MH+ 363 | 1.37 | A |
| 3k | 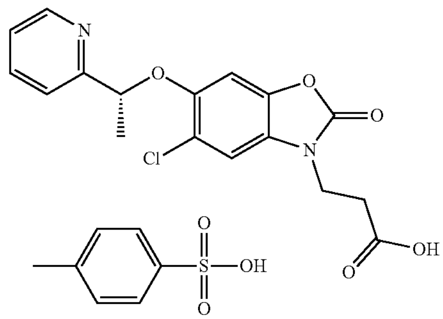 [SMILES: C[C@@H](Oc1cc2oc(=O)n(CCC(=O)O)c2cc1Cl)c1ccccn1 ; Cc1ccc(S(=O)(=O)O)cc1] | (R)-3-(5-chloro-2-oxo-6-(1-(pyridin-2-yl)ethoxy)benzo[d]oxazol-3(2H)-yl)propanoic acid compound with 4-methylbenzenesulfonic acid (1:1) | MH+ 363 | 1.36 | A |
| 3l | 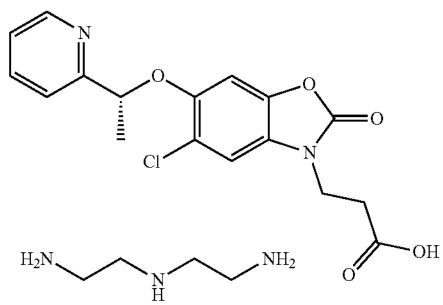 [SMILES: C[C@@H](Oc1cc2oc(=O)n(CCC(=O)O)c2cc1Cl)c1ccccn1 ; NCCNCCN] | N1-(2-aminoethyl)ethane-1,2-diamine (R)-3-(5-chloro-2-oxo-6-(1-(pyridin-2-yl)ethoxy)benzo[d]oxazol-3(2H)-yl)propanoate | MH+ 363 | 1.38 | A |
| 38 | 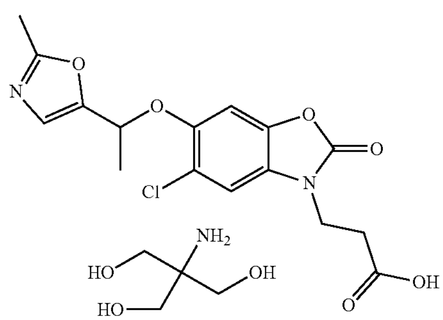 | 2-amino-2-(hydroxymethyl)propane-1,3-diol 3-(5-chloro-6-(1-(2-methyloxazol-5-yl)ethoxy)-2-oxobenzo[d]oxazol-3(2H)-yl)propanoate (racemic) | MH+ 367 | 1.44 | A |
| 39 | 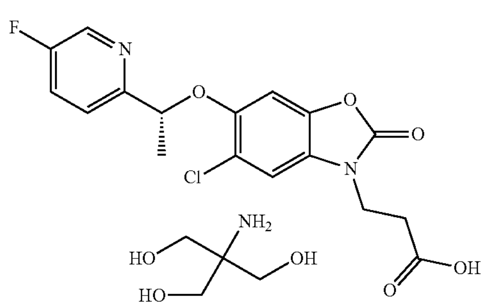 | 2-amino-2-(hydroxymethyl)propane-1,3-diol (R)-3-(5-chloro-6-(1-(5-fluoropyridin-2-yl)ethoxy)-2-oxobenzo[d]oxazol-3(2H)-yl)propanoate | MH+ 381 | 1.45 | A |

| Example no. | Structure | Name | Molecular ion | Rt (min) | LCMS method |
|---|---|---|---|---|---|
| 40 | 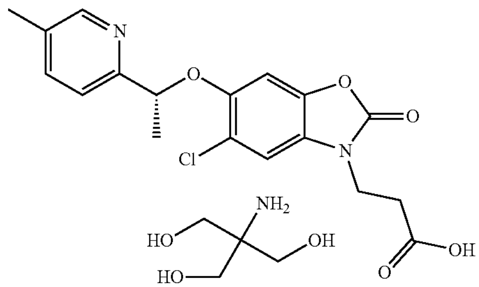 | 2-amino-2-(hydroxymethyl)propane-1,3-diol (R)-3-(5-chloro-6-(1-(5-methylpyridin-2-yl)ethoxy)-2-oxobenzo[d]oxazol-3(2H)-yl)propanoate | MH+ 377 | 1.49 | A |
| 40a | 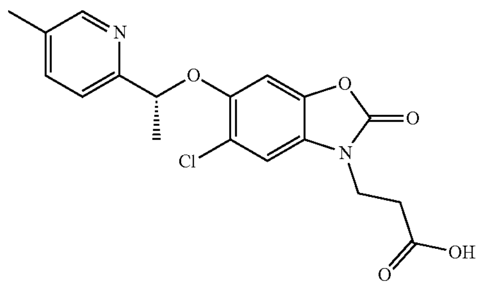 [SMILES: Cc1ccc([C@@H](C)Oc2cc3oc(=O)n(CCC(=O)O)c3cc2Cl)nc1] | (R)-3-(5-chloro-6-(1-(5-methylpyridin-2-yl)ethoxy)-2-oxobenzo[d]oxazol-3(2H)-yl)propanoic acid | MH+ 377 | 1.40 | A |
| 41 | 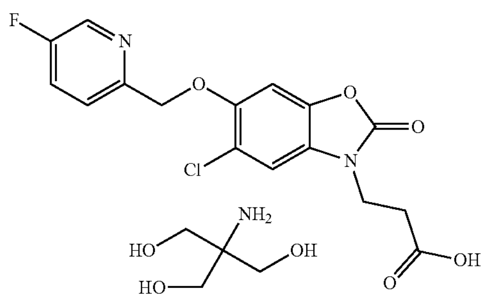 | 2-amino-2-(hydroxymethyl)propane-1,3-diol 3-(5-chloro-6-((5-fluoropyridin-2-yl)methoxy)-2-oxobenzo[d]oxazol-3(2H)-yl)propanoate | MH+ 367 | 1.50 | A |
| 42 | 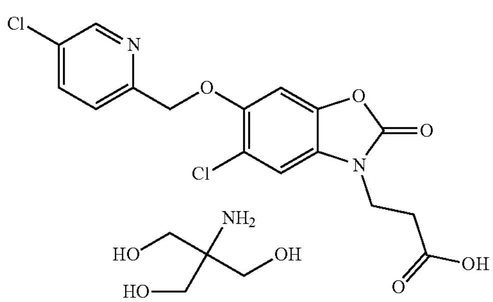 | 2-amino-2-(hydroxymethyl)propane-1,3-diol 3-(5-chloro-6-((5-chloropyridin-2-yl)methoxy)-2-oxobenzo[d]oxazol-3(2H)-yl)propanoate | MH+ 383 | 1.49 | A |
| 43 | 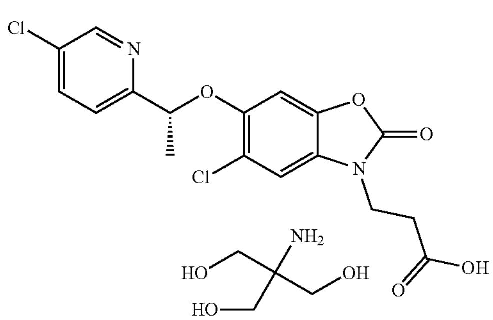 | 2-amino-2-(hydroxymethyl)propane-1,3-diol (R)-3-(5-chloro-6-(1-(5-chloropyridin-2-yl)ethoxy)-2-oxobenzo[d]oxazol-3(2H)-yl)propanoate | MH+ 397 | 1.54 | A |

| Example no. | Structure | Name | Molecular ion | Rt (min) | LCMS method |
|---|---|---|---|---|---|
| 43a | Chiral | (R)-3-(5-chloro-6-(1-(5-chloropyridin-2-yl)ethoxy)-2-oxobenzo[d]oxazol-3(2H)-yl)propanoic acid | MH+ 397 | 1.58 | A |
| 44 | 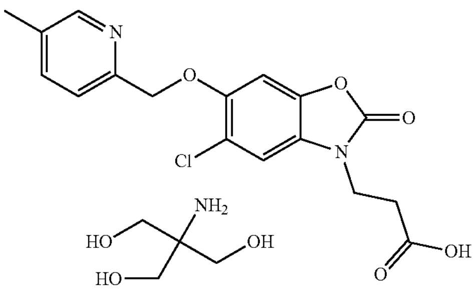 | 2-amino-2-(hydroxymethyl)propane-1,3-diol 3-(5-chloro-6-((5-methylpyridin-2-yl)methoxy)-2-oxobenzo[d]oxazol-3(2H)-yl)propanoate | MH+ 363 | 1.35 | A |
| 45 | 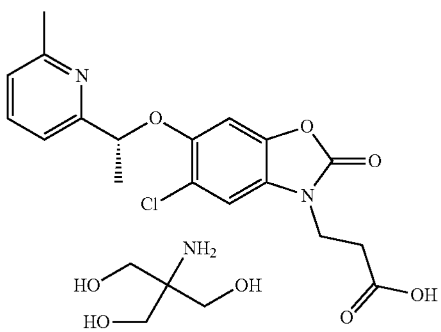 | 2-amino-2-(hydroxymethyl)propane-1,3-diol (R)-3-(5-chloro-6-(1-(6-methylpyridin-2-yl)ethoxy)-2-oxobenzo[d]oxazol-3(2H)-yl)propanoate | MH+ 377 | 1.35 | A |
| 46 | 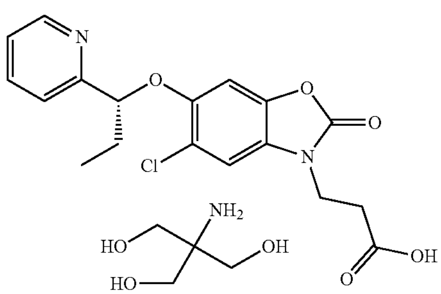 | 2-amino-2-(hydroxymethyl)propane-1,3-diol (R)-3-(5-chloro-2-oxo-6-(1-(pyridin-2-yl)propoxy)benzo[d]oxazol-3(2H)-yl)propanoate | MH+ 377 | 1.44 | A |
| 46a | 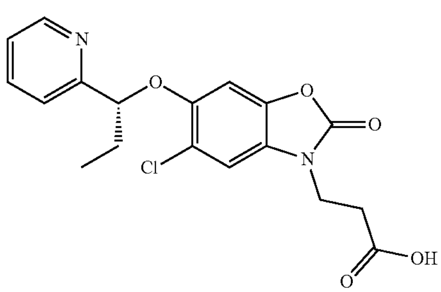 [SMILES: CC[C@@H](Oc1cc2oc(=O)n(CCC(=O)O)c2cc1Cl)c1ccccn1] | (R)-3-(5-chloro-2-oxo-6-(1-(pyridin-2-yl)propoxy)benzo[d]oxazol-3(2H)-yl)propanoic acid | MH+ 377 | 1.44 | A |

| Example no. | Structure | Name | Molecular ion | Rt (min) | LCMS method |
|---|---|---|---|---|---|
| 47 | 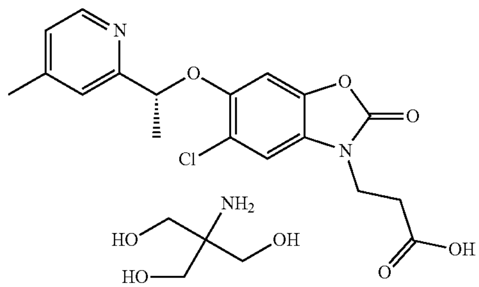 | 2-amino-2-(hydroxymethyl)propane-1,3-diol (R)-3-(5-chloro-6-(1-(4-methylpyridin-2-yl)ethoxy)-2-oxobenzo[d]oxazol-3(2H)-yl)propanoate | MH+ 377 | 1.33 | A |
| 48 | 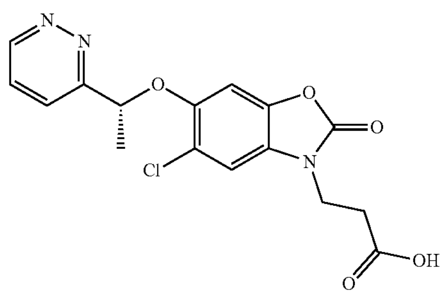 [SMILES: C[C@@H](Oc1cc2oc(=O)n(CCC(=O)O)c2cc1Cl)c1cccnn1] | (R)-3-(5-chloro-2-oxo-6-(1-(pyridazin-3-yl)ethoxy)benzo[d]oxazol-3(2H)-yl)propanoic acid | MH+ 364 | 1.37 | A |
| 49 | 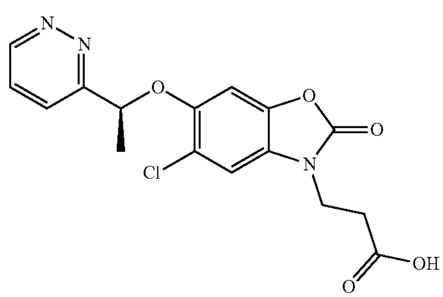 [SMILES: C[C@H](Oc1cc2oc(=O)n(CCC(=O)O)c2cc1Cl)c1cccnn1] | (S)-3-(5-chloro-2-oxo-6-(1-(pyridazin-3-yl)ethoxy)benzo[d]oxazol-3(2H)-yl)propanoic acid | MH+ 364 | 1.36 | A |
| 50 | 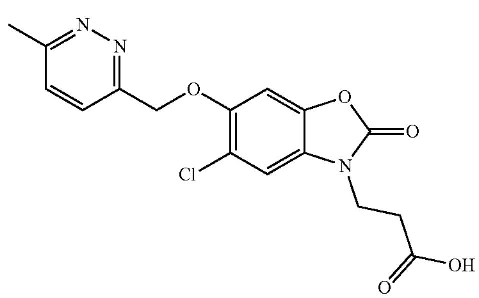 [SMILES: Cc1ccc(COc2cc3oc(=O)n(CCC(=O)O)c3cc2Cl)nn1] | 3-(5-chloro-6-((6-methylpyridazin-3-yl)methoxy)-2-oxobenzo[d]oxazol-3(2H)-yl)propanoic acid | MH+ 364 | 1.50 | A |
| 51 | 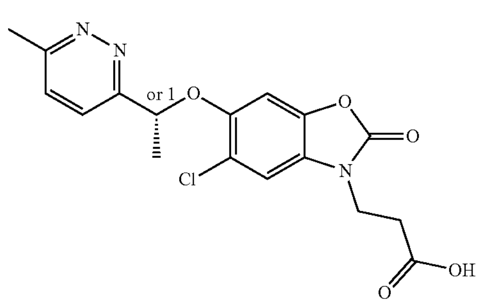 [SMILES: Cc1ccc([C@@H](C)Oc2cc3oc(=O)n(CCC(=O)O)c3cc2Cl)nn1] | 3-(5-chloro-6-(1-(6-methylpyridazin-3-yl)ethoxy)-2-oxobenzo[d]oxazol-3(2H)-yl)propanoic acid (single unknown enantiomer) | MH+ 378 | 1.30 | A |

| Example no. | Structure | Name | Molecular ion | Rt (min) | LCMS method |
|---|---|---|---|---|---|
| 52 | 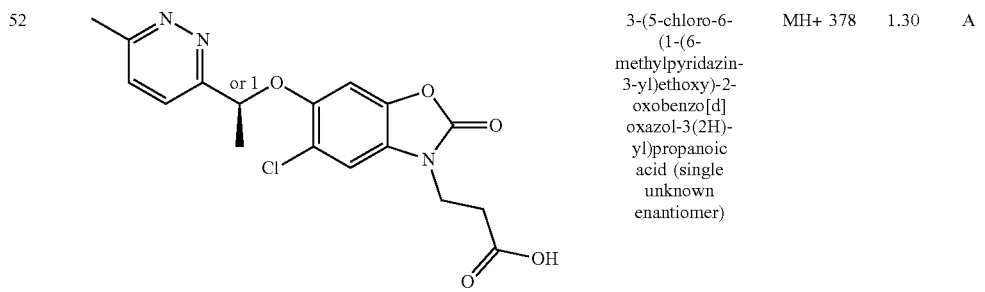 ISOMER 2 | 3-(5-chloro-6-(1-(6-methylpyridazin-3-yl)ethoxy)-2-oxobenzo[d]oxazol-3(2H)-yl)propanoic acid (single unknown enantiomer) | MH+ 378 | 1.30 | A |
| 53 | 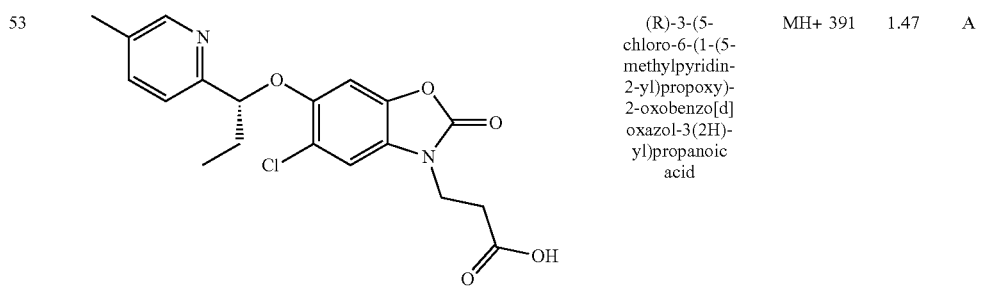 | (R)-3-(5-chloro-6-(1-(5-methylpyridin-2-yl)propoxy)-2-oxobenzo[d]oxazol-3(2H)-yl)propanoic acid | MH+ 391 | 1.47 | A |
| 54 | 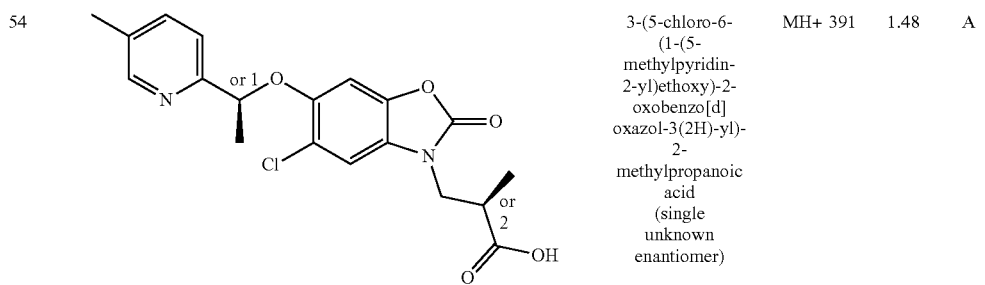 ISOMER 1 | 3-(5-chloro-6-(1-(5-methylpyridin-2-yl)ethoxy)-2-oxobenzo[d]oxazol-3(2H)-yl)-2-methylpropanoic acid (single unknown enantiomer) | MH+ 391 | 1.48 | A |
| 55 | 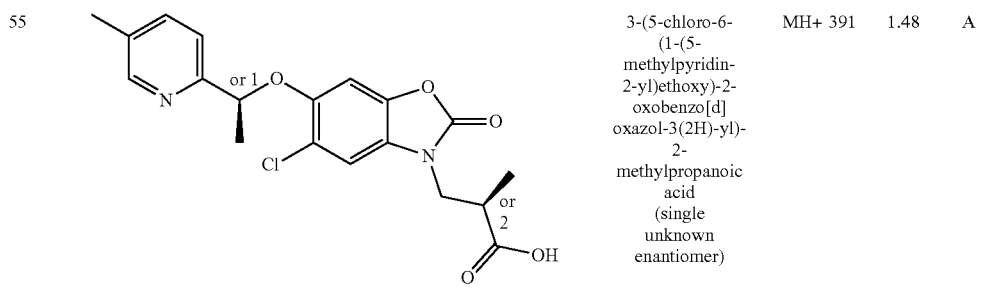 ISOMER 2 | 3-(5-chloro-6-(1-(5-methylpyridin-2-yl)ethoxy)-2-oxobenzo[d]oxazol-3(2H)-yl)-2-methylpropanoic acid (single unknown enantiomer) | MH+ 391 | 1.48 | A |

| Example no. | Structure | Name | Molecular ion | Rt (min) | LCMS method |
|---|---|---|---|---|---|
| 56 | ISOMER 3 | 3-(5-chloro-6-(1-(5-methylpyridin-2-yl)ethoxy)-2-oxobenzo[d]oxazol-3(2H)-yl)-2-methylpropanoic acid (single unknown enantiomer) | MH+ 391 | 1.48 | A |
| 57 | ISOMER 4 | 3-(5-chloro-6-(1-(5-methylpyridin-2-yl)ethoxy)-2-oxobenzo[d]oxazol-3(2H)-yl)-2-methylpropanoic acid (single unknown enantiomer) | MH+ 391 | 1.48 | A |
| 58 | ISOMER 1 | 2-amino-2-(hydroxymethyl)propane-1,3-diol 3-(5-chloro-2-oxo-6-(1-(pyrimidin-2-yl)ethoxy)benzo[d]oxazol-3(2H)-yl)propanoate (single unknown enantiomer) | MH+ 364 | 2.55 | G |
| 59 | ISOMER 2 | 2-amino-2-(hydroxymethyl)propane-1,3-diol 3-(5-chloro-2-oxo-6-(1-(pyrimidin-2-yl)ethoxy)benzo[d]oxazol-3(2H)-yl)propanoate (single unknown enantiomer) | [M − H]⁻ 362 | 1.71 | F |

| Example no. | Structure | Name | Molecular ion | Rt (min) | LCMS method |
|---|---|---|---|---|---|
| 60 | 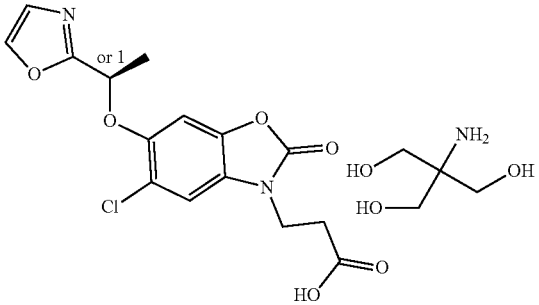<br>ISOMER 1 | 2-amino-2-(hydroxymethyl)propane-1,3-diol 3-(5-chloro-6-(1-(oxazol-2-yl)ethoxy)-2-oxobenzo[d]oxazol-3(2H)-yl)propanoate | [M − H]⁻ 351 | 1.83 | F |
| 61 | 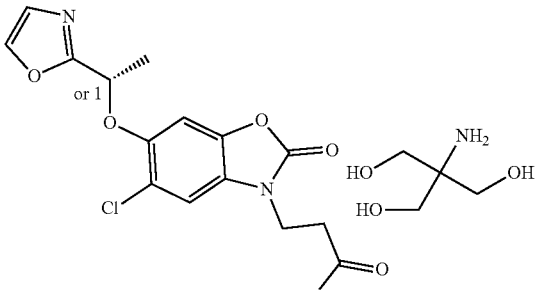<br>ISOMER 2 | 2-amino-2-(hydroxymethyl)propane-1,3-diol 3-(5-chloro-6-(1-(oxazol-2-yl)ethoxy)-2-oxobenzo[d]oxazol-3(2H)-yl)propanoate | [M − H]⁻ 351 | 1.83 | F |

The potencies and efficacies of the compounds of the invention for KMO inhibition can be determined by MS Rapidfire assay performed on the human cloned enzyme as described herein. Compounds of formula (I) have demonstrated inhibitory activity at the KMO enzyme, using the MS Rapidfire functional assay described herein.

KMO MS Rapidfire Assay Protocol
Materials and Methods
Materials

L-Kynurenine (Kyn), 3-hydroxy-DL-kynurenine (3-HK), β-Nicotinamide adenine dinucleotide 2′-phosphate reduced tetrasodium salt hydrate (NADPH), 4-(2-hydroxyethyl)piperazine-1-ethanesulfonic acid (Hepes), DL-dithiothreitol (DTT), ethylenediaminetetraacetic acid (EDTA), CHAPS and trifluoroacetic acid (TFA) were purchased from Sigma-Aldrich Ltd. (Gillingham, Dorset, UK). HPLC-grade acetonitrile and formic acid were supplied by Fisher Scientific (Loughborough, UK).

Cloning and Expression of Human KMO

Full length human KMO was amplified by PCR from pcDNA5/FRT/V5-His-TOPO/hKMO (vector supplied by the University of Edinburgh) and cloned into pGEX6P-1 (GE Healthcare) using BamH1 and SaiI restriction sites. DNA encoding the N-terminal Glutathione-S-transferase (GST) tag, followed by a Pre-Scission protease cleavage site, and the full length KMO was amplified by PCR from pGEX6P-1-KMO and cloned into pFastbac1 (Invitrogen) using XbaI and EcoR1 restriction sites.

pFastbac1 GST-KMO was transposed into the baculovirus genome using the BAC-to-BAC technology (Invitrogen) and bacmid DNA was prepared and transfected into Spodoptera frugiperda (Sf9) cells using Cellfectin II (Invitrogen). Expression of a protein of the expected molecular weight (Mr 82,634) was seen by Western blot analysis using anti-GST-peroxidase conjugate.

Preparation of membranes from Sf9 cells expressing Human GST-KMO A P1 virus stock was generated from a single clone and used to infect 3×1.5 L cultures of Sf9 cells in 3 L Corning Fernbach flasks. The Sf9 cells were grown in Hyclone SFX media (Thermo Scientific) to about 3×10⁶ cells/ml and were infected at a nominal multiplicity of infection of 3. Cells were harvested after 48 hours and disrupted by blending in 50 mM Hepes, pH 7.4, 1 mM EDTA buffer containing protease inhibitors. A low speed spin (400 g) was used to remove cell debris, followed by a high speed spin (75 000 g) to pellet the membranes. The membranes were purified in a discontinuous sucrose density gradient by re-suspending in 10% (w/v) sucrose and layering over 40% (w/v) sucrose, both in the above buffer. This was centrifuged at 150 000 g and the purified membranes were taken from the interface, collected by centrifugation at 100 000 g, resuspended in buffer and aliquoted for storage at −80° C. KMO activity was found to be associated with the membrane fraction only and no KMO activity was detected in membranes prepared from uninfected Sf9 cells. A batch of 104 mg of purified Sf9 KMO-membranes (as determined by the Pierce BCA protein assay using bovine serum albumin as standard) was prepared and validated in the RF MS assay.

RapidFire High-Throughput Mass Spectrometry Assay 11 point, 3-fold serial dilutions of test compounds were prepared in DMSO and 100 nL of these solutions were dispensed into 384-well V-base polypropylene plates (Greiner Bio-one, Stonehouse, UK) using an Echo 555 acoustic dispenser (Labcyte, Sunnyvale, Calif.). This gave a final assay concentration range between 100 μM and 1.7 nM in 10 μL final assay volume (see below). 100 nL DMSO was dispensed into columns 6 and 18 for high and low controls, respectively, with prior inactivation of the enzyme in column 18 by pre-dispense of 30 µL of 0.5% (v/v) TFA.

Conditions for the assay of human KMO using isolated KMO-membranes were 50 mM Hepes, pH 7.5, 2 mM DTT, 1 mM EDTA, 100 µM CHAPS, 200 µM NADPH, 10 µM Kynurenine and 8 µg/ml KMO-membranes in a total reaction volume of 10 µL.

Assays were performed by initially dispensing 5 µL of a 2× Enzyme solution (16 µg/ml KMO-membranes in 50 mM Hepes, pH 7.5, 2 mM DTT, 2 mM EDTA, 200 µM CHAPS) into plates containing 100 nL compounds and incubating for 10 min at ambient temperature. Reactions were initiated by addition of 5 µL of 2× Substrate solution (400 µM NADPH, 20 µM Kynurenine in 50 mM Hepes, pH 7.5, 2 mM DTT) and incubated for 2 h at room temperature before quenching the reaction with 30 µL of 0.5% (v/v) TFA. Plates were centrifuged at 2500 rpm for 10 min before analysis. All additions were made using a Multidrop Combi dispenser (Thermo Fisher Scientific).

Quenched assay plates were transferred to a high-throughput RapidFire200 integrated autosampler/solid-phase extraction (SPE) system (Agilent Technologies, Wakefield, Mass.). Samples were aspirated from each well for 500 ms and 10 µL was loaded directly onto a RapidFire micro-scale SPE C18 (type C) cartridge, which was washed for 3 s with HPLC-grade water containing 0.1% (v/v) formic acid to remove non-organic components. Analytes were then eluted into the mass spectrometer, in a 3 s elution cycle, using 80% (v/v) acetonitrile/water containing 0.1% (v/v) formic acid, and the cartridge was then equilibrated by washing with water containing 0.1% (v/v) formic acid for 500 ms. This gave a total cycle time of 7 s, enabling analysis of a 384-well plate in approximately 45 min.

Both Kyn and 3-HK were detected using a Sciex API4000 triple quadrupole mass spectrometer (Applied Biosystems, Concord, Ontario, Canada), equipped with an electrospray interface and operated in positive ion mode. Multiple reaction monitoring (MRM) was used to detect both Kyn and 3-HK using Q1/Q3 transitions at m/z 209.4 to 192.0 and m/z 225.3 to 208.2, respectively. The mass spectrometer used an ESI voltage of 5500 V and a source temperature of 600° C., with a dwell time of 50 ms for each transition.

Data Analysis

Individual MRM transitions were saved as text files and the extracted ion chromatograms were integrated and processed using the RapidFire® peak integration software (version 3.6).

Using the integrated peak area for 3-HK data was analysed within ActivityBase (ID Business Solutions Ltd, Surrey, UK). Dose response curves were fitted to equation (1):

$$\text{Inhibition (\%)} = \frac{(a-d)}{1+\left(\frac{[I]}{IC_{50}}\right)^S} + d \qquad (1)$$

Where a is the uninhibited response, d is the fully inhibited response, [I] is the inhibitor concentration, $IC_{50}$ is [I] that gives 0.5×(a–d) and S is the Hill slope.

Exemplified compounds of the invention have median $pIC_{50}$ values of >6.1 in the above MS Rapidfire assay. Example 1 has a median $pIC_{50}$=7.9 in the above MS Rapidfire assay. Example 2 has a median $pIC_{50}$=8.4 in the above MS Rapidfire assay.

The invention claimed is:

1. A compound of Formula (I):

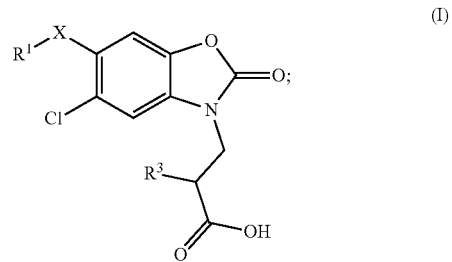

wherein:
X is a bond and $R^1$ is —CN;
X is —O— and $R^1$ is —$(CH_2)_mCF_3$, —$CHR^2CH_2OMe$, —$(CH_2)_nC_{3-4}$cycloalkyl, —$(CH_2)_n$oxetane, -benzyl or —$CHR^2$heteroaryl;
wherein:
the heteroaryl as defined in —$CHR^2$ heteroaryl may be additionally substituted by halo, methyl, ethyl or 0;
m=1 or 2;
n=0 or 1;
$R^2$=—H, methyl or -ethyl;
$R^3$=H or -methyl; or
a pharmaceutically acceptable salt thereof;
provided that:
the compound of Formula (I) is not:
3-(5-chloro-2-oxobenzo[d]oxazol-3(2H)-yl)propanoic acid;
3-(5-chloro-2-oxobenzo[d]oxazol-3(2H)-yl)-2-methylpropanoic acid; or a
pharmaceutically acceptable salt thereof, provided that the compound of Formula I is not 3-(5-chloro-6-methyl-2-oxobenzo[d]oxazol-3(2H)-yl)propanoic acid.

2. The compound of Formula (I) or a pharmaceutically acceptable salt thereof according to claim 1, wherein X is —O— and $R^1$— is $(CH_2)_mCF_3$, —$CHR^2CH_2OMe$, —$(CH_2)_nC_{3-4}$cycloalkyl, —$(CH_2)_n$oxetane, -benzyl or —$CHR^2$heteroaryl; wherein heteroaryl may be additionally substituted by methyl or 0.

3. The compound of Formula (I) or a pharmaceutically acceptable salt thereof according to claim 2, wherein X is –0- and $R^1$ is —$CHR^2$heteroaryl.

4. A compound which is:
3-(5-chloro-2-oxo-6-(1-(pyridin-2-yl)ethoxy)benzo[d]oxazol-3(2H)-yl)propanoic acid;
(R)-3-(5-chloro-2-oxo-6-(1-(pyridin-2-yl)ethoxy)benzo[d]oxazol-3(2H)-yl)propanoic acid;
(S)-3-(5-chloro-2-oxo-6-(1-(pyridin-2-yl)ethoxy)benzo[d]oxazol-3(2H)-yl)propanoic acid;
3-(5-chloro-6-cyano-2-oxobenzo[d]oxazol-3(2H)-yl)propanoic acid;
3-(5-chloro-6-(cyclopropylmethoxy)-2-oxobenzo[d]oxazol-3(2H)-yl)propanoic acid;
3-(5-chloro-6-(cyclobutylmethoxy)-2-oxobenzo[d]oxazol-3(2H)-yl)propanoic acid;
3-(6-(benzyloxy)-5-chloro-2-oxobenzo[d]oxazol-3(2H)-yl)propanoic acid;
3-(5-chloro-6-(2-methoxyethoxy)-2-oxobenzo[d]oxazol-3(2H)-yl)propanoic acid;
3-(5-chloro-2-oxo-6-(3,3,3-trifluoropropoxy)benzo[d]oxazol-3(2H)-yl)propanoic acid;
3-(5-chloro-2-oxo-6-(pyridin-2-ylmethoxy)benzo[d]oxazol-3(2H)-yl)propanoic acid;

3-(5-chloro-6-cyclobutoxy-2-oxobenzo[d]oxazol-3(2H)-yl)propanoic acid;
3-(5-chloro-6-cyclopropoxy-2-oxobenzo[d]oxazol-3(2H)-yl)propanoic acid;
3-(5-chloro-2-oxo-6-(2,2,2-trifluoroethoxy)benzo[d]oxazol-3(2H)-yl)propanoic acid;
3-(5-chloro-6-(oxetan-3-yloxy)-2-oxobenzo[d]oxazol-3(2H)-yl)propanoic acid;
3-(5-chloro-6-(oxetan-3-ylmethoxy)-2-oxobenzo[d]oxazol-3(2H)-yl)propanoic acid;
3-(5-chloro-6-((1-methoxypropan-2-yl)oxy)-2-oxobenzo[d]oxazol-3(2H)-yl)propanoic acid;
3-(5-chloro-6-((6-methylpyridin-3-yl)methoxy)-2-oxobenzo[d]oxazol-3(2H)-yl)propanoic acid;
3-(5-chloro-6-((2-methylpyridin-4-yl)methoxy)-2-oxobenzo[d]oxazol-3(2H)-yl)propanoic acid;
2-(((3-(2-carboxyethyl)-5-chloro-2-oxo-2,3-dihydrobenzo[d]oxazol-6-yl)oxy)methyl)pyridine 1-oxide;
3-(5-chloro-6-((1-methyl-1H-imidazol-2-yl)methoxy)-2-oxobenzo[d]oxazol-3(2H)-yl)propanoic acid;
3-(5-chloro-6-((2-methylpyridin-3-yl)methoxy)-2-oxobenzo[d]oxazol-3(2H)-yl)propanoic acid;
3-(5-chloro-2-oxo-6-(pyrimidin-2-ylmethoxy)benzo[d]oxazol-3(2H)-yl)propanoic acid;
3-(5-chloro-6-((2-methyloxazol-5-yl)methoxy)-2-oxobenzo[d]oxazol-3(2H)-yl)propanoic acid;
3-(5-chloro-6-((5-methyloxazol-2-yl)methoxy)-2-oxobenzo[d]oxazol-3(2H)-yl)propanoic acid;
3-(6-((1H-imidazol-2-yl)methoxy)-5-chloro-2-oxobenzo[d]oxazol-3(2H)-yl)propanoic acid; and
3-(5-chloro-2-oxo-6-(pyridazin-3-ylmethoxy)benzo[d]oxazol-3(2H)-yl)propanoic acid;
(R)-3-(5-chloro-2-oxo-6-(1-(pyridin-2-yl)ethoxy)benzo[d]oxazol-3(2H)-yl)propanoic acid;
3-(5-chloro-6-(1-(2-methyloxazol-5-yl)ethoxy)-2-oxobenzo[d]oxazol-3(2H)-yl)propanoic acid (racemic);
(R)-3-(5-chloro-6-(1-(5-fluoropyridin-2-yl)ethoxy)-2-oxobenzo[d]oxazol-3(2H)-yl)propanoic acid;
(R)-3-(5-chloro-6-(1-(5-methylpyridin-2-yl)ethoxy)-2-oxobenzo[d]oxazol-3(2H)-yl)propanoic acid;
3-(5-chloro-6-((5-fluoropyridin-2-yl)methoxy)-2-oxobenzo[d]oxazol-3(2H)-yl)propanoic acid;
3-(5-chloro-6-((5-chloropyridin-2-yl)methoxy)-2-oxobenzo[d]oxazol-3(2H)-yl)propanoic acid;
(R)-3-(5-chloro-6-(1-(5-chloropyridin-2-yl)ethoxy)-2-oxobenzo[d]oxazol-3(2H)-yl)propanoic acid;
3-(5-chloro-6-((5-methylpyridin-2-yl)methoxy)-2-oxobenzo[d]oxazol-3(2H)-yl)propanoic acid;
(R)-3-(5-chloro-6-(1-(6-methylpyridin-2-yl)ethoxy)-2-oxobenzo[d]oxazol-3(2H)-yl)propanoic acid;
(R)-3-(5-chloro-2-oxo-6-(1-(pyridin-2-yl)propoxy)benzo[d]oxazol-3(2H)-yl)propanoic acid;
(R)-3-(5-chloro-6-(1-(4-methylpyridin-2-yl)ethoxy)-2-oxobenzo[d]oxazol-3(2H)-yl)propanoic acid;
(R)-3-(5-chloro-2-oxo-6-(1-(pyridazin-3-yl)ethoxy)benzo[d]oxazol-3(2H)-yl)propanoic acid;
(S)-3-(5-chloro-2-oxo-6-(1-(pyridazin-3-yl)ethoxy)benzo[d]oxazol-3(2H)-yl)propanoic acid;
3-(5-chloro-6-((6-methylpyridazin-3-yl)methoxy)-2-oxobenzo[d]oxazol-3(2H)-yl)propanoic acid;
(S)-3-(5-chloro-6-(1-(6-methylpyridazin-3-yl)ethoxy)-2-oxobenzo[d]oxazol-3(2H)-yl)propanoic acid;
(R)-3-(5-chloro-6-(1-(6-methylpyridazin-3-yl)ethoxy)-2-oxobenzo[d]oxazol-3(2H)-yl)propanoic acid;
(R)-3-(5-chloro-6-(1-(5-methylpyridin-2-yl)propoxy)-2-oxobenzo[d]oxazol-3(2H)-yl)propanoic acid;
(S)-3-(5-chloro-6-(1-(5-methylpyridin-2-yl)ethoxy)-2-oxobenzo[d]oxazol-3(2H)-yl)-2-methylpropanoic acid;
(R)-3-(5-chloro-6-(1-(5-methylpyridin-2-yl)ethoxy)-2-oxobenzo[d]oxazol-3(2H)-yl)-2-methylpropanoic acid;
(S)-3-(5-chloro-6-(1-(5-methylpyridin-2-yl)ethoxy)-2-oxobenzo[d]oxazol-3(2H)-yl)-2-methylpropanoic acid;
(R)-3-(5-chloro-6-(1-(5-methylpyridin-2-yl)ethoxy)-2-oxobenzo[d]oxazol-3(2H)-yl)-2-methylpropanoic acid;
3-(5-chloro-2-oxo-6-(1-(pyrimidin-2-yl)ethoxy)benzo[d]oxazol-3(2H)-yl)propanoic acid;
(S)-3-(5-chloro-6-(1-(oxazol-2-yl)ethoxy)-2-oxobenzo[d]oxazol-3(2H)-yl)propanoic acid; and
(R)-3-(5-chloro-6-(1-(oxazol-2-yl)ethoxy)-2-oxobenzo[d]oxazol-3(2H)-yl)propanoic acid;
or a pharmaceutically acceptable salt thereof.

5. A pharmaceutical composition comprising: a) a compound Formula (I) according to claim 1:

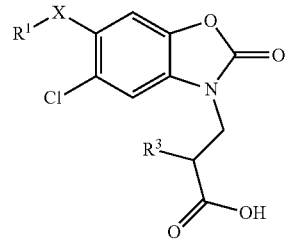

wherein:
X is a bond and $R^1$ is —CN;
$R^3$=H or -methyl; or
a pharmaceutically acceptable salt thereof; and
b) one or more pharmaceutically acceptable excipients.

6. A method of treatment of acute pancreatitis, which comprises administering—a compound of Formula (I) or a pharmaceutically acceptable salt thereof according to claim 1 to a subject in need thereof.

7. A method of treatment of acute pancreatitis, which comprises administering—a pharmaceutical composition according to claim 5 to a subject in need thereof.

* * * * *

UNITED STATES PATENT AND TRADEMARK OFFICE
CERTIFICATE OF CORRECTION

PATENT NO. : 11,352,334 B2
APPLICATION NO. : 16/521283
DATED : June 7, 2022
INVENTOR(S) : Anne Marie Jeanne Bouillot et al.

It is certified that error appears in the above-identified patent and that said Letters Patent is hereby corrected as shown below:

In the Claims

Claim 1, Column 72, Line 23 reads:
"the heteroaryl as defined in -CHR2heteroaryl may be additionally substituted by halo, methyl, ethyl or 0;"

Whereas it should read:
-- the heteroaryl as defined in -CHR2heteroaryl may be additionally substituted by halo, methyl, ethyl or O; --

Claim 2, Column 72, Line 43 reads:
"wherein heteroaryl may be additionally substituted by methyl or 0;"

Whereas it should read:
-- wherein heteroaryl may be additionally substituted by methyl or O; --

Claim 3, Column 72, Line 46 reads:
"wherein X is –0- and R1 is -CHR2heteroaryl."

Whereas it should read:
-- wherein X is –O- and R1 is -CHR2heteroaryl. --

Signed and Sealed this
Second Day of May, 2023

Katherine Kelly Vidal
*Director of the United States Patent and Trademark Office*